(12) United States Patent
Ohsawa et al.

(10) Patent No.: US 8,114,570 B2
(45) Date of Patent: Feb. 14, 2012

(54) PHOTOACID GENERATOR, RESIST COMPOSITION, AND PATTERNING PROCESS

(75) Inventors: Youichi Ohsawa, Joetsu (JP); Takeshi Kinsho, Joetsu (JP); Takeru Watanabe, Joetsu (JP); Koji Hasegawa, Joetsu (JP); Masaki Ohashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 511 days.

(21) Appl. No.: 12/410,357

(22) Filed: Mar. 24, 2009

(65) Prior Publication Data

US 2009/0246694 A1   Oct. 1, 2009

(30) Foreign Application Priority Data

Mar. 25, 2008   (JP) ................. 2008-078049

(51) Int. Cl.
  G03F 7/004   (2006.01)
  G03F 7/30    (2006.01)
  C07D 307/00  (2006.01)
  C07C 309/03  (2006.01)
  C07C 309/19  (2006.01)

(52) U.S. Cl. ............. 430/270.1; 430/326; 430/330; 430/910; 549/269; 549/300; 562/30; 562/111; 562/113

(58) Field of Classification Search ........... 430/270.1, 430/326, 330, 910; 549/269, 300; 562/30, 562/111, 113
See application file for complete search history.

(56) References Cited

U.S. PATENT DOCUMENTS

| | | | |
|---|---|---|---|
| 5,635,332 A | 6/1997 | Nakano et al. | |
| 5,705,702 A | 1/1998 | Osawa et al. | |
| 5,714,625 A | 2/1998 | Hada et al. | |
| 6,063,953 A | 5/2000 | Hada et al. | |
| 6,136,502 A | 10/2000 | Satoshi et al. | |
| 6,261,738 B1 | 7/2001 | Asakura et al. | |
| 6,306,555 B1 | 10/2001 | Schulz et al. | |
| 6,312,867 B1 | 11/2001 | Kinsho et al. | |
| 6,329,125 B2 | 12/2001 | Takechi et al. | |
| 6,440,634 B1 | 8/2002 | Ohsawa et al. | |
| 6,512,020 B1 | 1/2003 | Asakura et al. | |
| 6,723,483 B1 | 4/2004 | Oono et al. | |
| 6,830,866 B2 | 12/2004 | Kobayashi et al. | |
| 6,849,374 B2 | 2/2005 | Cameron et al. | |
| 6,893,792 B2 | 5/2005 | Miya et al. | |
| 7,288,359 B2 | 10/2007 | Iwasawa et al. | |
| 7,381,842 B2 | 6/2008 | Kunimoto et al. | |
| 7,399,577 B2 | 7/2008 | Yamato et al. | |
| 7,527,912 B2 * | 5/2009 | Ohsawa et al. | 430/270.1 |
| 7,927,780 B2 * | 4/2011 | Kawaue et al. | 430/270.1 |
| 2004/0260031 A1 | 12/2004 | Takeda et al. | |
| 2007/0003871 A1 | 1/2007 | Kodama et al. | |
| 2007/0078269 A1 | 4/2007 | Harada et al. | |
| 2007/0122750 A1 | 5/2007 | Yamaguchi et al. | |
| 2007/0218401 A1 | 9/2007 | Ando et al. | |
| 2007/0231738 A1 | 10/2007 | Kaneko et al. | |
| 2008/0318160 A1 | 12/2008 | Ohsawa et al. | |
| 2009/0208871 A1 * | 8/2009 | Kawaue et al. | 430/285.1 |
| 2010/0099042 A1 * | 4/2010 | Ohashi et al. | 430/270.1 |

FOREIGN PATENT DOCUMENTS

| | | |
|---|---|---|
| EP | 0 473 547 A1 | 3/1992 |
| JP | 4-230645 A | 8/1992 |
| JP | 7-25846 A | 1/1995 |
| JP | 8-311018 A | 11/1996 |
| JP | 9-15848 A | 1/1997 |
| JP | 9-73173 A | 3/1997 |
| JP | 9-90637 A | 4/1997 |
| JP | 9-95479 A | 4/1997 |
| JP | 9-208554 A | 8/1997 |
| JP | 9-230588 A | 9/1997 |
| JP | 9-301948 A | 11/1997 |
| JP | 2906999 B2 | 6/1999 |
| JP | 11-190904 A | 7/1999 |
| JP | 2000-314956 A | 11/2000 |
| JP | 2000-336121 A | 12/2000 |
| JP | 2001-122850 A | 5/2001 |
| JP | 2001-181221 A | 7/2001 |
| JP | 2001-233842 A | 8/2001 |
| JP | 2002-193887 A | 7/2002 |
| JP | 2002-193925 A | 7/2002 |
| JP | 2002-214774 A | 7/2002 |
| JP | 2003-66612 A | 3/2003 |
| JP | 2003-107706 A | 4/2003 |
| JP | 2003-252855 A | 9/2003 |
| JP | 2004-2252 A | 1/2004 |
| JP | 2004-4561 A | 1/2004 |
| JP | 2004-115630 A | 4/2004 |
| JP | 2004-531749 A | 10/2004 |

(Continued)

OTHER PUBLICATIONS

Choi et al., "Improved Lithographic Performance with Ultra-thin 193 nm Resist" Journal of Photopolymer Science and Technology, vol. 19, No. 3, 2006, pp. 313-318.

Lowe, "Synthesis of sulphonium salts" The chemistry of the sulphortiunn group Part 1, John Wiley & Sons, 1981, Chapter 11, pp. 267-312.

Devoe et al., "Photochemistry and Photophysics of Onium Salts*" Advances in Photochemistry, vol. 17, 1992 by John Wiley & Sons, pp. 313-320.

(Continued)

*Primary Examiner* — John Chu
(74) *Attorney, Agent, or Firm* — Birch, Stewart, Kolasch & Birch, LLP

(57) ABSTRACT

Photoacid generators generate sulfonic acids of formula (1a) upon exposure to high-energy radiation.

$$ROC(=O)R^1-COOCH_2CF_2SO_3^-H^+ \quad (1a)$$

RO is OH or $C_1$-$C_{20}$ organoxy, $R^1$ is a divalent $C_1$-$C_{20}$ aliphatic group or forms a cyclic structure with RO. The photoacid generators are compatible with resins and can control acid diffusion and are thus suited for use in chemically amplified resist compositions.

16 Claims, 4 Drawing Sheets

FOREIGN PATENT DOCUMENTS

| | | |
|---|---|---|
| JP | 2005-8766 A | 1/2005 |
| JP | 2005-84365 A | 3/2005 |
| JP | 2006-306856 A | 11/2006 |
| JP | 2007-145797 A | 6/2007 |
| JP | 2007-161707 A | 6/2007 |
| JP | 2007-297590 A | 11/2007 |
| JP | 2008-13551 A | 1/2008 |
| WO | WO-2004/074242 A2 | 9/2004 |
| WO | WO-2009/057769 A1 | 5/2009 |

OTHER PUBLICATIONS

Miller et al., "Deoxygenation of Sulfoxides Promoted by Electrophilic Silicon Reagents: Preparation of Aryl-Substituted Sulfonium Salts" J. Org. Chem., vol. 53, No. 23, 1988, pp. 5571-5573.

Arimitsu et al., "Sensitivity Enhancement of Chemical-Amplification-Type Photoimaging Materials by Acetoacetic Acid Derivatives" Journal of Photopolymer Science and Technology, vol. 8, No. 1 (1995), pp. 43-44.

Kudo et al., "Enhancement of the Senesitivity of Chemical-Amplification-type Photoimaging Materials by β-Tosyloxyketone Acetals" Journal of Photopolymer Science and Technology, vol. 8, No. 1 (1995), pp. 45-46.

Arimitsu et al., "Effect of Phenolic Hydroxyl Residues on the Improvement of Acid-Proliferation-Type Photoimaging Materials" Journal of Photopolymer Science and Technology, vol. 9, No. 1 (1996), pp. 29-30.

* cited by examiner

PHOTOACID GENERATOR, RESIST COMPOSITION, AND PATTERNING PROCESS

CROSS-REFERENCE TO RELATED APPLICATION

This non-provisional application claims priority under 35 U.S.C. §119(a) on Patent Application No. 2008-078049 filed in Japan on Mar. 25, 2008, the entire contents of which are hereby incorporated by reference.

TECHNICAL FIELD

This invention relates to novel photoacid generators, resist compositions comprising the same, and a patterning process using the same.

BACKGROUND ART

In the recent drive for higher integration and operating speeds in LSI devices, it is desired to miniaturize the pattern rule. Great efforts have been devoted for the development of the micropatterning technology using deep-ultraviolet (deep-UV) or vacuum-ultraviolet (VUV) lithography. The photolithography using KrF excimer laser (wavelength 248 nm) as the light source has already established the main role in the commercial manufacture of semiconductor devices. The lithography using ArF excimer laser (wavelength 193 nm) is under investigation to enable further miniaturization and has reached the stage of prototype manufacture experiments. However, the ArF excimer laser lithography has not matured so that many problems must be overcome before the technology can be applied to an industrial scale of semiconductor manufacture.

The requisite properties for the resist materials complying with the ArF excimer laser lithography include transparency at wavelength 193 nm and dry etch resistance. Resist materials comprising as a base resin poly(meth)acrylic acid derivatives having bulky acid-labile protective groups as typified by 2-ethyl-2-adamantyl and 2-methyl-2-adamantyl groups were proposed as having both the properties (JP-A 9-73173 and JP-A 9-90637). Since then, a variety of materials have been proposed. Most of them commonly use resins having a highly transparent backbone and a carboxylic acid moiety protected with a bulky tertiary alkyl group.

As the pattern layout becomes finer, the fluctuation of pattern line width, known as "line edge roughness" (LER), becomes significant. In the processing of gate electrode zones in the LSI circuit manufacturing process, for example, poor LER can give rise to such problems as current leakage, resulting in a transistor with degraded electrical properties. It is believed that the LER is affected by various factors. The main factor is the poor affinity of a base resin to a developer, that is, low solubility of a base resin in a developer. Since carboxylic acid protective groups commonly used in the art are bulky tertiary alkyl groups and thus highly hydrophobic, most of them are less soluble. Where a high resolution is required as in the formation of microscopic channels, a noticeable LER can lead to an uneven size. One of known approaches for reducing LER is by increasing the amount of photoacid generator added, as described in Journal of Photopolymer Science and Technology, vol. 19, No. 3, 2006, 313-318. This approach, however, exerts a less than satisfactory effect, sometimes at the substantial sacrifice of exposure dose dependency, mask fidelity and/or pattern rectangularity.

Studies have also been made on photoacid generators. In prior art chemically amplified resist compositions for lithography using KrF excimer laser, photoacid generators capable of generating alkane- or arene-sulfonic acid are used. However, the use of these photoacid generators in chemically amplified resist compositions for ArF lithography results in an insufficient acid strength to scissor acid labile groups on the resin, a failure of resolution or a low sensitivity. Thus these photoacid generators are not suited for the fabrication of microelectronic devices.

For the above reason, photoacid generators capable of generating perfluoroalkanesulfonic acid having a high acid strength are generally used in ArF chemically amplified resist compositions. Perfluorooctanesulfonic acid and derivatives thereof (collectively referred to as PFOS) are considered problematic with respect to their stability (or non-degradability) due to C—F bonds, and biological concentration and accumulation due to hydrophobic and lipophilic natures. With respect to perfluoroalkanesulfonic acids of 5 or more carbon atoms and derivatives thereof, the same problems are pointed out.

Facing the PFOS-related problems, manufacturers made efforts to develop partially fluorinated alkane sulfonic acids having a reduced degree of fluorine substitution. For instance, JP-A 2004-531749 describes the development of α,α-difluoroalkanesulfonic acid salts from α,α-difluoroalkene and a sulfur compound and discloses a resist composition comprising a photoacid generator which generates such sulfonic acid upon irradiation, specifically di(4-tert-butylphenyl)iodonium 1,1-difluoro-2-(1-naphthyl)-ethanesulfonate. JP-A 2004-2252 describes the development of α,α,β,β-tetrafluoroalkanesulfonic acid salts from α,α,β,β-tetrafluoro-α-iodoalkane and sulfur compound and discloses a photoacid generator capable of generating such a sulfonic acid and a resist composition comprising the same. JP-A 2002-214774 discloses photoacid generators having difluorosulfoacetic acid alkyl esters (e.g., 1-(alkoxycarbonyl)-1,1-difluoromethanesulfonate) and difluorosulfoacetic acid amides (e.g., 1-carbamoyl-1,1-difluoromethanesulfonate) although their synthesis method is lacking. Furthermore, JP-A 2004-4561 discloses triphenylsulfonium(adamantan-1-ylmethyl) oxycarbonyldifluoro-methanesulfonate although its synthesis method is lacking; JP-A 2006-306856 discloses triphenylsulfonium alkyloxycarbonyldifluoromethanesulfonates having a lactone structure and analogs; JP-A 2007-145797 discloses triphenylsulfonium 2-acyloxy-1,1,3,3,3-hexafluoropropane-sulfonate and analogs; and JP-A 2007-161707 discloses a photoacid generator capable of generating a partially fluorinated alkane sulfonic acid having a polycyclic hydrocarbon group.

As far as the inventors empirically confirmed, undesirably these compounds suffer from problems including difficult compound design due to limited starting reactants (JP-A 2004-531749, JP-A 2004-2252), low solubility (JP-A 2002-214774, JP-A 2004-4561, JP-A 2006-306856, JP-A 2007-161707), and increased hydrophobicity due to many fluorine atoms (JP-A 2007-145797).

With respect to the immersion lithography, there remain some other problems. Minute water droplets are left on the resist and wafer after the immersion exposure, which can often cause damages and defects to the resist pattern profile. The resist pattern after development can collapse or deform into a T-top profile. There exists a need for a patterning process which can form a satisfactory resist pattern after development according to the immersion lithography.

In forming fine size patterns, the size difference between isolated and grouped patterns having different optical contrast, known as pattern density dependence or optical proximity effect, becomes more significant. Using a photoacid generator capable of generating a low diffusible acid, the problem of pattern density dependence can be overcome to some extent, but not to a satisfactory extent. While the resist composition is required to achieve a further reduction of the pattern rule as well as a good balance of sensitivity, substrate adhesion, and etching resistance, it is also required to ameliorate the pattern density dependency without sacrificing resolution.

CITATION LIST

Patent Document 1: JP-A H09-73173
Patent Document 2: JP-A H09-90637
Patent Document 3: JP-A 2004-531749
Patent Document 4: JP-A 2004-2252
Patent Document 5: JP-A 2002-214774
Patent Document 6: JP-A 2004-4561
Patent Document 7: JP-A 2006-306856
Patent Document 8: JP-A 2007-145797
Patent Document 9: JP-A 2007-161707
Non-Patent Document 1: Journal of Photopolymer Science and Technology, vol. 19, No. 3, 2006, 313-318

SUMMARY OF INVENTION

The photoacid generator (PAG) produces an acid which must satisfy many requirements including a sufficient acid strength to cleave acid labile groups in a resist material, stability in the resist material during shelf storage, an adequate diffusion in the resist material, low volatility, minimal leach-out in water, little foreign matter left after development and resist removal, and good degradability in that it is decomposed away after the expiration of its role in lithography without imposing a load to the environment. No acids produced by prior art PAGs satisfy these requirements. Moreover, resist compositions using prior art photoacid generators fail to solve the problems of pattern density dependency and LER without sacrificing resolution.

An object of the invention is to solve the problems of prior art photoacid generators, and to provide novel photoacid generators suited for use in resist materials which generators are effective in the ArF immersion lithography due to minimized leach-out in water and controlled formation of foreign matter inherent to the immersion lithography, and overcome the problems of pattern density dependency and LER. Another object is to provide a resist composition using the photoacid generator, and a patterning process.

The inventors have found that by starting with 2-bromo-2, 2-difluoroethanol which is readily available in the industry, compounds of 1,1-difluoro-2-acyloxypropane-1-sulfonate having a carbonyl group, carboxyl group or carboxylate or lactone structure can be prepared, and that these compounds, typically onium salts, oximes and imides are effective photoacid generators in chemically amplified resist compositions. The present invention is predicated on this finding.

The present invention provides novel photoacid generators, resist compositions and a patterning process, defined below.

[1] A photoacid generator for chemically amplified resist compositions which generates a sulfonic acid in response to high-energy radiation selected from UV, deep-UV, EUV, electron beam, x-ray, excimer laser, gamma-ray and synchrotron radiation, said sulfonic acid having the general formula (1a):

$$ROC(=O)R^1—COOCH_2CF_2SO_3^-H^+ \quad (1a)$$

wherein RO is hydroxyl or a substituted or unsubstituted, straight, branched or cyclic $C_1$-$C_{20}$ organoxy group, $R^1$ is a divalent $C_1$-$C_{20}$ aliphatic group which may contain a substituent group having a heteroatom such as oxygen, nitrogen or sulfur, or may form a mono- or polycyclic structure with RO.

[2] A sulfonium salt having the general formula (2):

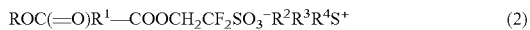

$$ROC(=O)R^1—COOCH_2CF_2SO_3^-R^2R^3R^4S^+ \quad (2)$$

wherein RO and $R^1$ are as defined above, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom.

[3] A sulfonium salt having the general formula (2a):

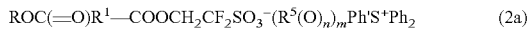

$$ROC(=O)R^1—COOCH_2CF_2SO_3^-(R^5(O)_n)_mPh'S^+Ph_2 \quad (2a)$$

wherein RO and $R^1$ are as defined above, $R^5$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 or 1, Ph denotes phenyl, and Ph' denotes a phenyl group in which a number "m" of hydrogen atoms are substituted by $R^5(O)_n$— groups.

[4] A iodonium salt having the general formula (2b):

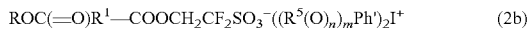

$$ROC(=O)R^1—COOCH_2CF_2SO_3^-((R^5(O)_n)_mPh')_2I^+ \quad (2b)$$

wherein RO, $R^1$, $R^5$, m, n, and Ph' are as defined above.

[5] A resist composition comprising a base resin, an acid generator, and an organic solvent, said acid generator comprising the photoacid generator of [1] capable of generating a sulfonic acid having formula (1a), the sulfonium salt of [2] or [3], or the iodonium salt of [4].

[6] The resist composition of [5], wherein said base resin is one or more polymers selected from the group consisting of poly(meth)acrylic acid and derivatives thereof, cycloolefin derivative/maleic anhydride alternating copolymers, copolymers of ternary or more components comprising a cycloolefin derivative, maleic anhydride, and polyacrylic acid or derivatives thereof, cycloolefin derivative/α-trifluoromethyl acrylate derivative copolymers, polynorbornene, ring-opening metathesis polymers, and hydrogenated ring-opening metathesis polymers.

[7] The resist composition of [5], wherein said base resin is a polymeric structure containing silicon atoms.

[8] The resist composition of [5], wherein said base resin is a polymeric structure containing fluorine atoms.

[9] A chemically amplified positive resist composition comprising a base resin as set forth in [6], [7] or [8], a photoacid generator capable of generating a sulfonic acid having formula (1a) as set forth in [1], and a solvent, wherein said base resin is insoluble or substantially insoluble in a developer, and becomes soluble under the action of the acid.

[10] The resist composition of [9], further comprising a quencher.

[11] The resist composition of [9] or [10], further comprising a dissolution inhibitor.

[12] The resist composition of any one of [9] to [11], further comprising a surfactant which is insoluble in water and soluble in an alkaline developer.

[13] A pattern forming process comprising the steps of applying the resist composition of any one of [9] to [12] onto a substrate to form a coating, heat treating the coating and exposing it to high-energy radiation through a photomask, and optionally heat treating and developing the exposed coating with a developer.

[14] A pattern forming process comprising the steps of applying the resist composition of any one of [9] to [12] onto a substrate to form a resist coating, heat treating the resist coating, applying on the resist coating a protective coating which is insoluble in water and soluble in an alkaline developer, exposing the coated substrate to high-energy radiation through a photomask and a projection lens, while holding water between the coated substrate and the projection lens, and optionally heat treating, and developing the exposed coating with a developer.

[15] A pattern forming process comprising the steps of applying the resist composition of any one of [9] to [12] onto a substrate to form a coating, heat treating the coating, imagewise writing with an electron beam, optionally heat treating the coating, and developing it with a developer.

[16] A pattern forming process comprising the steps of applying the resist composition of any one of [9] to [12] onto a substrate to form a coating, heat treating the coating and exposing it to high-energy radiation through a photomask, and heat treating and developing the exposed coating with a developer, wherein the process further comprises the step of applying a protective coating on the resist coating, and the exposure step is performed by immersion lithography with a liquid having a refractive index of at least 1.0 held between the protective coating and a projection lens.

ADVANTAGEOUS EFFECT OF INVENTION

Since the photoacid generators have a carboxyl group, carboxylate structure or lactone structure in addition to the acyloxy group at β-position relative to the sulfonate, they enable to adequately control acid diffusion and are fully compatible with resins and other components in resist compositions. The photoacid generators that generate these sulfonic acids perform well without raising problems during the device fabrication process including coating, pre-baking, exposure, post-exposure baking, and developing steps. The leach-out of sulfonic acids in water during the ArF immersion lithography is minimized. The influence of water left on the wafer is minimized, restraining defects from forming. In the disposal of resist-containing waste liquid after the device fabrication, acyloxy groups at β-position are hydrolyzable under basic conditions so that the sulfonic acids are transformed into less accumulative compounds of lower molecular weight. In the disposal by combustion, the sulfonic acids are more combustible because of a low degree of fluorine substitution.

DESCRIPTION OF THE PREFERRED EMBODIMENTS

Figure 1:
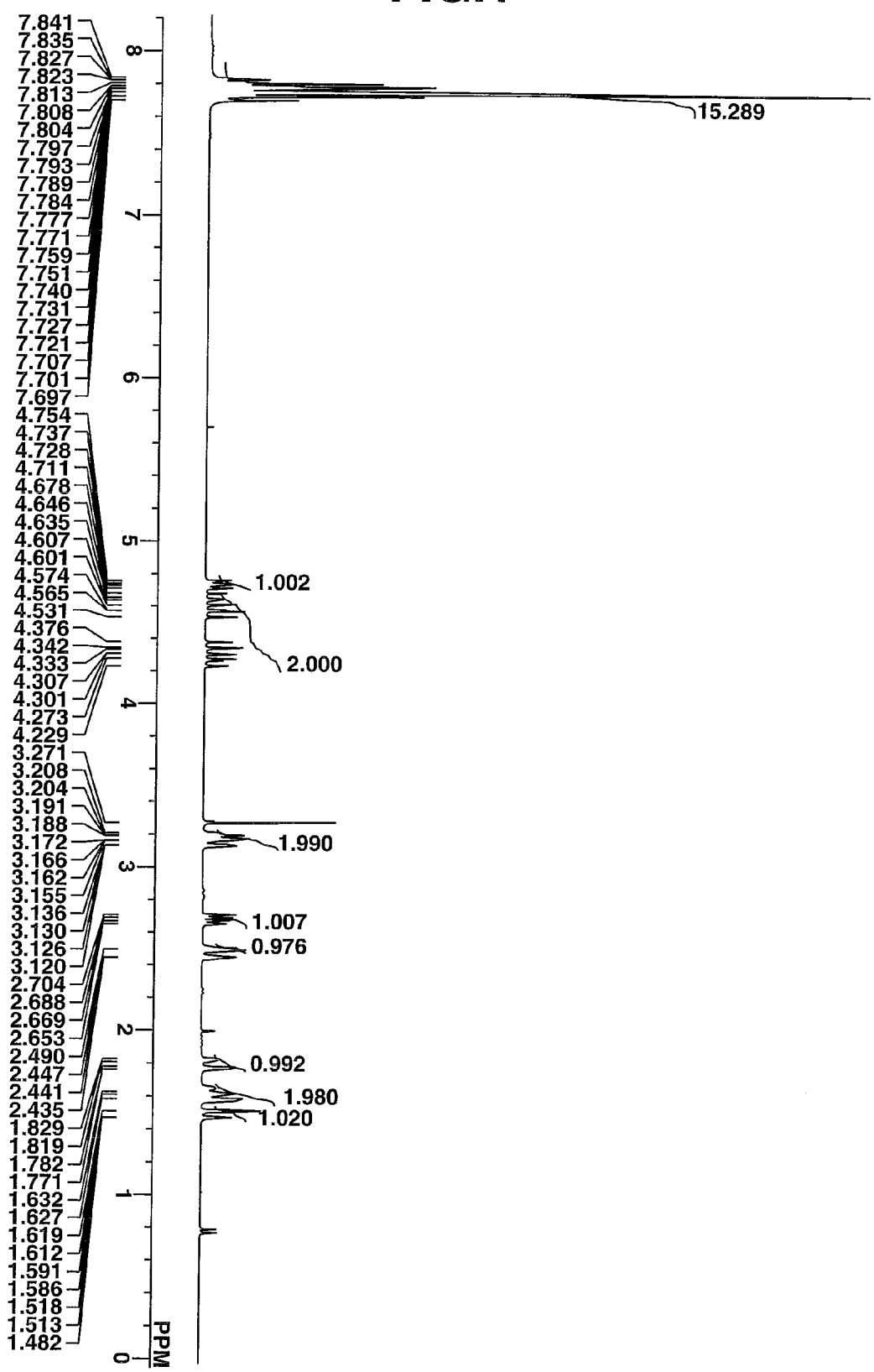
FIG. 1 is a diagram showing the $^1$H-NMR/DMSO-$d_6$ spectrum of PAG-A in Synthesis Example 14.

The singular forms "a," "an" and "the" include plural referents unless the context clearly dictates otherwise.

The notation (Cn-Cm) means a group containing from n to m carbon atoms per group.

Photoacid Generator

The photoacid generators of the invention are compounds, typically sulfonium salts, iodonium salts, oxime sulfonates and sulfonyloxyimides. These compounds are sensitive to high-energy radiation such as UV, deep-UV, EUV, electron beam, x-ray, excimer laser, gamma-ray and synchrotron radiation and generate sulfonic acids having the general formula (1a) in response to high-energy radiation, so that they are useful as photoacid generators in chemically amplified resist compositions.

$$ROC(=O)R^1-COOCH_2CF_2SO_3^-H^+ \quad (1a)$$

Herein RO is hydroxyl or a substituted or unsubstituted, straight, branched or cyclic $C_1$-$C_{20}$ organoxy group, $R^1$ is a divalent $C_1$-$C_{20}$ aliphatic group which may contain a substituent group having a heteroatom such as oxygen, nitrogen or sulfur, or $R^1$ may form a mono- or polycyclic structure with RO.

In formula (1a), RO is hydroxyl or a substituted or unsubstituted, straight, branched or cyclic $C_1$-$C_{20}$ organoxy group, typically alkoxy group. $R^1$ is a divalent $C_1$-$C_{20}$ aliphatic group, typically alkylene or alkenylene group, which may contain a substituent group having a heteroatom such as oxygen, nitrogen or sulfur. Alternatively, $R^1$ forms a monocyclic or polycyclic structure with RO. Suitable substituent groups on RO include hydroxy, alkoxyl, aryloxy, fluoro, chloro, bromo, iodo, carboxyl, alkoxycarbonyl, amido, carbonyl, and ether-bonding oxygen. When RO is an alkoxy group, one or more hydrogen atoms on the alkoxy may be substituted by aryl groups.

Illustrative examples of RO include hydroxy, methoxy, ethoxy, n-propoxy, isopropoxy, cyclopropyloxy, n-butoxy, sec-butoxy, isobutoxy, tert-butoxy, n-pentyloxy, cyclopentyloxy, n-hexyloxy, cyclohexyloxy, n-octyloxy, n-decyloxy, n-dodecyloxy, 1-adamantyloxy, 2-adamantyloxy, bicyclo[2.2.1]hepten-2-yloxy, 1-adamantanemethoxy, 2-adamantanemethoxy, phenoxy, 4-methoxyphenyloxy, 4-tert-butylphenyloxy, 4-biphenyloxy, 1-naphthyloxy, 2-naphthyloxy, 10-anthranyloxy, 2-furanyloxy, 2,2,2-trifluoroethoxy, 1,1,1,3,3,3-hexafluoro-2-propyloxy, and 2,2,3,3-tetrafluoropropoxy. Inter alia, hydroxy, methoxy, cyclohexyloxy, and 1-adamantanemethoxy are preferred.

$R^1$ is a divalent $C_1$-$C_{20}$ aliphatic group which may contain a substituent group having a heteroatom such as oxygen, nitrogen or sulfur, or may form a cyclic structure with RO. Suitable substituent groups on $R^1$ include hydroxy, alkoxy, aryloxy, fluoro, chloro, bromo, iodo, carboxyl, alkoxycarbonyl, amido, carbonyl, acyloxy, benzoyloxy, and ether-bonding oxygen. Illustrative examples of $R^1$ include methylene, ethylene, 1,3-propylene, 1,2-propylene, isopropylidene, 1,4-butylene, 1,6-hexylene, and those of the following structural formulae wherein the broken line denotes a bonding site.

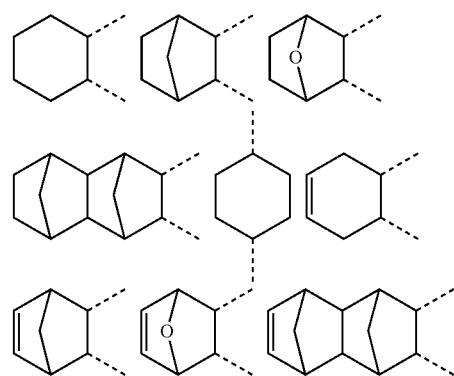

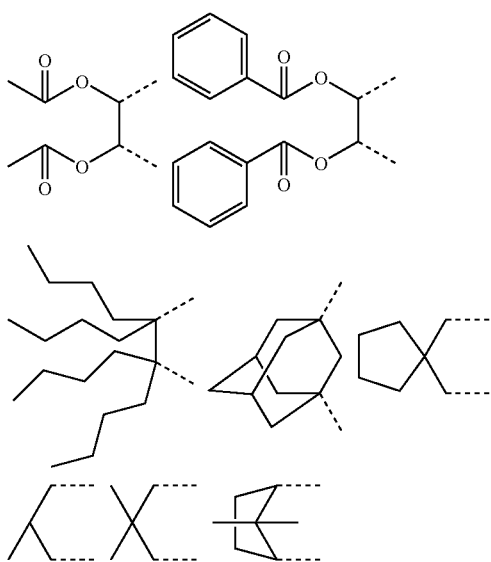
Of these, ethylene, 1,3-propylene and those groups of the following structural formulae are preferred.
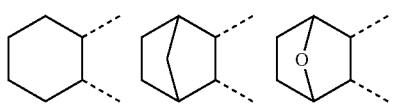
In one embodiment, RO bonds with $R^1$ to form the following structure.
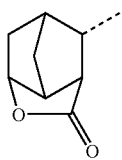
Illustrative, non-limiting examples of sulfonic acids are given below.
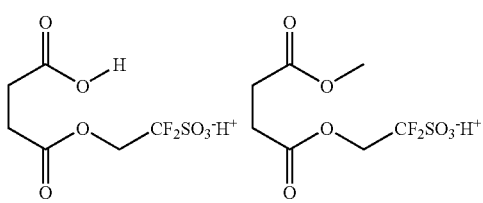
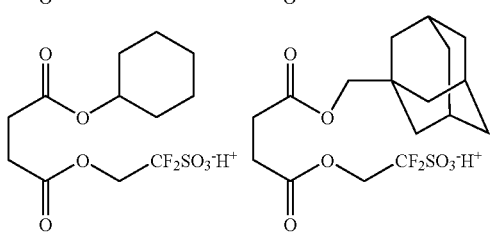
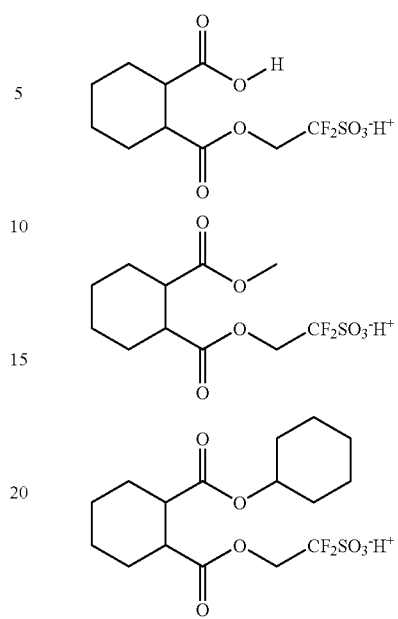
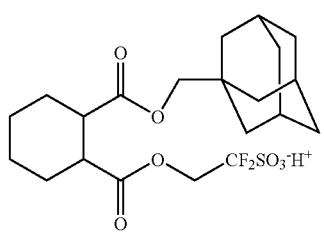
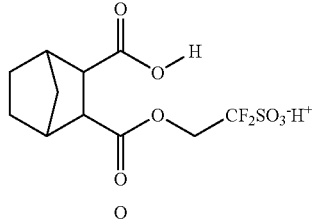
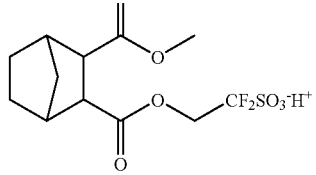
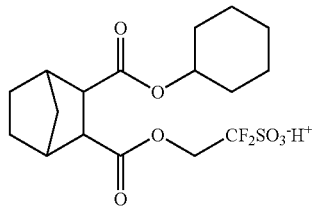
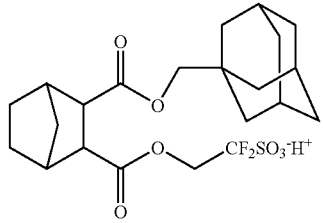

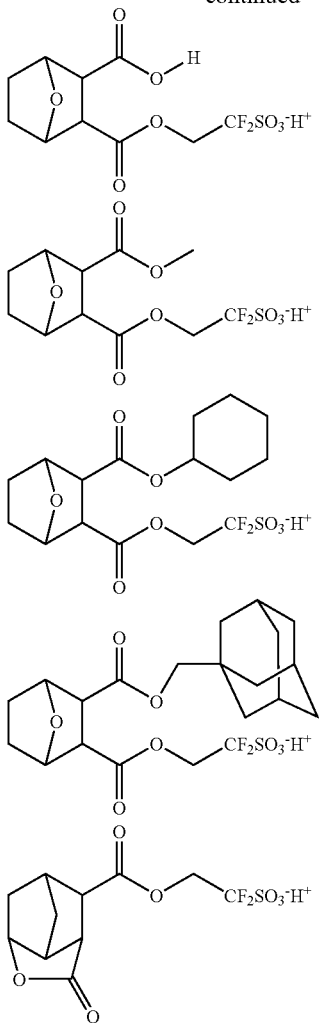

Sulfonium Salt

The sulfonium salt of the invention has the general formula (2).

$$ROC(=O)R^1\text{—}COOCH_2CF_2SO_3{}^-R^2R^3R^4S^+ \quad (2)$$

Herein RO is hydroxyl or a substituted or unsubstituted, straight, branched or cyclic $C_1$-$C_{20}$ organoxy group. $R^1$ is a divalent $C_1$-$C_{20}$ aliphatic group which may contain a substituent group having a heteroatom such as oxygen, nitrogen or sulfur, or may form a mono- or polycyclic structure with RO. $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom (in the formula).

In formula (2), RO and $R^1$ are as defined above. $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or any two or more of $R^2$, $R^3$ and $R^4$ may bond together to form a ring with the sulfur atom (in the formula). Suitable alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl, and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include phenyl, naphthyl, and thienyl; 4-hydroxyphenyl; alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include benzyl, 1-phenylethyl and 2-phenylethyl. Suitable aryloxoalkyl groups include 2-aryl-2-oxoethyl groups such as 2-phenyl-2-oxoethyl, 2-(1-naphthyl)-2-oxoethyl, and 2-(2-naphthyl)-2-oxoethyl. When two or more of $R^2$, $R^3$ and $R^4$ bond together to form a cyclic structure with the sulfur atom, divalent organic groups such as 1,4-butylene and 3-oxa-1,5-pentylene are exemplary of the cyclic structure-forming group. Also included are aryl groups having polymerizable substituent radicals such as acryloyloxy and methacryloyloxy radicals, and examples of such aryl groups are 4-acryloyloxyphenyl, 4-methacryloyloxyphenyl, 4-acryloyloxy-3,5-dimethylphenyl, 4-methacryloyloxy-3,5-dimethylphenyl, 4-vinyloxyphenyl, and 4-vinylphenyl groups.

Illustrative examples of the sulfonium cation include triphenylsulfonium, 4-hydroxyphenyldiphenylsulfonium, bis(4-hydroxyphenyl)phenylsulfonium, tris(4-hydroxyphenyl)sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. Preferred cations are triphenylsulfonium, 4-tert-butylphenyldiphenylsulfonium, 4-tert-butoxyphenyldiphenylsulfonium, tris(4-tert-butylphenyl)sulfonium, and 4-tert-butoxycarbonylmethyloxyphenyldiphenylsulfonium. Also included are 4-methacryloyloxyphenyldiphenylsulfonium, 4-acryloyloxyphenyldiphenylsulfonium, 4-methacryloyloxyphenyldimethylsulfonium, 4-acryloyloxyphenyldimethylsulfonium, (4-methacryloyloxy-3,5-dimethylphenyl)diphenylsulfonium, (4-acryloyloxy-3,5-dimethylphenyl)diphenylsulfonium, and the like. For these polymerizable sulfonium cations, reference may be made to JP-A 4-230645 and JP-A 2005-84365. These polymerizable sulfonium salts may be used as a monomer in forming a polymer to be described later.

Another embodiment is a sulfonium salt having the general formula (2a).

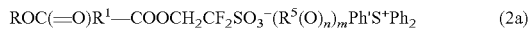

$$ROC(=O)R^1—COOCH_2CF_2SO_3^-(R^5(O)_n)_mPh'S^+Ph_2 \quad (2a)$$

Herein RO is hydroxyl or a substituted or unsubstituted, straight, branched or cyclic $C_1$-$C_{20}$ organoxy group. $R^1$ is a divalent $C_1$-$C_{20}$ aliphatic group which may contain a substituent group having a heteroatom such as oxygen, nitrogen or sulfur, or may form a mono- or polycyclic structure with RO. $R^5$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 or 1, Ph denotes phenyl, and Ph' denotes a phenyl group in which a number "m" of hydrogen atoms are substituted by $R^5(O)_n$— groups.

In formula (2a), RO and $R^1$ are as defined above. The substitution position of $R^5$—$(O)_n$— group is not particularly limited, but is preferably 4- or 3-position on the phenyl group, and more preferably 4-position. Examples of groups represented by $R^5$ include methyl, ethyl, n-propyl, sec-propyl, cyclopropyl, n-butyl, sec-butyl, isobutyl, tert-butyl, n-pentyl, cyclopentyl, n-hexyl, cyclohexyl, n-octyl, n-decyl, n-dodecyl, trifluoromethyl, phenyl, 4-methoxyphenyl, and 4-tert-butylphenyl. In the case of n=1, acryloyl, methacryloyl, vinyl, and allyl are exemplary of $R^5$. The letter m is an integer of 1 to 5, and preferably 1, and n is 0 (zero) or 1.

Illustrative examples of the sulfonium cation include 4-methylphenyldiphenylsulfonium, 4-ethylphenyldiphenylsulfonium, 4-tert-butylphenyldiphenylsulfonium, 4-cyclohexylphenyldiphenylsulfonium, 4-n-hexylphenyldiphenylsulfonium, 4-n-octylphenyldiphenylsulfonium, 4-methoxyphenyldiphenylsulfonium, 4-ethoxyphenyldiphenylsulfonium, 4-tert-butoxyphenyldiphenylsulfonium, 4-cyclohexyloxyphenyldiphenylsulfonium, 4-n-hexyloxyphenyldiphenylsulfonium, 4-n-octyloxyphenyldiphenylsulfonium, 4-dodecyloxyphenyldiphenylsulfonium, 4-trifluoromethylphenyldiphenylsulfonium, 4-trifluoromethyloxyphenyldiphenylsulfonium, 4-tert-butoxycarbonylmethyloxyphenyldiphenylsulfonium, 4-methacryloyloxyphenyldiphenylsulfonium, 4-acryloyloxyphenyldiphenylsulfonium, (4-n-hexyloxy-3,5-dimethylphenyl)diphenylsulfonium, (4-methacryloyloxy-3,5-dimethylphenyl)diphenylsulfonium, and (4-acryloyloxy-3,5-dimethylphenyl)diphenylsulfonium.

Iodonium Salt

A further embodiment of the invention is a iodonium salt having the general formula (2b).

$$ROC(=O)R^1—COOCH_2CF_2SO_3^-((R^5(O)_n)_mPh')_2I^+ \quad (2b)$$

Herein RO is hydroxyl or a substituted or unsubstituted, straight, branched or cyclic $C_1$-$C_{20}$ organoxy group. $R^1$ is a divalent $C_1$-$C_{20}$ aliphatic group which may contain a substituent group having a heteroatom such as oxygen, nitrogen or sulfur, or may form a mono- or polycyclic structure with RO. $R^5$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 or 1, and Ph' denotes a phenyl group in which a number "m" of hydrogen atoms are substituted by $R^5(O)_n$— groups.

In formula (2b), RO, $R^1$, $R^5$, n and m are as defined and illustrated above. The substitution position of $R^5$—$(O)_n$— group is not particularly limited, but is preferably 4- or 3-position on the phenyl group, and more preferably 4-position.

Illustrative examples of the iodonium cation include bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, and 4-methacryloyloxyphenylphenyliodonium, with the bis(4-tert-butylphenyl)iodonium being preferred.

Besides the foregoing sulfonium and iodonium salts, the photoacid generators for use in chemically amplified resist compositions further include photoacid generators which generate sulfonic acids having the general formula (1a) in response to high-energy radiation such as UV, deep-UV, EUV, electron beam, x-ray, excimer laser, gamma-ray and synchrotron radiation. They are sulfonyloxyimides and oxime sulfonates, but not limited thereto.

N-sulfonyloxyimide

A further embodiment of the invention is a N-sulfonyloxyimide compound having the general formula (3a).

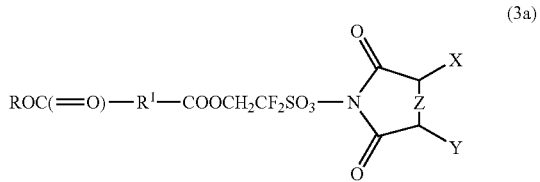

Herein RO is hydroxyl or a substituted or unsubstituted, straight, branched or cyclic $C_1$-$C_{20}$ organoxy group. $R^1$ is a divalent $C_1$-$C_{20}$ aliphatic group which may contain a substituent group having a heteroatom such as oxygen, nitrogen or sulfur, or may form a mono- or polycyclic structure with RO. X and Y are each independently hydrogen or a substituted or unsubstituted $C_1$-$C_6$ alkyl group, or X and Y may bond together to form a saturated or unsaturated $C_6$-$C_{12}$ ring with the carbon atoms to which they are attached, and Z is a single bond, double bond, methylene group or oxygen atom.

In formula (3a), RO and $R^1$ are as defined above, X and Y are each independently hydrogen or a substituted or unsubstituted $C_1$-$C_6$ alkyl group, or X and Y may bond together to form a saturated or unsaturated, non-aromatic $C_6$-$C_{12}$ ring with the carbon atoms to which they are attached, and Z is a single bond, double bond, methylene group or oxygen atom. Illustrative examples of the imide skeleton excluding the sulfonate moiety are given below wherein the broken line denotes a bonding site to the sulfonate moiety. For the imide skeleton, reference may be made to JP-A 2003-252855.

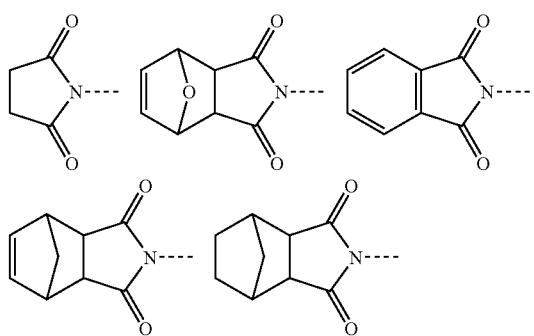

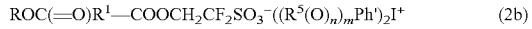

-continued

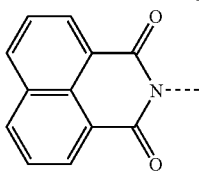

Oxime Sulfonate

A further embodiment of the invention is an oxime sulfonate compound having the general formula (3b).

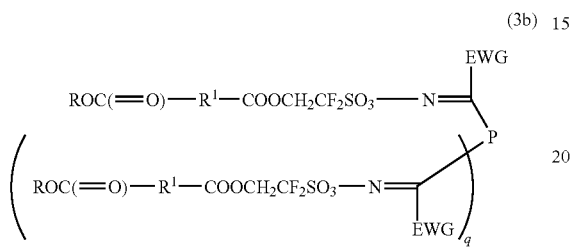

(3b)

Herein RO is hydroxyl or a substituted or unsubstituted, straight, branched or cyclic $C_1$-$C_{20}$ organoxy group; $R^1$ is a divalent $C_1$-$C_{20}$ aliphatic group which may contain a substituent group having a heteroatom such as oxygen, nitrogen or sulfur, or may form a mono- or polycyclic structure with RO; q is 0 (zero) or 1; when q is 0, p is a substituted or unsubstituted $C_1$-$C_{20}$ alkyl group or a substituted or unsubstituted $C_6$-$C_{15}$ aryl group; when q is 1, p is a single bond, a substituted or unsubstituted $C_1$-$C_{20}$ alkylene group or a substituted or unsubstituted $C_6$-$C_{15}$ arylene group; EWG is a cyano, trifluoromethyl, perfluoroethyl, perfluoropropyl, 5H-perfluoropentyl, 6H-perfluorohexyl, nitro or methyl group, and when q is 1, two EWG's may bond together to form a ring of 6 carbon atoms with the carbon atoms to which they are attached.

In formula (3b), RO and $R^1$ are as defined above. When q is equal to 0, p is a substituted or unsubstituted $C_1$-$C_{20}$ alkyl group or a substituted or unsubstituted $C_6$-$C_{15}$ aryl group. When q is equal to 1, p is a single bond, a substituted or unsubstituted $C_1$-$C_{20}$ alkylene group or a substituted or unsubstituted $C_6$-$C_{15}$ arylene group. EWG is a cyano, trifluoromethyl, perfluoroethyl, perfluoropropyl, 5H-perfluoropentyl, 6H-perfluorohexyl, nitro or methyl group. When q is equal to 1, two EWG's may bond together to form a ring of 6 carbon atoms with the carbon atoms to which they are attached. The skeletons of the oxime sulfonates are described in U.S. Pat. No. 6,261,738, JP-A 9-95479, JP-A 9-208554, JP-A 9-230588, JP 2,906,999, JP-A 9-301948, JP-A 2000-314956, JP-A 2001-233842, and WO 2004/074242.

Exemplary skeletons of oxime sulfonates excluding the sulfonate moiety are given below wherein the broken line denotes a bonding site to the sulfonate moiety.

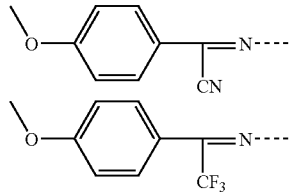

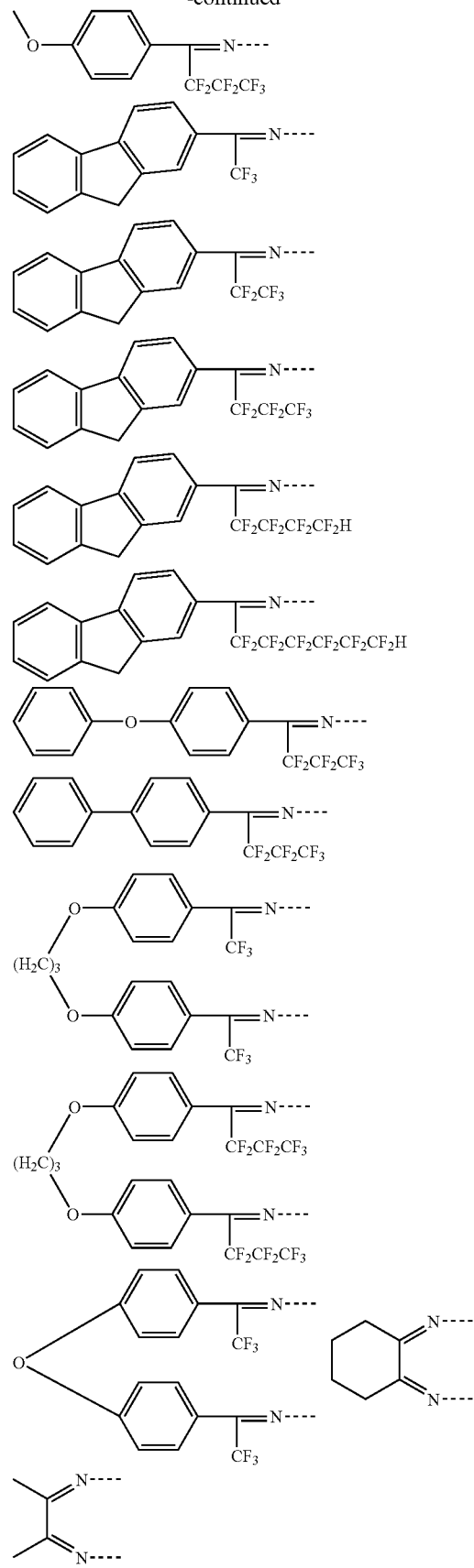

Described below is how to synthesize the sulfonium salts of formula (2) as typical examples of the foregoing photoacid generators capable of generating a sulfonic acid of formula (1a).

One exemplary compound may be synthesized by reacting 2-bromo-2,2-difluoroethanol with a carboxylic acid chloride to form 2-bromo-2,2-difluoroethyl alkanecarboxylate or 2-bromo-2,2-difluoroethyl arenecarboxylate, converting the bromo group into sodium sulfinate using a sulfur compound such as sodium dithionite, and converting sulfinic acid into sulfonic acid using an oxidizing agent such as hydrogen peroxide. The outline of the process is illustrated below.

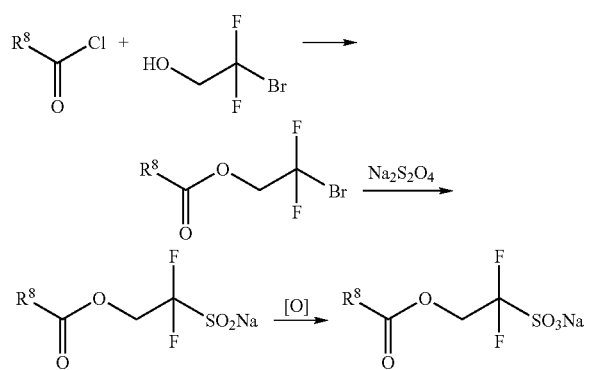

Herein $R^8$ is a straight, branched or cyclic $C_1$-$C_{20}$ alkyl group which may contain a heteroatom or ROC(=O)—$R^1$— wherein R and $R^1$ are as defined above.

The steps of esterification, conversion from alkane halide to sodium sulfinate, and conversion to sulfonic acid are well known, while the formulations used in the latter two steps are described in JP-A 2004-2252.

Subsequent ion exchange reaction between the resulting sodium sulfonate and a sulfonium salt compound yields the desired sulfonium salt. With respect to ion exchange reaction, reference is made to JP-A 2007-145797.

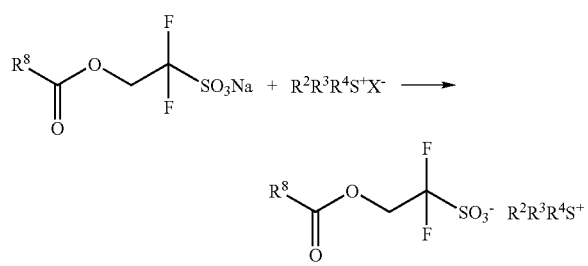

Herein, $R^2$ to $R^4$ and $R^8$ are as defined above. $X^-$ is a counter anion. Exemplary anions include, but are not limited to, halide ions such as $I^-$, $Br^-$ and $Cl^-$, sulfate and alkylsulfate anions such as sulfate and methylsulfate anions, carboxylate anions such as acetate and benzoate, alkanesulfonates such as methanesulfonate and propanesulfonate, arenesulfonates such as benzenesulfonate and p-toluenesulfonate, and hydroxide.

Further, the acyl group $R^8$CO— introduced as above is subjected to ester hydrolysis or solvolysis and then acylated again whereby a substituent group ROC(=O)—$R^1$—CO can be introduced. The outline of the process is illustrated below.

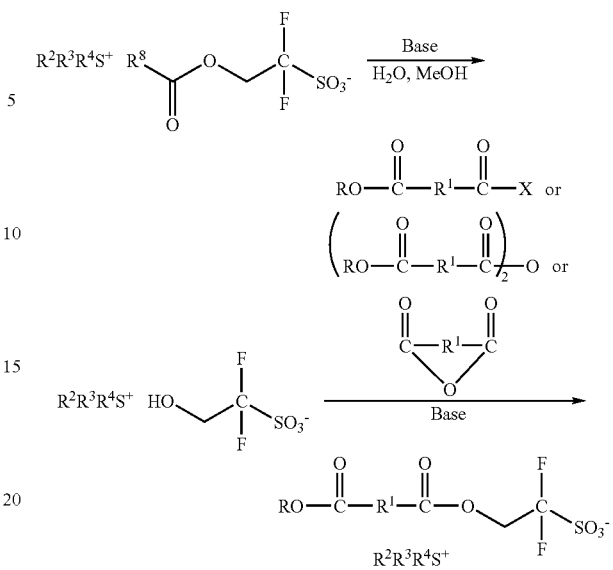

Note that RO, $R^1$ to $R^4$, and $R^8$ are as defined above, and X is a halogen atom such as chlorine and bromine.

This formulation makes it possible to introduce a substituent group which is unstable under the conditions of the previous anion synthesis process (conversion of a bromo group into sodium sulfinate using a sulfur compound such as sodium dithionite and subsequent conversion of sulfinic acid into sulfonic acid using an oxidizing agent such as hydrogen peroxide).

The sulfonium and iodonium salts of formulae (2a) and (2b) may be similarly synthesized. The starting sulfonium and iodonium salts may be synthesized according to the teachings of The Chemistry of Sulfonium Group Part 1, John-Wiley & Sons (1981), Advanced Photochemistry, vol. 17, John-Wiley & Sons (1992), J. Org. Chem., 1988, 53, 5571-5573, JP-A 8-311018, JP-A 9-15848, JP-A 2001-122850, JP-A 7-25846, JP-A 2001-181221, JP-A 2002-193887, and JP-A 2002-193925. An onium cation having an acryloyloxy or methacryloyloxy group as a polymerizable substituent group may be synthesized according to the methods of JP-A 4-230645 and JP-A 2005-84365, by reacting a hydroxyphenyldiphenylsulfonium halide (preformed) with acryloyl chloride or methacryloyl chloride under basic conditions.

In the synthesis of imide and oxime sulfonates of formulae (3a) and (3b), an imide or oxime sulfonate having a 1,1-difluoro-2-hydroxyethane sulfonate moiety is reacted with an aliphatic carboxylic halide or anhydride having a carboxylate or lactone structure, aromatic carboxylic halide or anhydride, aliphatic dicarboxylic anhydride or aromatic dicarboxylic anhydride, yielding an imide or oxime sulfonate having a carboxylate or lactone structure or carbonyl or carboxyl group.

Prior to this, synthesis of the imide or oxime sulfonate having a 1,1-difluoro-2-hydroxyethane sulfonate moiety may be performed by reacting 1,1-difluoro-2-acyloxy-ethane sulfonate with a chlorinating agent such as thionyl chloride, phosphorus oxychloride or phosphorus pentachloride to form a corresponding sulfonyl chloride or sulfonic acid anhydride, and reacting it with N-hydroxydicarboxyl imide or oxime in a conventional manner to form 1,1-difluoro-2-acyloxy-ethane sulfonate. Subsequent hydrolysis on the acyloxy group yields the desired intermediate, imide or oxime sulfonate having a 1,1-difluoro-2-hydroxyethane sulfonate moiety.

With respect to the synthesis of imide and oxime sulfonates, reference should be made to JP-A 2003-252855, U.S. Pat. No. 6,261,738, JP-A 9-95479, JP-A 9-208554, JP-A 9-230588, JP 2906999, JP-A 9-301948, JP-A 2000-314956, JP-A 2001-233842, and WO 2004/074242.

As described above, a first embodiment of the invention provides photoacid generators suited for use in chemically amplified resist compositions which generate sulfonic acids of formula (1a) upon exposure to high-energy radiation. A second embodiment provides sulfonium salts, iodonium salts, dicarboxylimide sulfonates, and oxime sulfonates serving as photoacid generators in chemically amplified resist compositions. A third embodiment provides chemically amplified resist compositions comprising a photoacid generator which generates a sulfonic acid of formula (1a) upon exposure to high-energy radiation and a resin which changes its solubility in an alkaline developer liquid under the action of acid.

Resist Composition

The resist composition of the invention is typically embodied as (i) a chemically amplified positive resist composition comprising (A) the above-mentioned photoacid generator, i.e., the photoacid generator capable of generating a sulfonic acid having formula (1a), especially the compound of formula (2), (2a), (2b), (3a) or (3b), (B) an organic solvent, (C) a base resin which changes its solubility in an alkaline developer under the action of acid, and one or more optional components including (D) a quencher, (E) a photoacid generator other than (A), (F) an organic acid derivative and/or fluorinated alcohol, and (G) a dissolution inhibitor having a weight average molecular weight of up to 3,000, and further optionally, (S) a surfactant which is insoluble or substantially insoluble in water and soluble in alkaline developer and/or a surfactant which is insoluble or substantially insoluble in water and alkaline developer; and (ii) a chemically amplified negative resist composition comprising (A) the above-mentioned photoacid generator, (B) an organic solvent, (C') a base resin which is normally alkali soluble, but becomes substantially alkali insoluble under the action of a crosslinker, (H) a crosslinker which induces crosslinkage under the action of acid, and one or more optional components including (D) a quencher and (E) a photoacid generator other than (A), and further optionally, (S) a surfactant which is insoluble or substantially insoluble in water and soluble in alkaline developer and/or a surfactant which is insoluble or substantially insoluble in water and alkaline developer.

The PAG which generates a sulfonic acid having formula (1a) as component (A) is as described above. More specifically, it is a compound having formula (2), (2a), (2b), (3a) or (3b). In the resist composition, the PAG is specifically compounded in an amount of 0.1 to 10 parts, more specifically 1 to 7 parts by weight per 100 parts by weight of the base resin. Note that parts by weight per 100 parts by weight of the resin is often abbreviated as "phr."

Component B

The organic solvent used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, PGMEA, cyclohexanone and mixtures thereof because the photoacid generator is most soluble therein.

An appropriate amount of the organic solvent used is 200 to 3,000 parts, especially 400 to 2,000 parts by weight per 100 parts by weight of the base resin.

Component C

The base resins used as component (C) or (C') in the inventive compositions include polyhydroxystyrene (PHS), and copolymers of PHS with styrene, (meth)acrylic acid esters or other polymerizable olefinic compounds, for KrF excimer laser resist use; (meth)acrylic acid ester polymers, alternating copolymers of cycloolefin with maleic anhydride and similar copolymers further containing vinyl ethers or (meth)acrylic acid esters, polynorbornene, ring-opening metathesis polymerized cycloolefins, and hydrogenated ring-opening metathesis polymerized cycloolefins, for ArF excimer laser resist use; and fluorinated forms of the foregoing polymers (for both KrF and ArF laser uses) for $F_2$ excimer laser resist use, although the base resins are not limited to these polymers. Understandably, the sulfonium salts and iodonium salts having polymerizable substituent groups according to the invention may be used as a monomer component in forming the base resin. Typical sulfonium and iodonium salts for such use are combinations of onium cations such as (4-acryloyloxyphenyl)diphenylsulfonium, (4-methacryloyloxyphenyl)diphenylsulfonium, (4-acryloyloxyphenyl)phenyliodonium, and (4-methacryloyloxyphenyl)phenyliodonium cations with anions such as 1-(difluorosulfomethyl)-2,2,2-trifluoroethyl hydrogen cyclohexanedicarboxylate. The base resins may be used alone or in admixture of two or more. In the case of positive resist compositions, it is a common practice to substitute acid labile groups for hydroxyl groups on phenols, carboxyl groups or fluorinated alkyl alcohols for reducing the rate of dissolution in unexposed regions.

The base resin (C) may comprise recurring units containing an acid labile group of the general formula (3) and recurring units of at least one type having the general formulae (4) to (6), shown below.

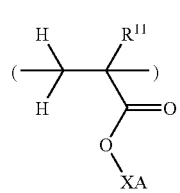

(3)

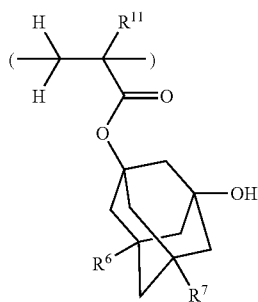
(4)

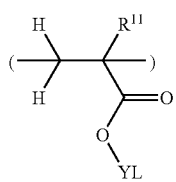
(5)

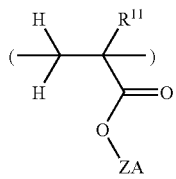
(6)

Herein, $R^{11}$ is hydrogen, fluorine, methyl or trifluoromethyl, $R^6$ and $R^7$ are each independently hydrogen or hydroxyl, XA is an acid labile group, YL is a lactone structure-containing substituent group, and ZA is hydrogen, $C_1$-$C_{15}$ fluoroalkyl group or $C_1$-$C_{15}$ fluoroalcohol-containing substituent group.

Under the action of an acid, a polymer comprising recurring units of formula (3) is decomposed to generate a carboxylic acid and turns into an alkali-soluble polymer. The acid labile groups represented by XA may be selected from a variety of such groups, for example, groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

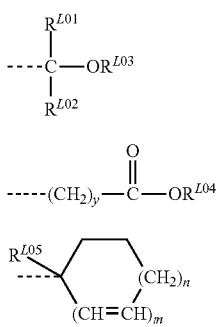

(L1)

(L2)

(L3)

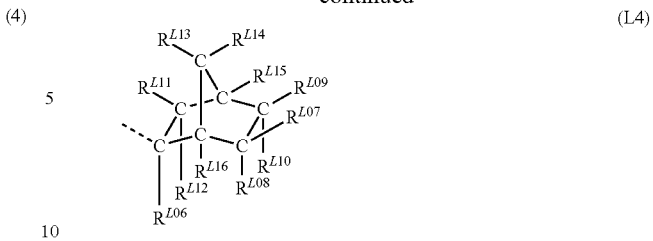
(L4)

The broken line indicates a valence bond.

In formula (L1), $R^{L01}$ and $R^{L02}$ are hydrogen or straight, branched or cyclic alkyl groups of 1 to 18 carbon atoms, preferably 1 to 10 carbon atoms. Examples include hydrogen, methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

$R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of these groups in which some hydrogen atoms are replaced by hydroxyl, alkoxy, oxo, amino, alkylamino or the like. Examples of the straight, branched or cyclic alkyl groups are as exemplified above for $R^{L01}$ and $R^{L02}$, and examples of the substituted alkyl groups are shown below.

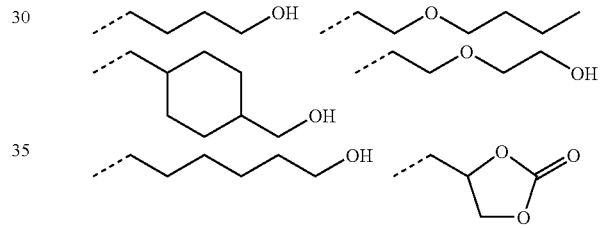

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached, and in this case, each group participating in ring formation is a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. In formula (L2), y is an integer of 0 to 6.

In formula (L3), $R^{L05}$ is a substituted or unsubstituted, $C_1$-$C_8$ straight, branched or cyclic alkyl group or a substituted or unsubstituted $C_6$-$C_{20}$ aryl group. Examples of the substituted or unsubstituted alkyl groups include straight, branched or cyclic ones such as methyl, ethyl, propyl, isopropyl, n-butyl, sec-butyl, tert-butyl, tert-amyl, n-pentyl, n-hexyl, cyclopentyl and cyclohexyl; and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Exemplary substituted or unsubstituted aryl groups are phenyl, methylphenyl, naphthyl, anthryl, phenanthryl, and pyrenyl. In formula (L3), m is 0 or 1, n is 0, 1, 2 or 3, and 2m+n is equal to 2 or 3.

In formula (L4), $R^{L06}$ is a substituted or unsubstituted, $C_1$-$C_8$ straight, branched or cyclic alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxy, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). In this case, each group participating in ring formation is a divalent $C_1$-$C_{15}$ hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

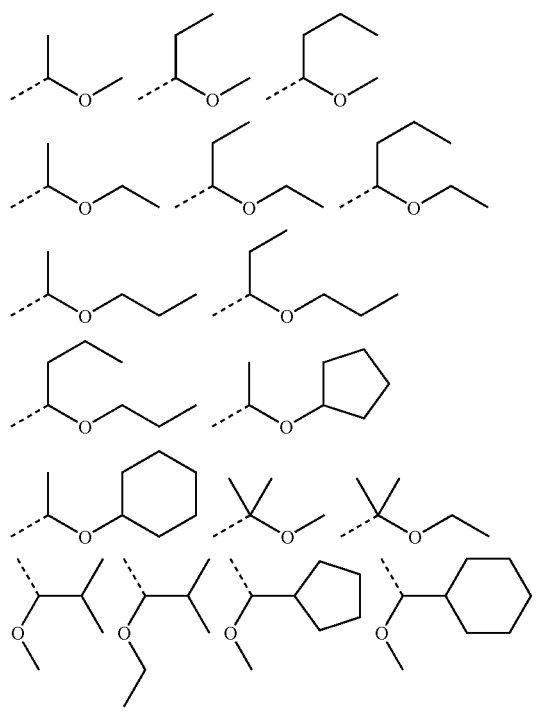

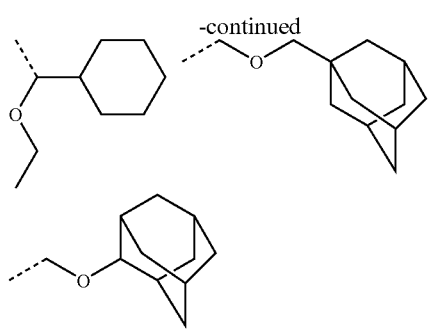

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

The acid labile groups of formula (L4) are preferably groups of the following formulae (L4-1) to (L4-4).

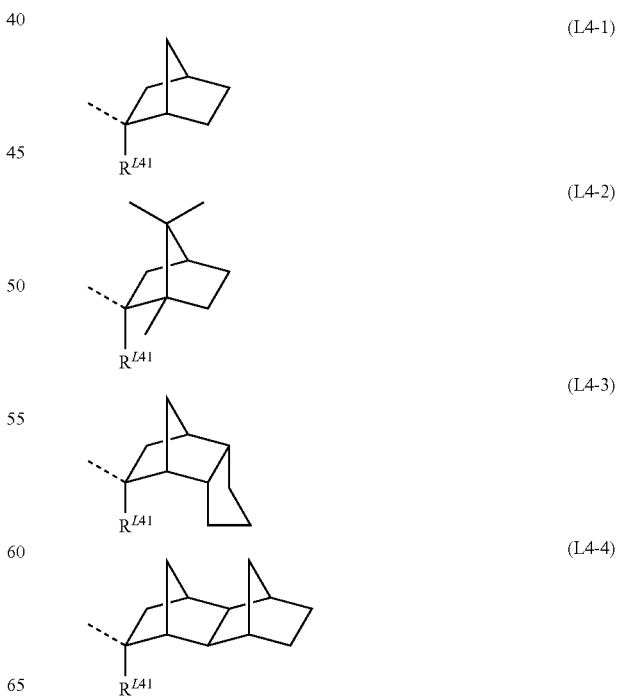

In formulae (L4-1) to (L4-4), the broken line indicates a bonding site and direction. $R^{L41}$ is each independently selected from monovalent hydrocarbon groups, typically straight, branched or cyclic $C_1$-$C_{10}$ alkyl groups, for example, methyl, ethyl, propyl, isopropyl, n-butyl, sec-butyl, tert-butyl, tert-amyl, n-pentyl, n-hexyl, cyclopentyl, and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

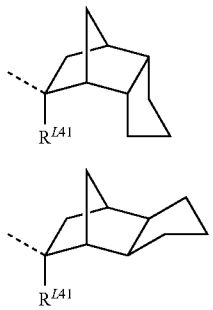

(L4-3-1)

(L4-3-2)

Similarly, the general formula (L4-4) represents one or a mixture of two or more selected from groups having the following general formulas (L4-4-1) to (L4-4-4).

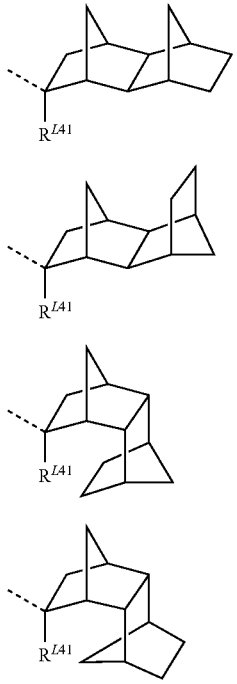

(L4-4-1)

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

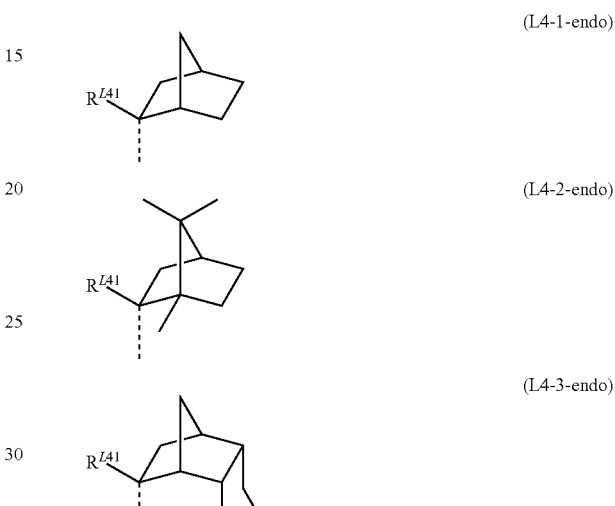

(L4-1-endo)

(L4-2-endo)

(L4-3-endo)

(L4-4-endo)

(See JP-A 2000-336121.)

Illustrative examples of the acid labile group of formula (L4) are given below.

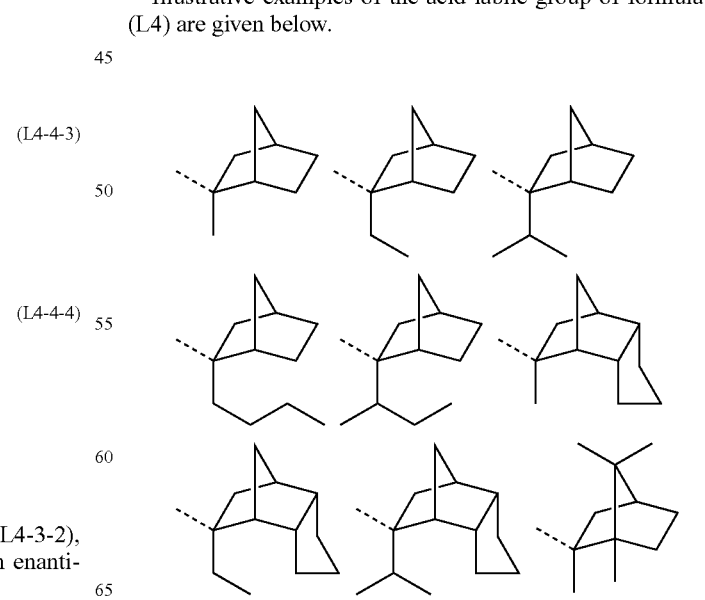

-continued
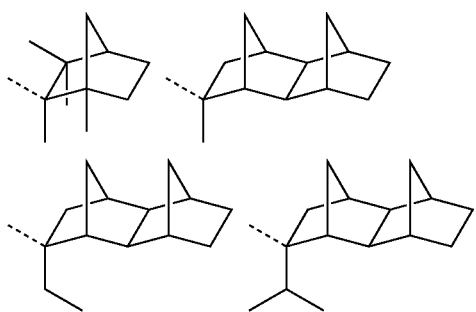
Examples of the tertiary $C_4$-$C_{20}$ alkyl, tri($C_1$-$C_6$-alkyl)silyl and $C_4$-$C_{20}$ oxoalkyl groups are as exemplified above for $R^{L04}$.
Illustrative, non-limiting examples of the recurring units of formula (3) are given below.
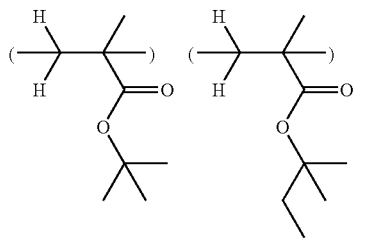
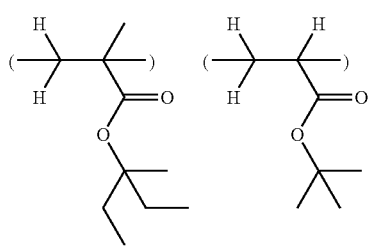
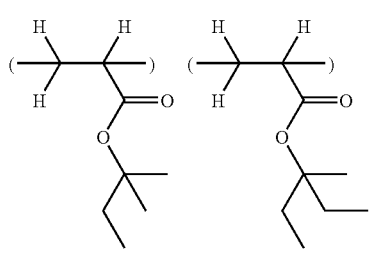
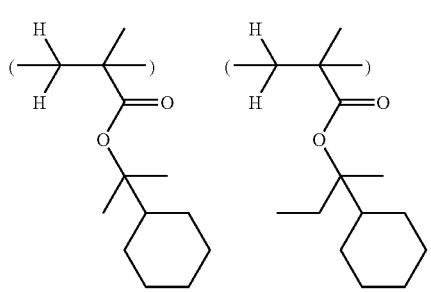
-continued
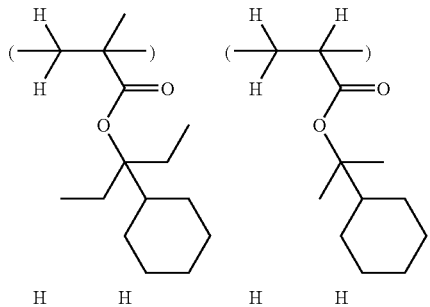
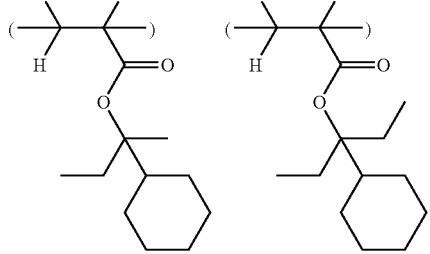
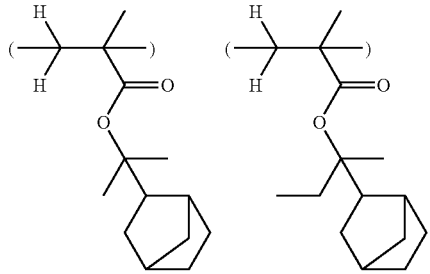
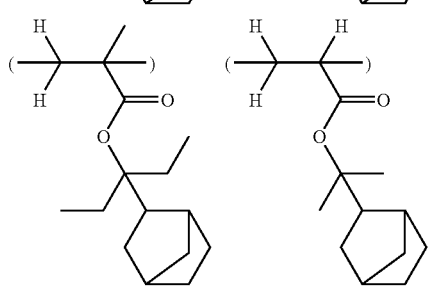
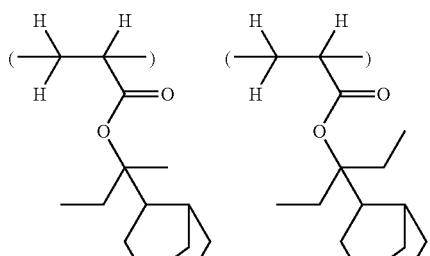
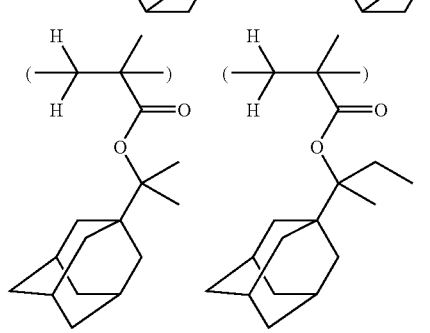

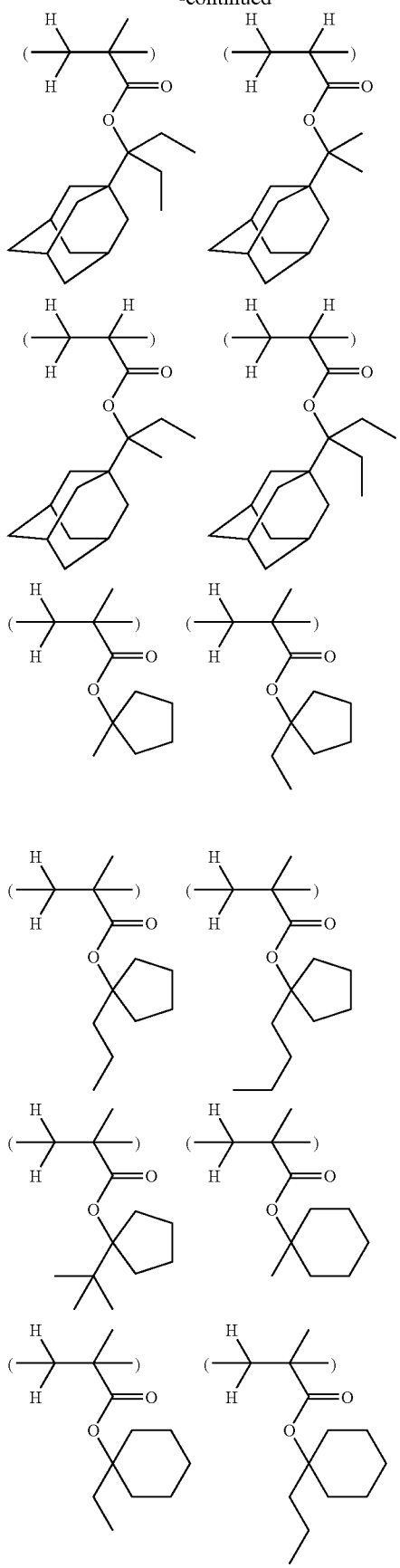
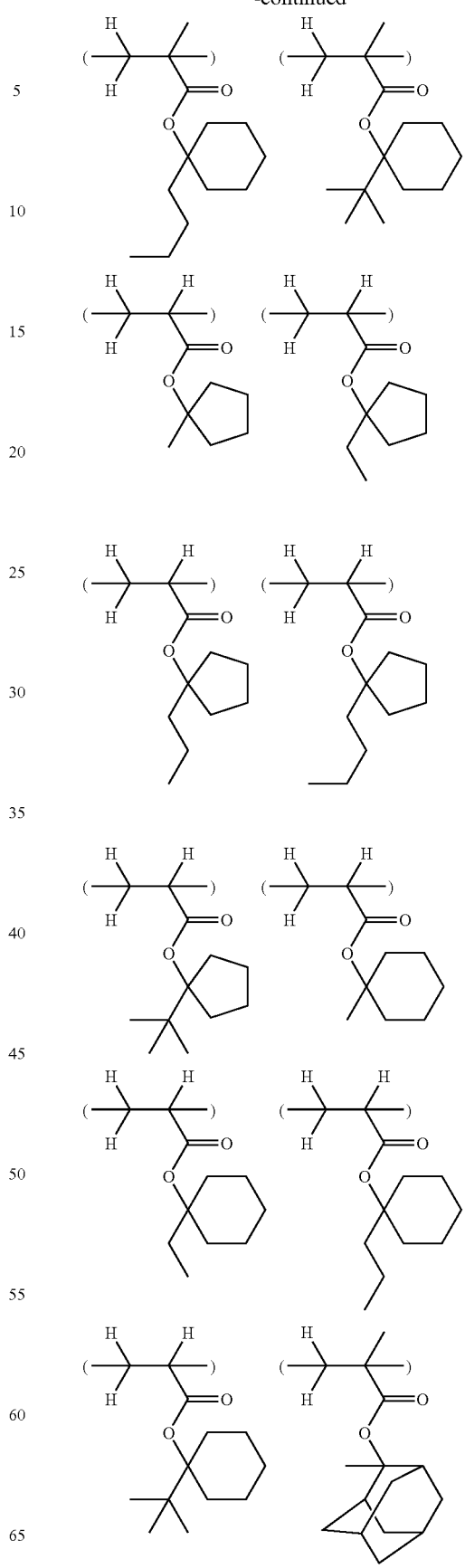

29
-continued
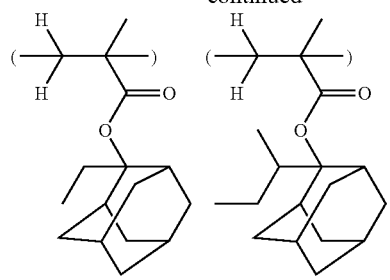
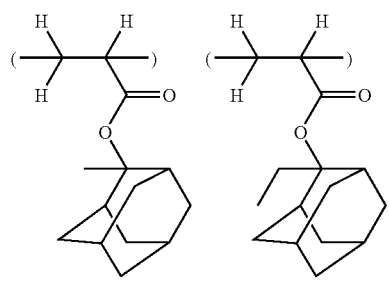
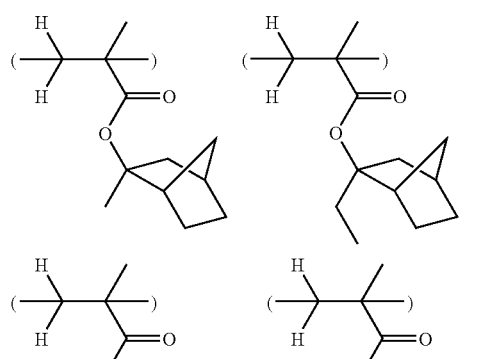
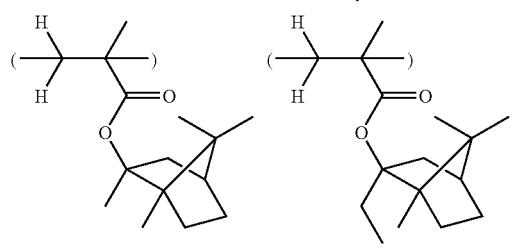
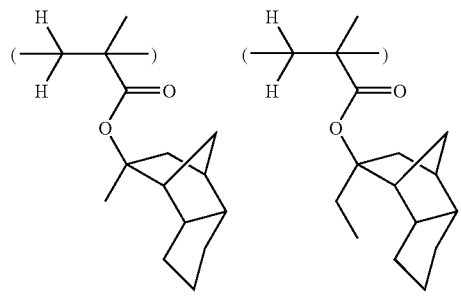
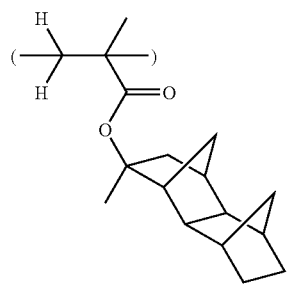
30
-continued
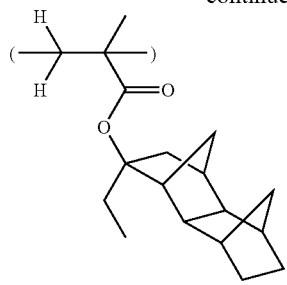
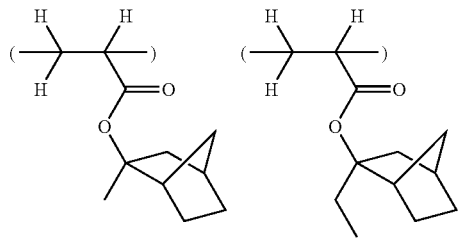
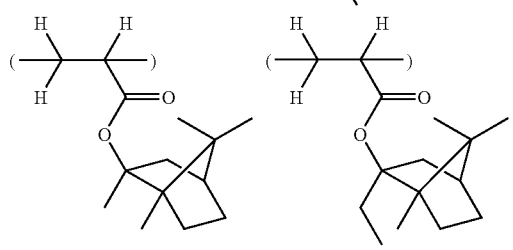
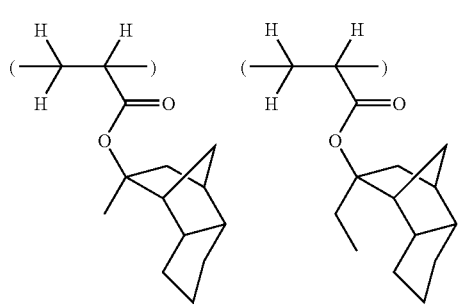
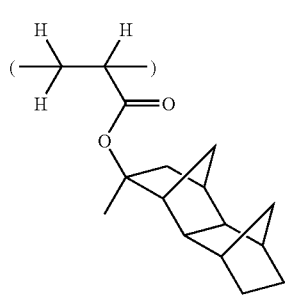
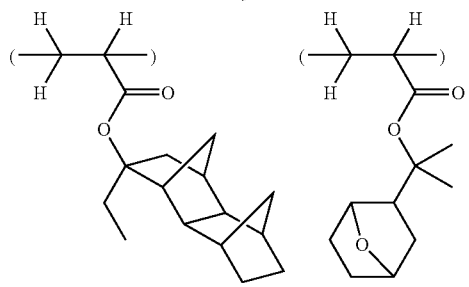

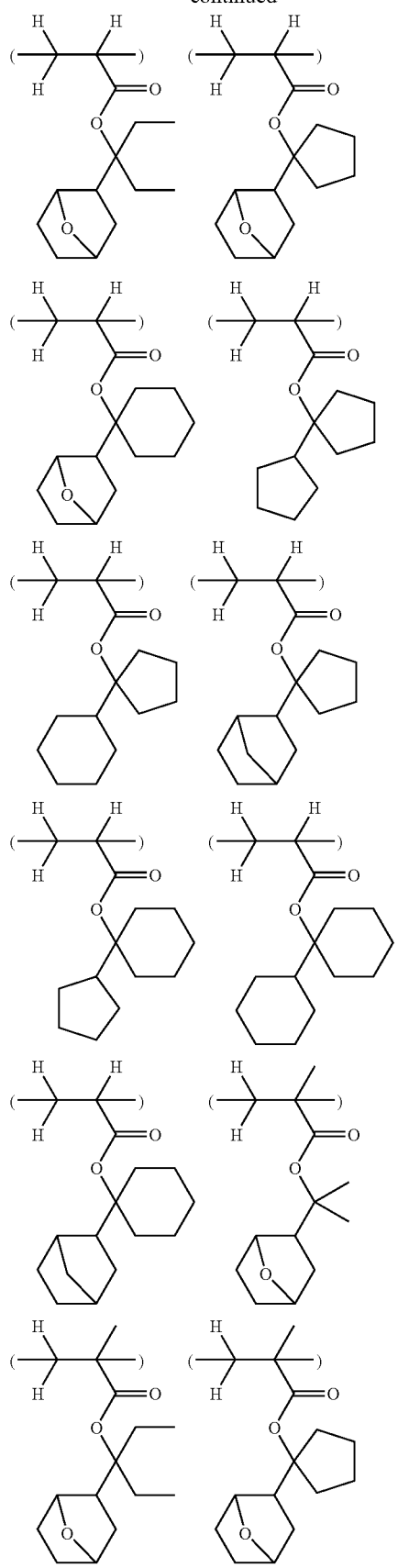
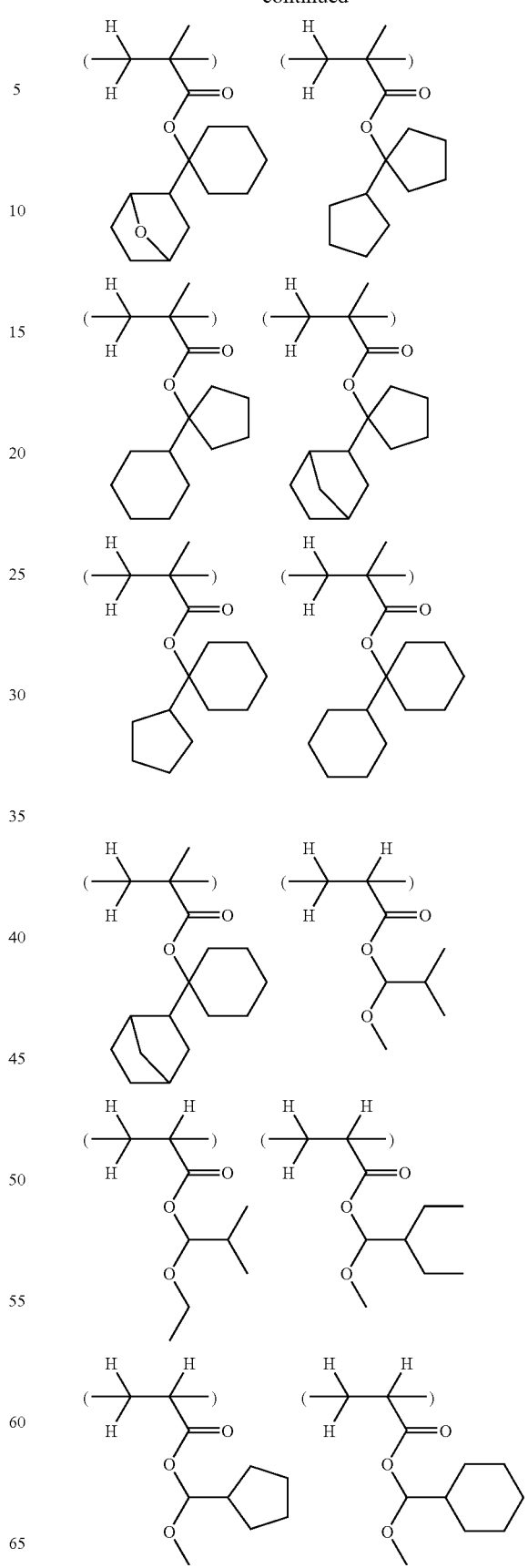

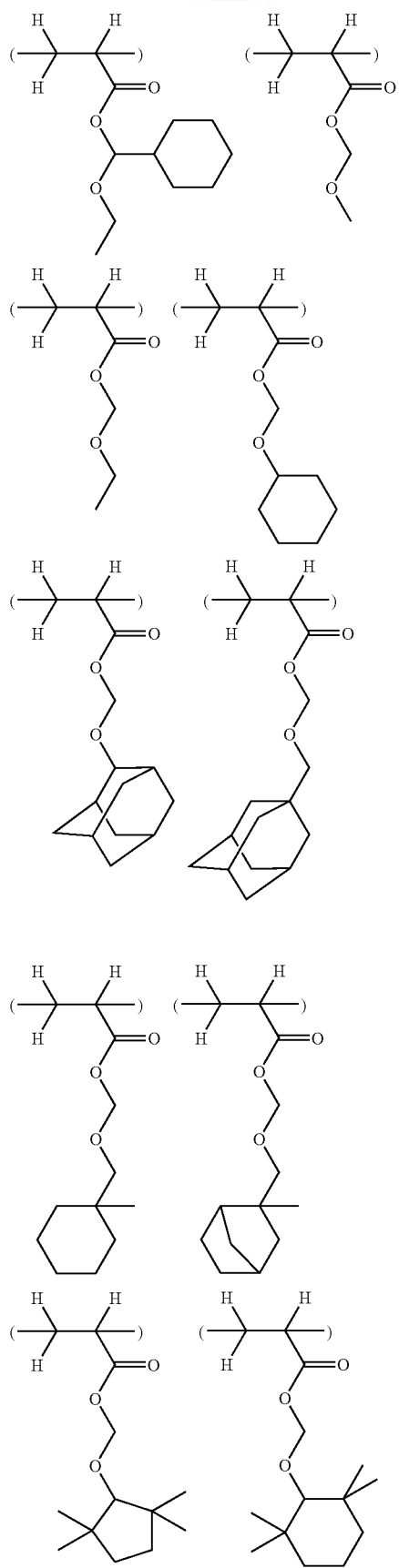
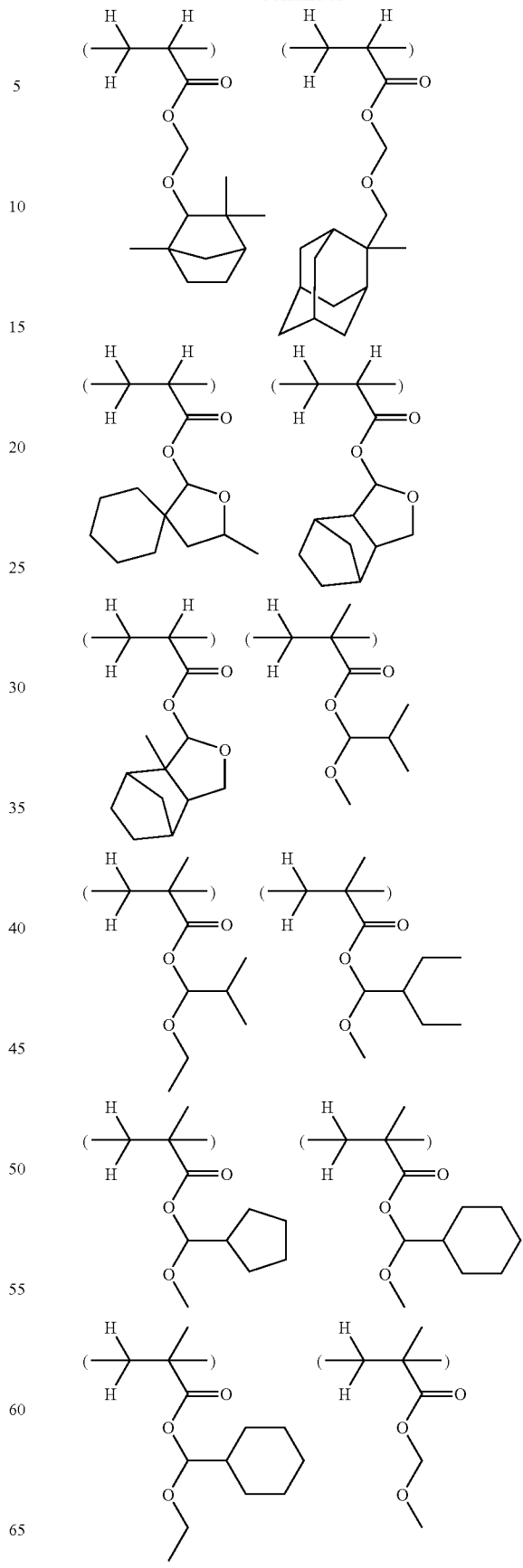

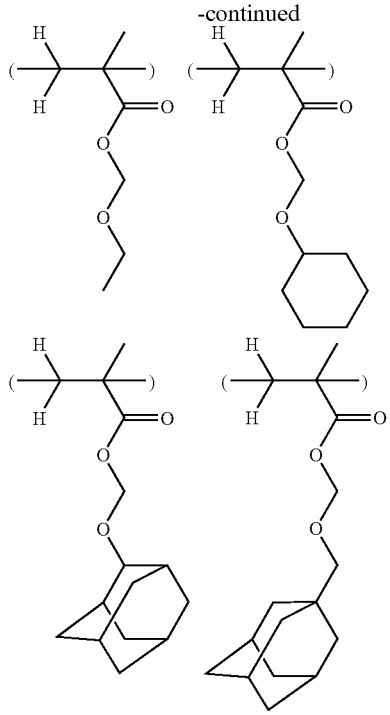
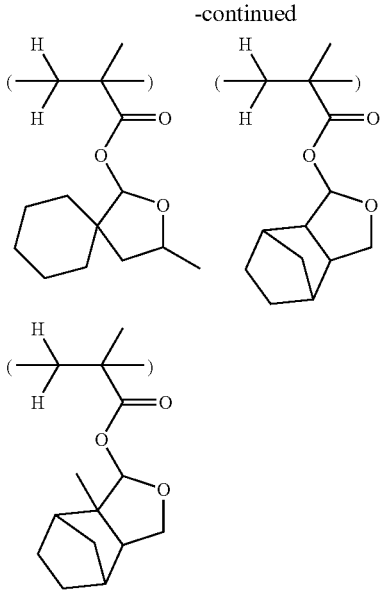
Illustrative, non-limiting examples of the recurring units of formula (4) are given below.
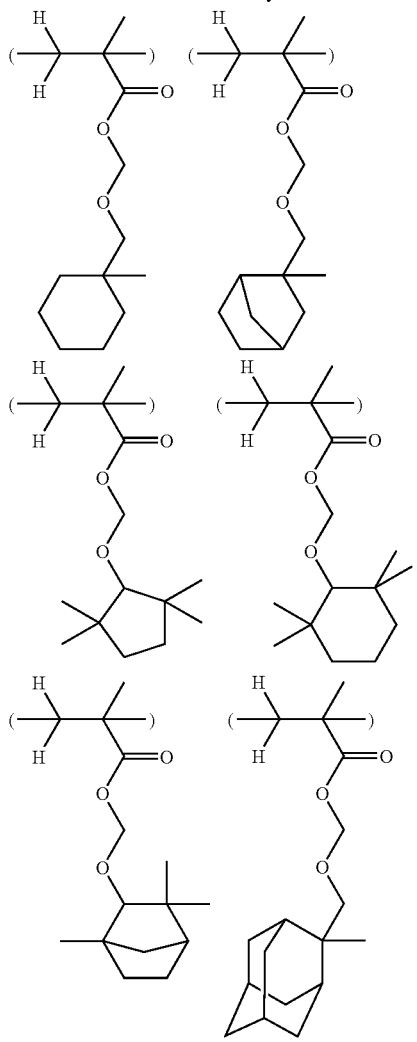
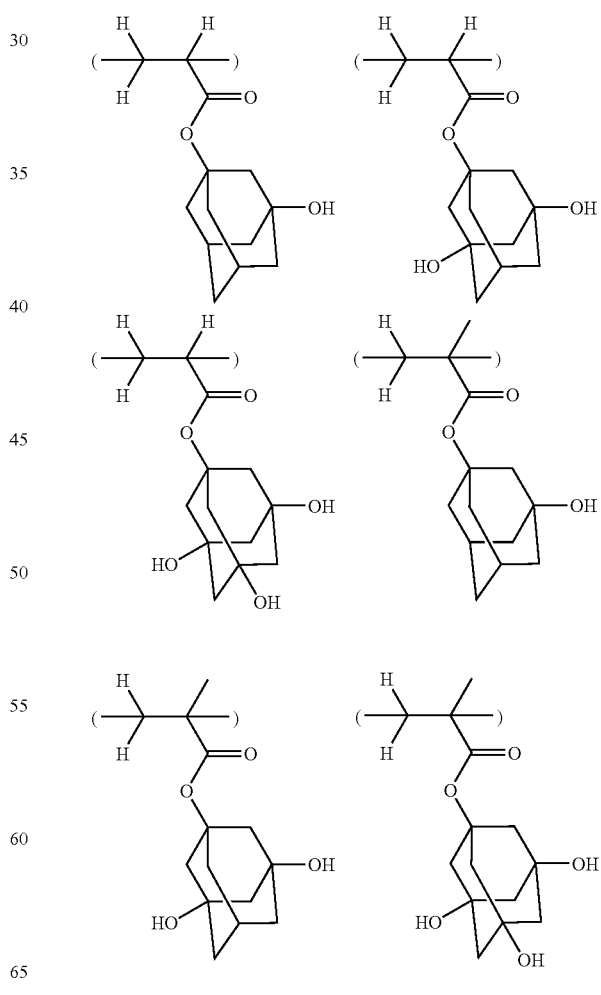

Illustrative, non-limiting examples of the recurring units of formula (5) are given below.
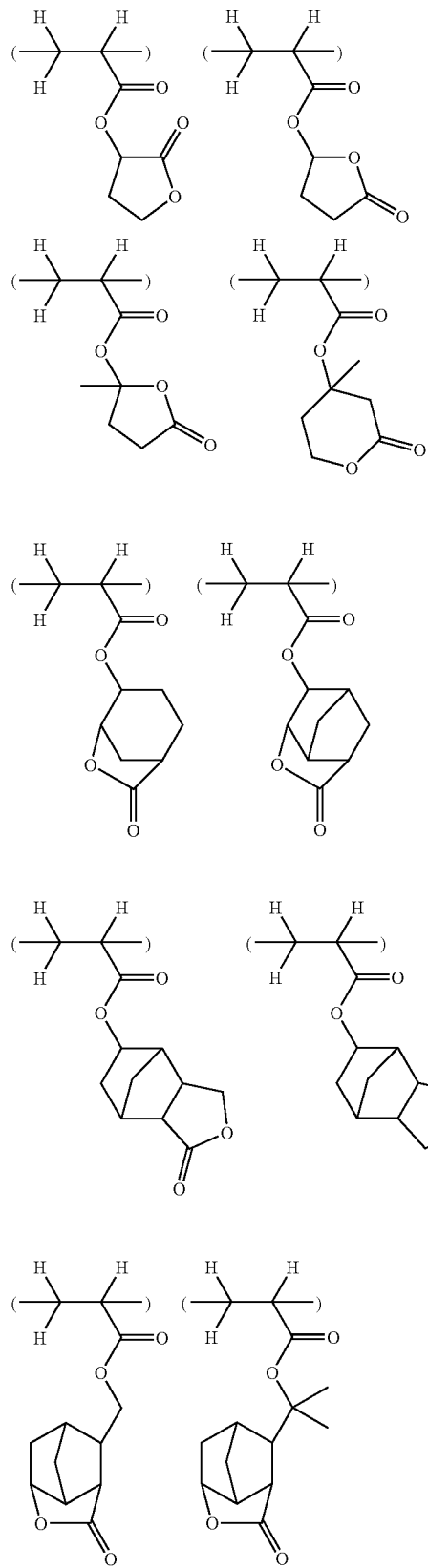
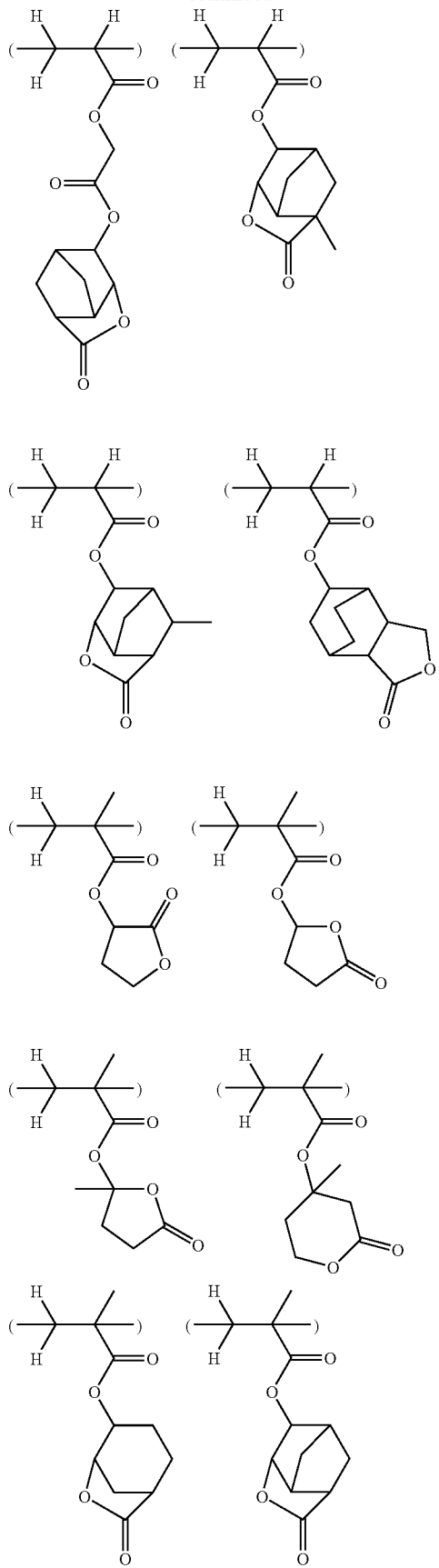

-continued
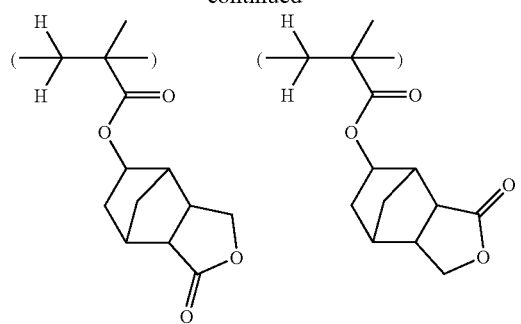
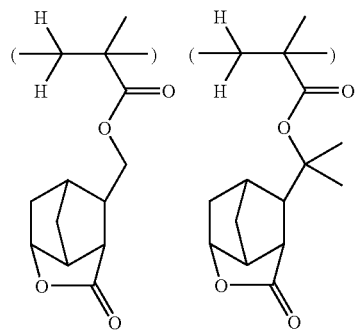
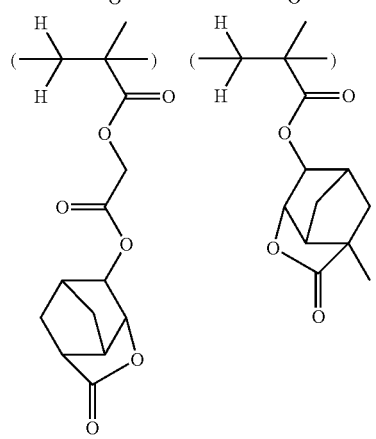
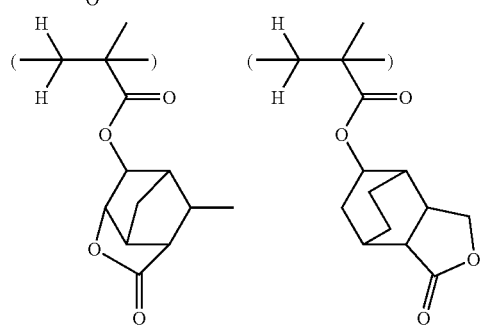
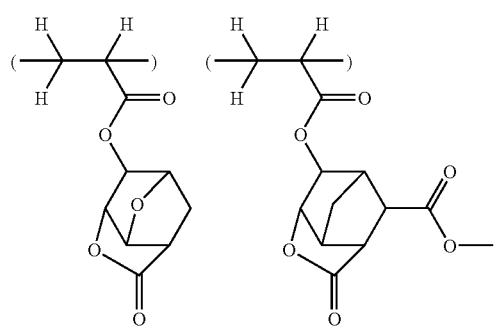
-continued
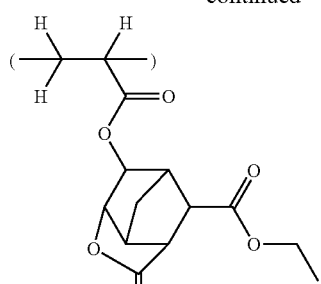
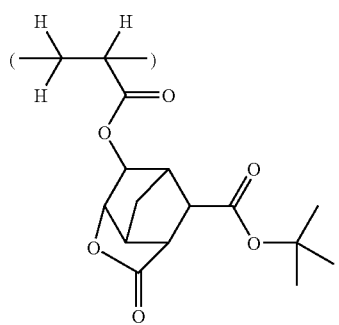
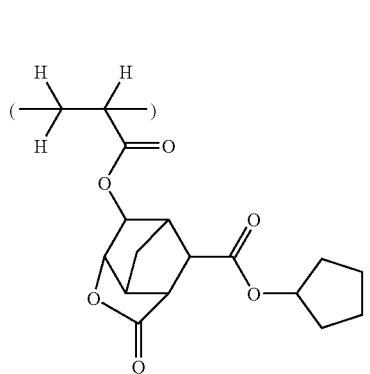
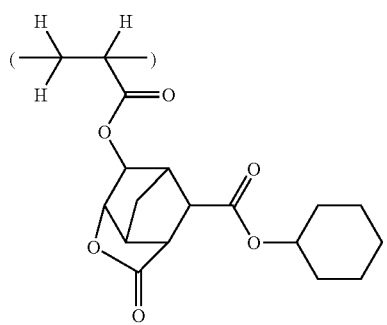
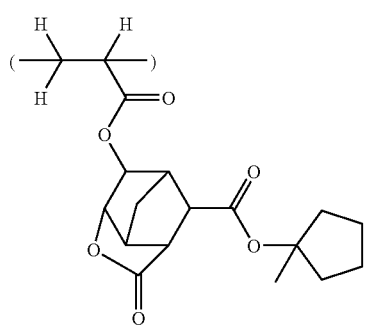

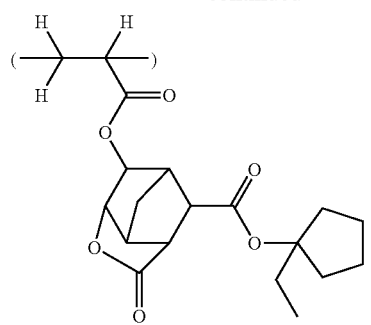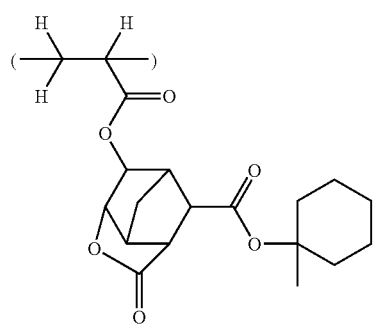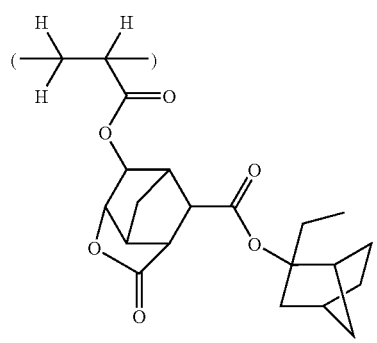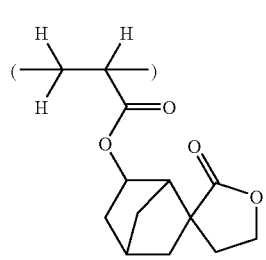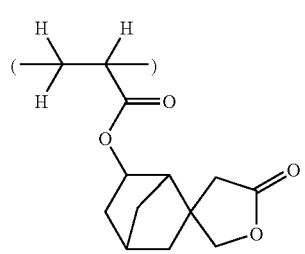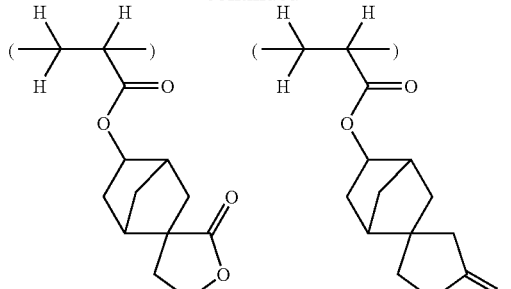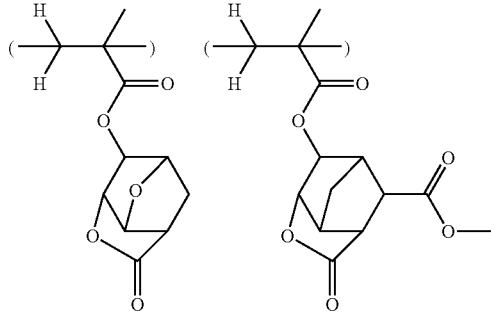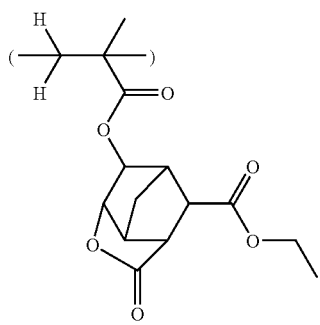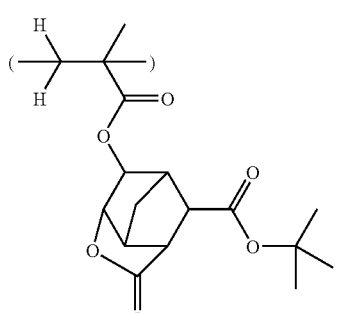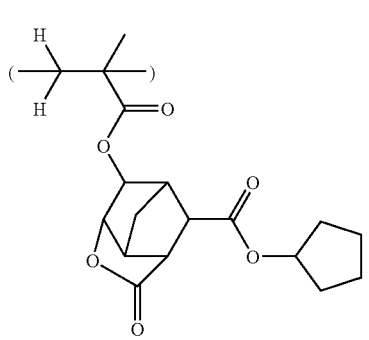

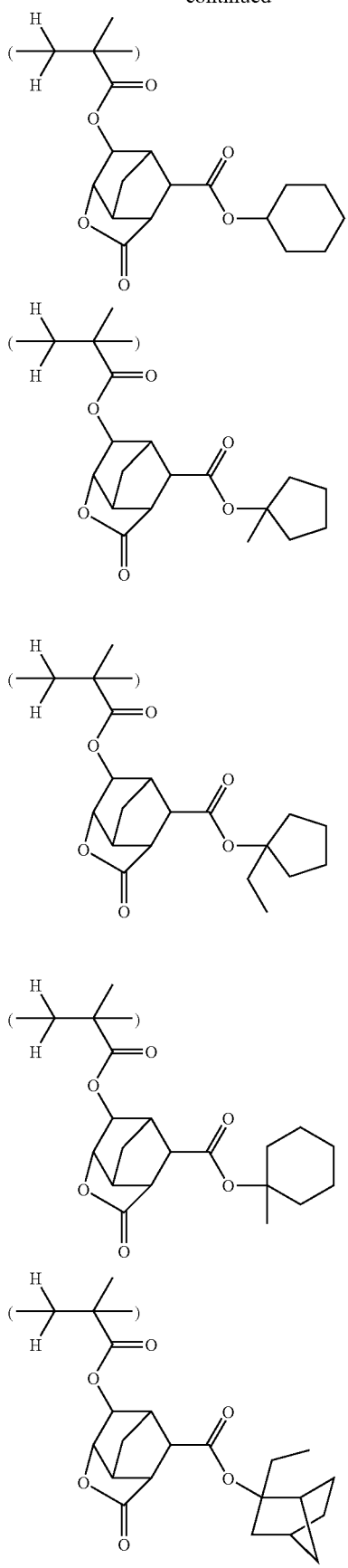
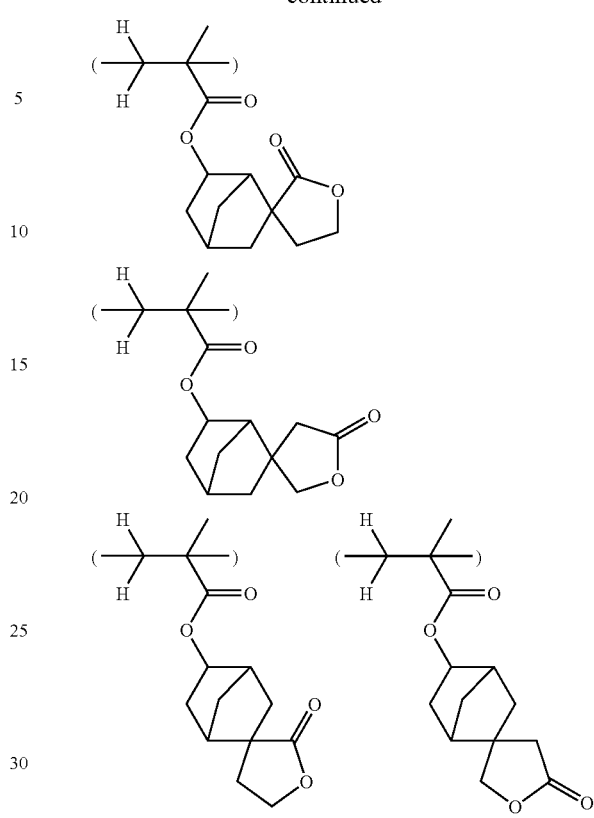
Illustrative, non-limiting examples of the recurring units of formula (6) are given below.
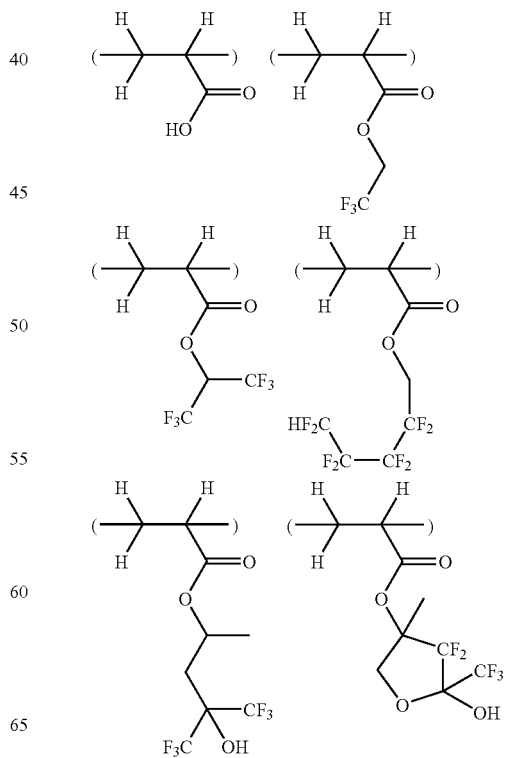

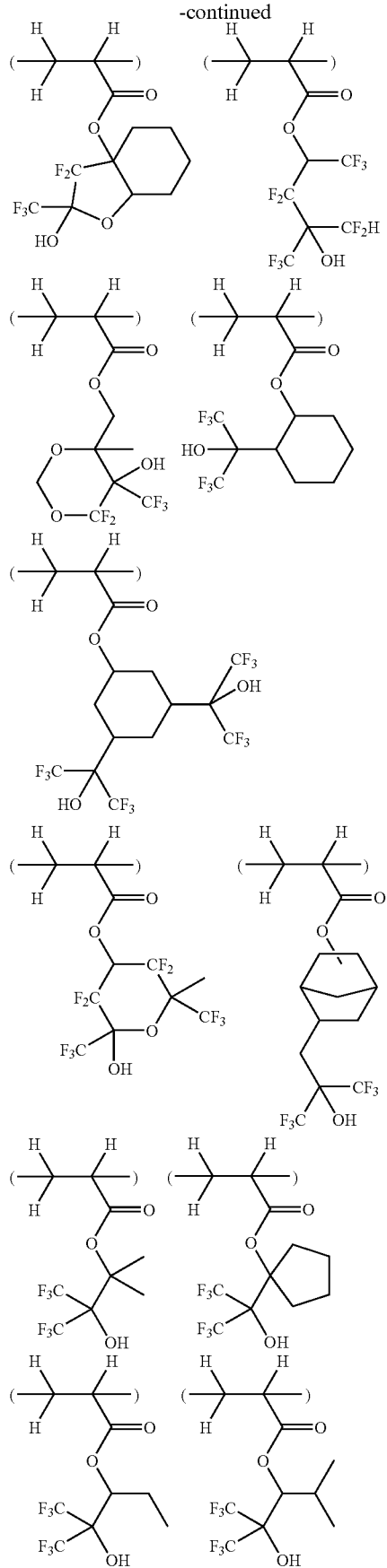
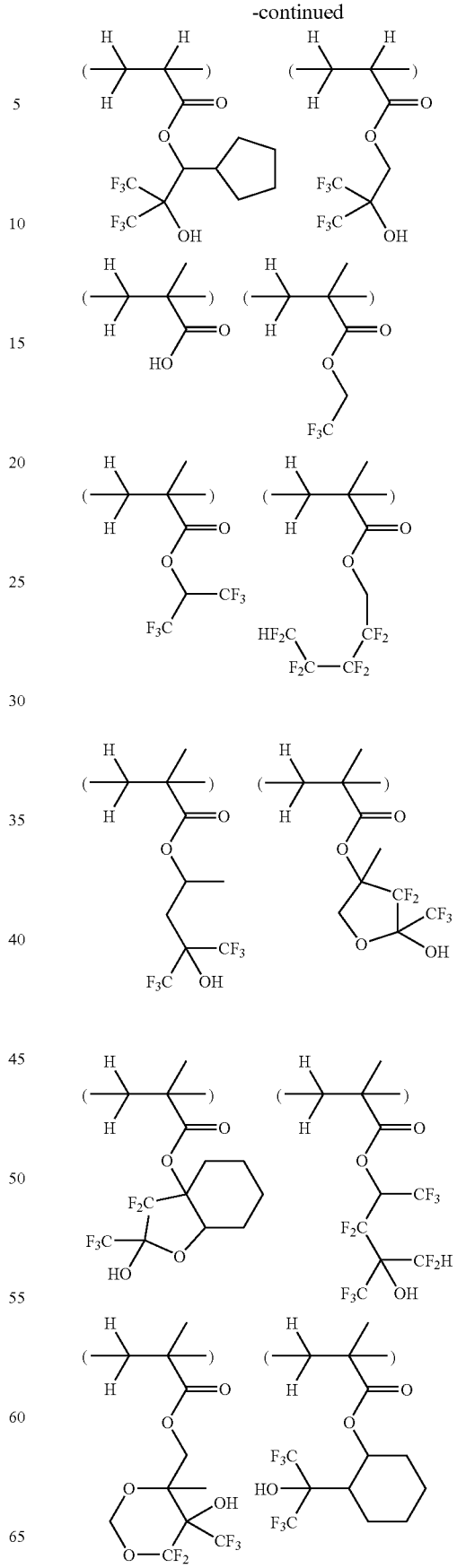

-continued

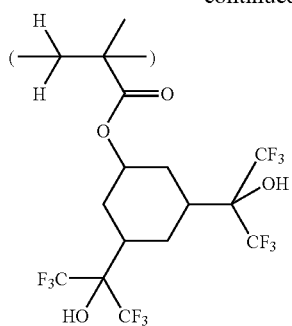

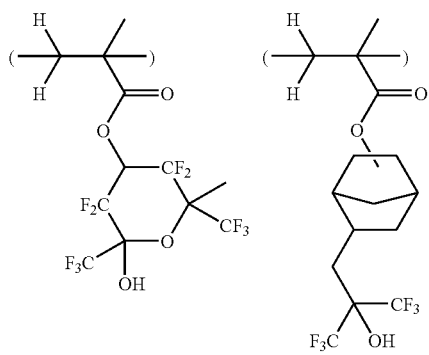

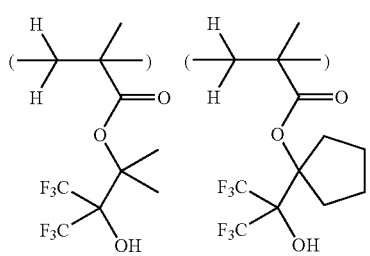

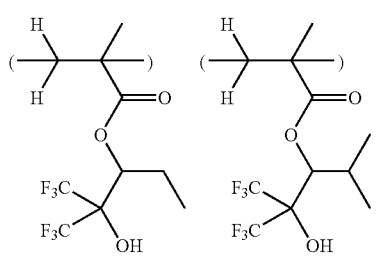

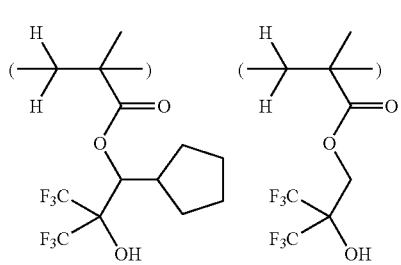

The polymer used in the resist composition of the invention may further comprise recurring units derived from another monomer having a carbon-to-carbon double bond other than the foregoing. Examples of the additional monomer include substituted acrylic acid esters such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, and tetracyclo[$6.2.1.1^{3,6}.0^{2,7}$] dodecene derivatives, and unsaturated acid anhydrides such as itaconic anhydride.

While the polymer used herein is applicable to the ArF lithography, it is also applicable to other lithography processes such as KrF, EB and EUV lithography.

In a further embodiment, the polymer used herein may comprise recurring units of at least one selected from the general formulae (7) to (9) and optionally, recurring units of at least one selected from the general formulae (3) to (6) described above.

(7)

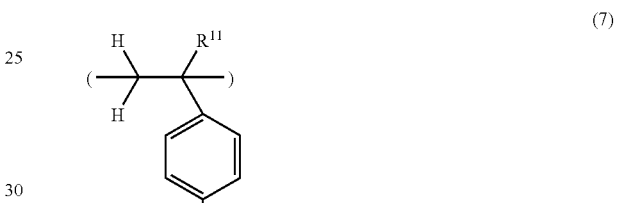

(8)

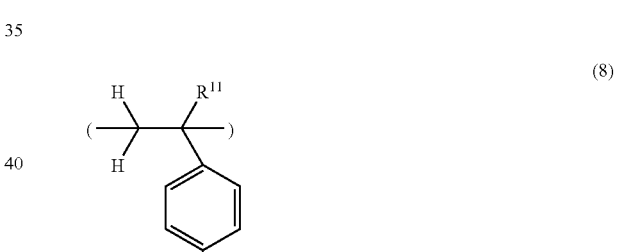

(9)

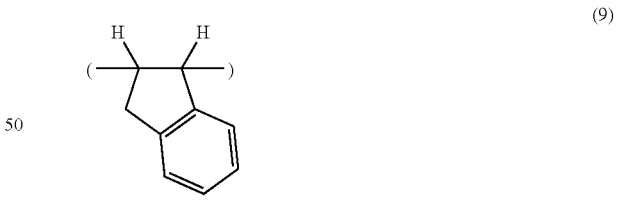

Herein, $R^{11}$ and XA are as defined above, and G is an oxygen atom or carboxyl group (—C(=O)O—).

Under the action of an acid, a polymer comprising recurring units of formula (7) is decomposed to generate a phenolic hydroxyl group and/or carboxylic acid and turns into an alkali-soluble polymer. The acid labile groups represented by XA may be selected from a variety of such groups, for example, groups of the general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms, which are described above.

Illustrative, non-limiting examples of the recurring units of formula (7) are given below.

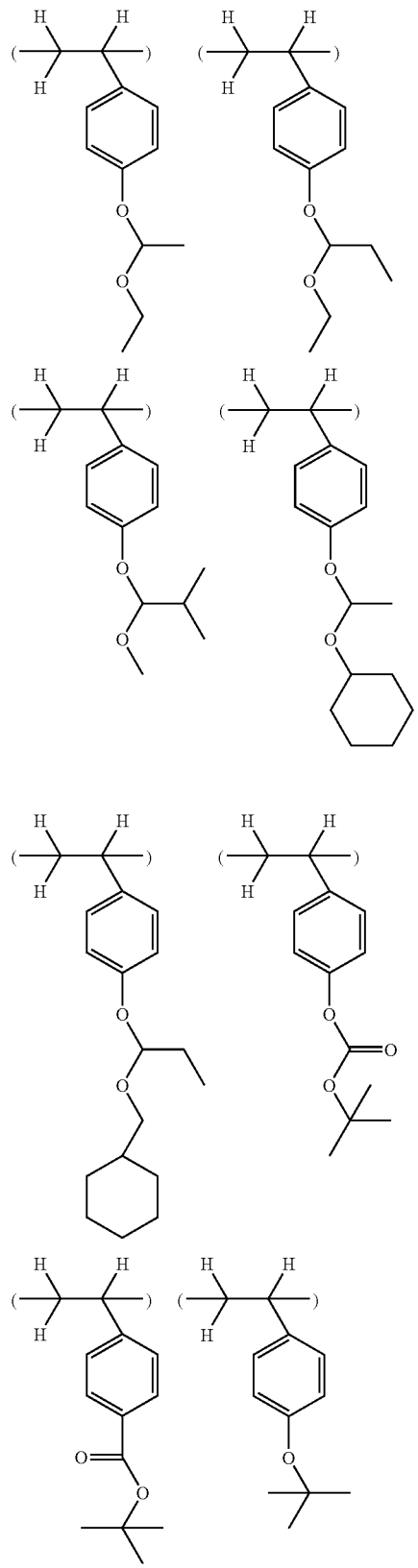

When the polymer contains recurring units having formulae (3) to (6) in addition to the recurring units of at least one type having formulae (7) to (9), the inclusion of recurring units having formula (3) is preferred.

The polymer comprising recurring units of at least one type selected from formulae (7) to (9) may further comprise recurring units derived from another monomer having a carbon-to-carbon double bond other than the foregoing. Examples of the additional monomer include substituted acrylic acid esters such as methyl methacrylate, methyl crotonate, dimethyl maleate, and dimethyl itaconate, unsaturated carboxylic acids such as maleic acid, fumaric acid and itaconic acid, cyclic olefins such as norbornene, norbornene derivatives, tetracyclo[6.2.1.1$^{3,6}$.0$^{2,7}$]dodecene derivatives, and norbornadienes, and unsaturated acid anhydrides such as itaconic anhydride, as well as styrene, acenaphthylene, vinylnaphthalene, hydroxyvinylnaphthalene, and other monomers.

It is noted that the polymer used herein may have a weight average molecular weight (Mw) of 1,000 to 500,000, and preferably 3,000 to 100,000. Outside the range, a polymer may suffer an extreme drop of etching resistance or a reduced resolution due to a failure to provide a difference in dissolution rate before and after exposure. The measurement of molecular weight may be performed by gel permeation chromatography (GPC) versus polystyrene standards or a light scattering method.

In the polymer used herein, the preferred proportion of respective recurring units derived from discrete monomers may fall, for example, in the range (mol %) shown below, but is not limited thereto. The polymer may consist essentially of (I) from more than 1 mol % to 50 mol %, preferably 5 to 40 mol %, and more preferably 10 to 30 mol % of constituent units of one or more type having formula (3) and/or (7); (II) from 50 mol % to 99 mol %, preferably 60 to 95 mol %, and more preferably 70 to 90 mol % of constituent units of one or more type selected from formulae (4) to (6) and/or formulae (8) to (9); and optionally, (III) from 0 mol % to 80 mol %, preferably 0 to 70 mol %, and more preferably 0 to 50 mol % of constituent units of one or more type derived from the additional monomer(s).

The polymer used herein may be prepared through copolymerization reaction of selected monomers. While various modes of copolymerization reaction may be used, the preferred modes are radical polymerization, anionic polymerization and coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

The polymer prepared by any mode of polymerization as described above may be used in a negative resist composition, provided that some or all acid labile groups on the polymer are deprotected. Alternatively, the polymer in which acid labile groups have been deprotected can be modified by introducing acid labile groups therein again whereby substituent groups different from the acid labile groups initially introduced during polymerization are introduced into the polymer.

For example, once a polymer is formed through radical polymerization of 4-ethoxyethoxystyrene, ethoxyethoxy groups are eliminated from the polymer using acetic acid, pyridinium tosylate or the like, whereupon the polymer may be converted into a copolymer with polyhydroxystyrene. The resultant copolymer may be used as a base resin in a negative resist composition. Alternatively, hydroxystyrene units in the resultant copolymer may be reacted with di-tert-butyl dicarbonate, tert-butyl chloroacetate, vinyl ethers or the like, whereby acid labile groups different from the acid labile groups (i.e., ethoxyethoxy groups) initially introduced during polymerization are introduced.

Hydrogenated products of ring-opening metathesis polymers (ROMP) may be synthesized by the method described in Examples of JP-A 2003-66612. Examples of such hydrogenated polymers include, but are not limited to, the following combinations of recurring units.

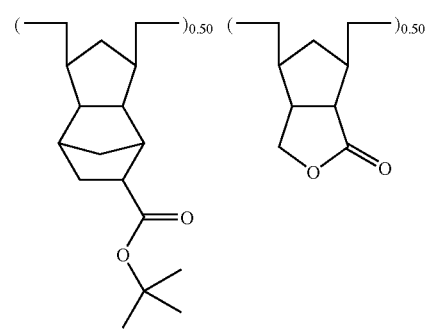

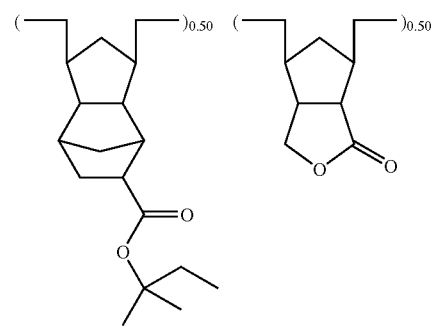

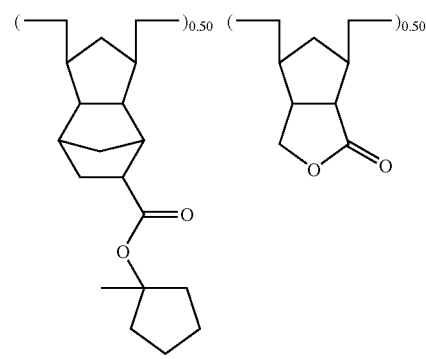

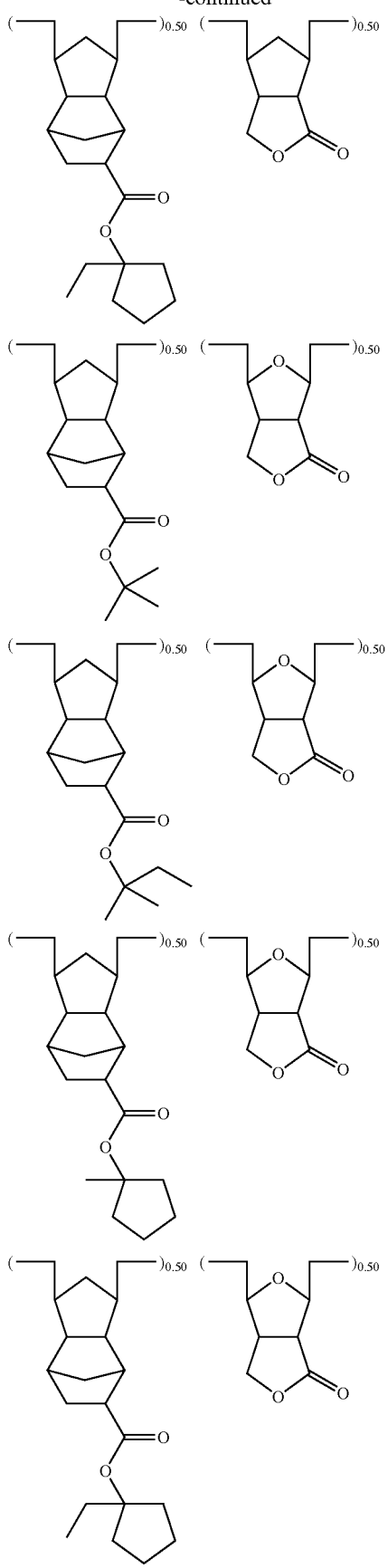
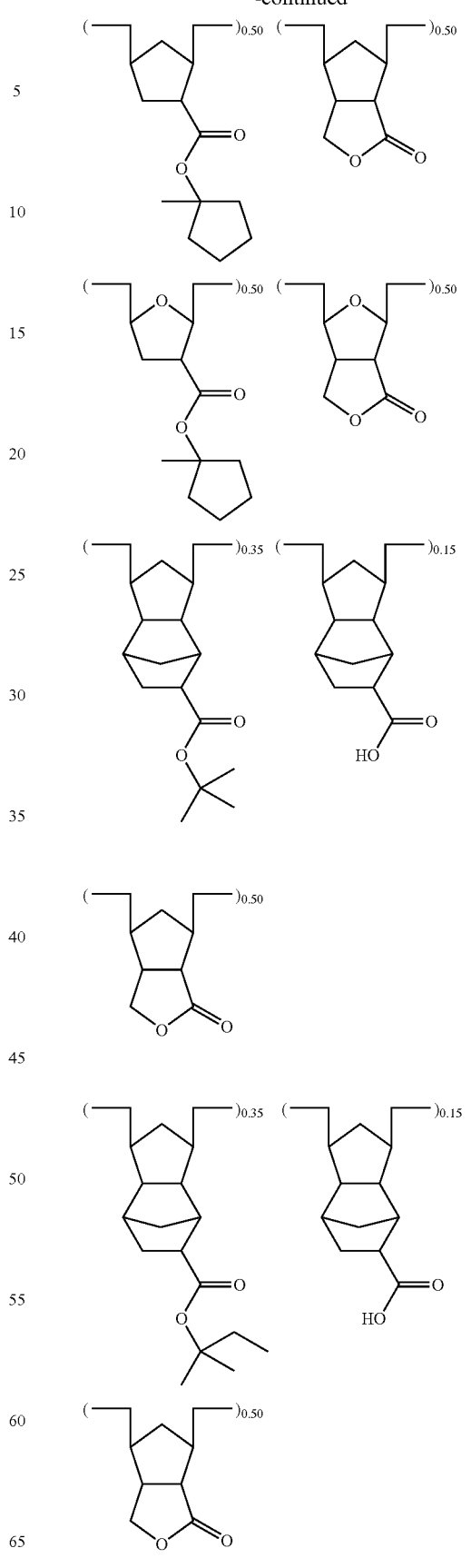

55
-continued
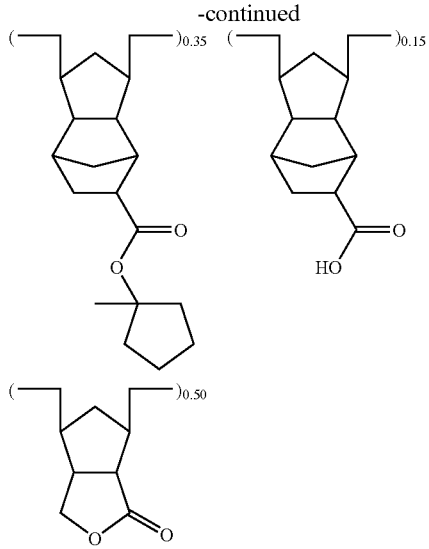
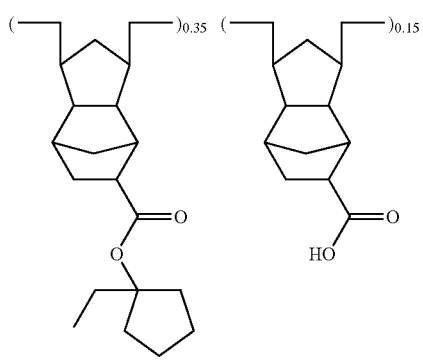
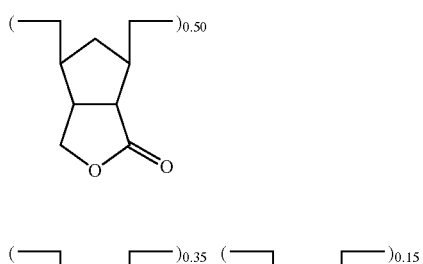
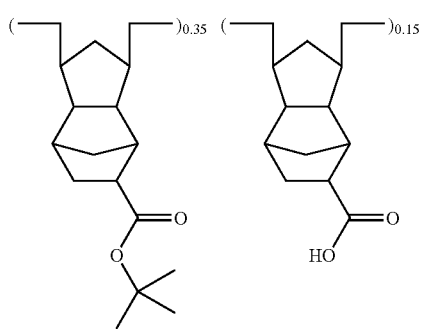
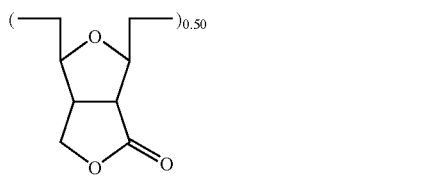
56
-continued
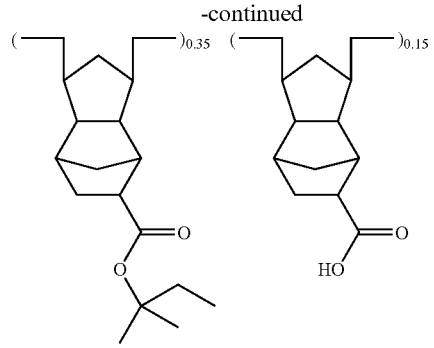
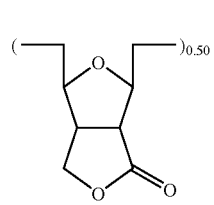
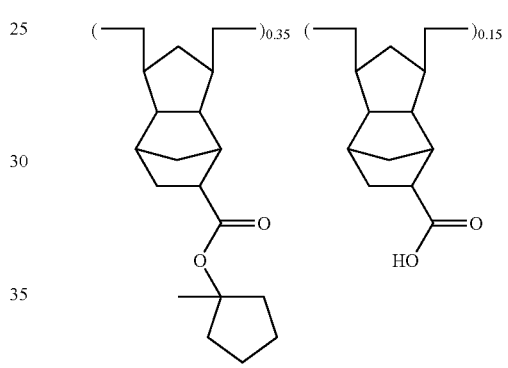
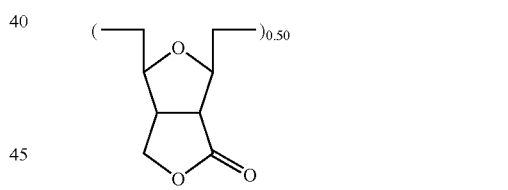
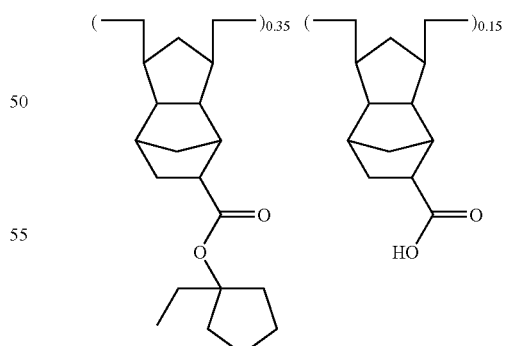
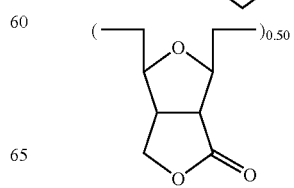

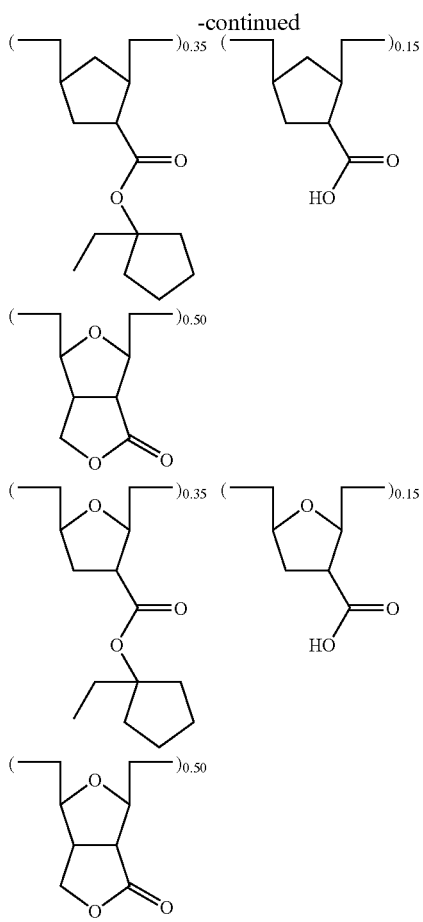

In the resist composition, the polymers may be added alone or in admixture of two or more. The use of plural polymers allows for easy adjustment of resist properties.

Component D

A quencher (D) may be optionally used in the resist composition of the invention. The term "quencher" as used herein has a meaning generally known in the art and refers to a compound capable of suppressing the rate of diffusion when the acid generated by the acid generator diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N'-dimethylmethylenediamine, N,N'-dimethylethylenediamine, and dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, N,N-bis(hydroxyethyl)aniline, 2-methylaniline, 3-methylaniline, 4-methylaniline, ethylaniline, propylaniline, dimethylaniline, 2,6-diisopropylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, 4-methyl-2-phenylimidazole, and 2-phenylbenzimidazole), pyrazole derivatives, furazane derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds with carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Suitable nitrogen-containing compounds with sulfonyl group include 3-pyridinesulfonic acid and pyridinium p-toluenesulfonate. Examples of suitable nitrogen-containing compounds with hydroxyl group, nitrogen-containing compounds with hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl) morpholine, 2-(2-hydroxyethyl)pyridine, 1-(2-hydroxyethyl)piperazine, 1-[2-(2-hydroxyethoxy)ethyl] piperazine, piperidine ethanol, 1-(2-hydroxyethyl) pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide. Suitable carbamate derivatives include N-tert-butoxycarbonyl-N,N-dicyclohexylamine, N-tert-butoxycarbonylbenzimidazole, and oxazolidinone.

Suitable ammonium salts include pyridinium p-toluenesulfonate, triethylammonium p-toluenesulfonate, trioctylammonium p-toluenesulfonate, triethylammonium 2,4,6-triisopropylbenzenesulfonate, trioctylammonium 2,4,6-triisopropylbenzenesulfonate, triethylammonium camphorsulfonate, trioctylammonium camphorsulfonate, tetramethylammonium hydroxide, tetraethylammonium hydroxide, tetrabutylammonium hydroxide, benzyltrimethylammonium hydroxide, tetramethylammonium p-toluenesulfonate, tetrabutylammonium p-toluenesulfonate, benzyltrimethylammonium p-toluenesulfonate, tetramethylammonium camphorsulfonate, tetrabutylammonium camphorsulfonate, benzyltrimethylammonium camphorsulfonate, tetramethylammonium 2,4,6-triisopropylbenzenesulfonate, tetrabutylammonium 2,4,6-triisopropylbenzenesulfonate, benzyltrimethylammonium 2,4,6-triisopropylbenzenesulfonate, tetramethylammonium acetate, tetrabutylammonium acetate, benzyltrimethylammonium acetate, tetramethylammonium benzoate, tetrabutylammonium benzoate, and benzyltrimethylammonium benzoate.

Amine compounds of the following general formula (Am-1) may also be added.

$$N(RX)_k(Ry)_{3-k} \quad (Am-1)$$

In the formula, k is equal to 1, 2 or 3. The side chain Rx is independently selected from groups of the following general formulas (Rx-1) to (Rx-3). The side chain Ry is independently hydrogen or a straight, branched or cyclic $C_1$-$C_{20}$ alkyl group in which some or all hydrogen atoms may be substituted by fluorine atoms and which may contain an ether or hydroxyl group. Two or three Rx may bond together to form a ring.

(Rx-1)

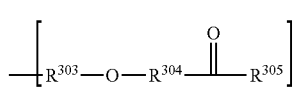
(Rx-2)

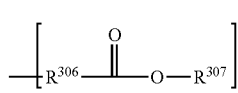
(Rx-3)

Herein $R^{301}$, $R^{303}$ and $R^{306}$ are independently straight or branched $C_1$-$C_4$ alkylene groups; $R^{302}$ and $R^{305}$ are independently hydrogen or straight, branched or cyclic $C_1$-$C_{20}$ alkyl groups in which some or all hydrogen atoms may be substituted by fluorine atoms and which may contain one or more hydroxyl group, ether group, ester group or lactone ring; $R^{304}$ is a single bond or a straight or branched $C_1$-$C_4$ alkylene group; $R^{307}$ is a straight, branched or cyclic $C_1$-$C_{20}$ alkyl group in which some or all hydrogen atoms may be substituted by fluorine atoms and which may contain one or more hydroxyl group, ether group, ester group or lactone ring.

Illustrative examples of suitable compounds having formula (Am-1) include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl) amine, tris(2-valeryloxyethyl)amine, tris(2-pivaloyloxyethyl)amine, N,N-bis(2-acetoxyethyl)-2-(acetoxyacetoxy) ethylamine, tris(2-methoxycarbonyloxyethyl)amine, tris(2-tert-butoxycarbonyloxyethyl)amine, tris[2-(2-oxopropoxy) ethyl]amine, tris[2-(methoxycarbonylmethyl)oxyethyl] amine, tris[2-(tert-butoxycarbonylmethyloxy)ethyl]amine, tris[2-(cyclohexyloxycarbonylmethyloxy)ethyl]amine, tris (2-methoxycarbonylethyl)amine, tris(2-ethoxycarbonylethyl)amine, N,N-bis(2-hydroxyethyl)-2-(methoxycarbonyl) ethylamine, N,N-bis(2-acetoxyethyl)-2-(methoxycarbonyl) ethylamine, N,N-bis(2-hydroxyethyl)-2-(ethoxycarbonyl) ethylamine, N,N-bis(2-acetoxyethyl)-2-(ethoxycarbonyl) ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl) ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl] ethylamine, N,N-bis(2-acetoxyethyl)-2-[(2-oxotetrahydrofuran-3-yl)oxy-carbonyl]ethylamine, N,N-bis (2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butylbis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis(methoxycarbonylmethyl)amine, N-hexylbis(methoxycarbonylmethyl)amine, and β-(diethylamino)-δ-valerolactone.

Also useful are one or more cyclic structure-bearing amine compounds having the following general formula (Am-2).

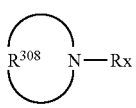
(Am-2)

Herein Rx is as defined above, and $R^{308}$ is a straight or branched $C_2$-$C_{20}$ alkylene group in which some or all hydrogen atoms may be substituted by fluorine atoms and which may contain one or more carbonyl, ether, ester or sulfide groups.

Illustrative examples of the cyclic structure-bearing amine compounds having formula (Am-2) include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-[2-(2-methoxyethoxy)ethoxy]ethylmorpholine, 2-[2-(2-butoxyethoxy)ethoxy]ethylmorpholine, 2-{2-[2-(2-methoxyethoxy)ethoxy]ethoxy}ethylmorpholine, 2-{2-[2-(2-butoxyethoxy)ethoxy]ethoxy}ethylmorpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, 2-morpholinoethyl cyclohexanecarboxylate, and 2-morpholinoethyl adamantanecarboxylate.

Also, one or more cyano-bearing amine compounds having the following general formulae (Am-3) to (Am-6) may be added.

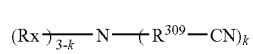
(Am-3)

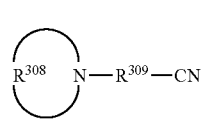
(Am-4)

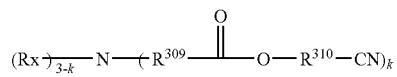
(Am-5)

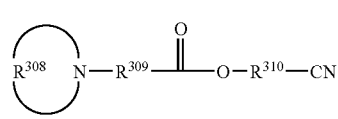
(Am-6)

Herein, Rx, $R^{308}$ and k are as defined in formula (Am-1), and $R^{309}$ and $R^{310}$ are each independently a straight or branched $C_1$-$C_4$ alkylene group.

Illustrative examples of the cyano-bearing amine compounds include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropanoate, methyl N-(2-cyanoethyl)-N-(2-hydroxyethyl)-3-aminopropanoate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropanoate, methyl N-cyanomethyl-N-(2-hydroxyethyl)-3-aminopropanoate, methyl N-(2-acetoxyethyl)-N-cyanomethyl-3-aminopropanoate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are amine compounds of imidazole structure having a polar functional group, represented by the general formula (Am-7).

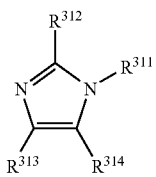

(Am-7)

Herein, $R^{311}$ is a straight, branched or cyclic $C_2$-$C_{20}$ alkyl group in which some or all hydrogen atoms may be substituted by fluorine atoms and which has one or more polar functional groups. The polar functional group is selected from among hydroxyl, carbonyl, ester, ether, sulfide, carbonate, cyano and acetal groups and mixtures thereof. $R^{312}$, $R^{313}$ and $R^{314}$ are each independently a hydrogen atom, a straight, branched or cyclic $C_1$-$C_{10}$ alkyl group, aryl group or aralkyl group.

Also included are amine compounds of benzimidazole structure having a polar functional group, represented by the general formula (Am-8).

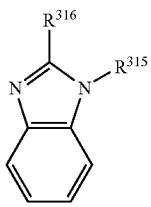

(Am-8)

Herein, $R^{315}$ is a straight, branched or cyclic $C_1$-$C_{20}$ alkyl group in which some or all hydrogen atoms may be substituted by fluorine atoms and which has one or more polar functional groups. The alkyl group contains as the polar functional group at least one group selected from among ester, acetal and cyano groups, and may additionally contain at least one group selected from among hydroxyl, carbonyl, ether, sulfide and carbonate groups. $R^{316}$ is a hydrogen atom, a straight, branched or cyclic $C_1$-$C_{10}$ alkyl group, aryl group or aralkyl group.

Further included are heterocyclic nitrogen-containing compounds having a polar functional group, represented by the general formulae (Am-9) and (Am-10).

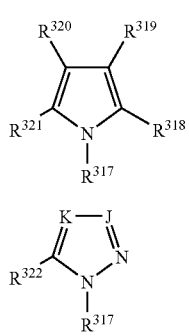

(Am-9)

(Am-10)

Herein, J is a nitrogen atom or $=C-R^{323}$. K is a nitrogen atom or $=C-R^{324}$. $R^{317}$ is a straight, branched or cyclic $C_2$-$C_{20}$ alkyl group in which some or all hydrogen atoms may be substituted by fluorine atoms and which has one or more polar functional groups, the polar functional group being selected from among hydroxyl, carbonyl, ester, ether, sulfide, carbonate, cyano and acetal groups and mixtures thereof. $R^{318}$, $R^{319}$, $R^{320}$ and $R^{321}$ are each independently a hydrogen atom, a straight, branched or cyclic $C_1$-$C_{10}$ alkyl group or aryl group, or a pair of $R^{318}$ and $R^{319}$ and a pair of $R^{320}$ and $R^{321}$, taken together, may form a benzene, naphthalene or pyridine ring with the carbon atoms to which they are attached. $R^{322}$ is a hydrogen atom, a straight, branched or cyclic $C_1$-$C_{10}$ alkyl group or aryl group. $R^{323}$ and $R^{324}$ each are a hydrogen atom, a straight, branched or cyclic $C_1$-$C_{10}$ alkyl group or aryl group, or a pair of $R^{322}$ and $R^{324}$, taken together, may form a benzene or naphthalene ring with the carbon atoms to which they are attached.

Also included are amine compounds having an aromatic carboxylic acid ester structure, represented by the general formulae (Am-11) to (Am-14).

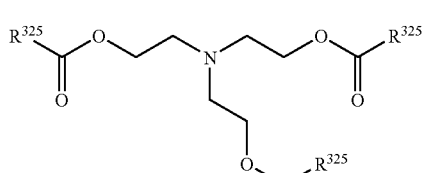

(Am-11)

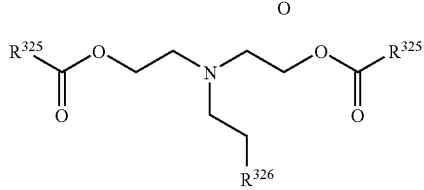

(Am-12)

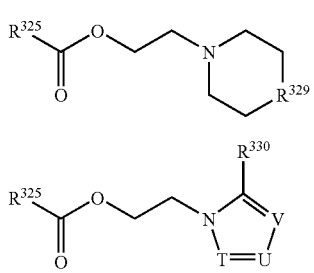

(Am-13)

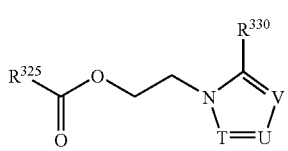

(Am-14)

Herein $R^{325}$ is a $C_6$-$C_{20}$ aryl group or $C_4$-$C_{20}$ hetero-aromatic group, in which some or all hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{326}$ is $CO_2R^{327}$, $OR^{328}$ or cyano group. $R^{327}$ is a $C_1$-$C_{10}$ alkyl group, in which some methylene groups may be replaced by oxygen atoms. $R^{328}$ is a $C_1$-$C_{10}$ alkyl or acyl group, in which some methylene groups may be replaced by oxygen atoms. $R^{329}$ is a single bond, methylene, ethylene, sulfur atom or —O(CH$_2$CH$_2$O)$_h$— group wherein h is 0, 1, 2, 3 or 4. $R^{330}$ is hydrogen, methyl, ethyl or phenyl. T is a nitrogen atom or $CR^{331}$. U is a nitrogen atom or $CR^{332}$. V is a nitrogen atom or $CR^{333}$. $R^{331}$, $R^{332}$ and $R^{333}$ are each independently hydrogen, methyl or phenyl. Alternatively, a pair of $R^{331}$ and $R^{332}$ or a pair of $R^{332}$ and $R^{333}$ may bond together to form a $C_6$-$C_{20}$ aromatic ring or $C_2$-$C_{20}$ hetero-aromatic ring with the carbon atoms to which they are attached.

Further included are amine compounds of 7-oxanorbornane-2-carboxylic ester structure, represented by the general formula (Am-15).

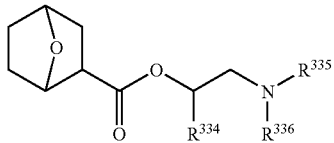

(Am-15)

Herein $R^{334}$ is hydrogen or a straight, branched or cyclic $C_1$-$C_{10}$ alkyl group. $R^{335}$ and $R^{336}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{335}$ and $R^{336}$, taken together, may form a $C_2$-$C_{20}$ heterocyclic or hetero-aromatic ring with the nitrogen atom to which they are attached.

The quenchers may be used alone or in admixture of two or more. The quencher is preferably formulated in an amount of 0.001 to 2 parts, and especially 0.01 to 1 part by weight, per 100 parts by weight of the base resin. Less than 0.001 phr of the quencher may achieve no addition effect whereas more than 2 phr may lead to too low a sensitivity.

Component E

In one preferred embodiment, the resist composition further contains (E) an auxiliary photoacid generator other than the photoacid generator of formula (1a). It may be any compound capable of generating an acid upon exposure to high-energy radiation such as UV, deep UV, electron beam, EUV, x-ray, excimer laser beam, gamma-ray or synchrotron radiation. Suitable auxiliary photoacid generators include sulfonium salts, iodonium salts, sulfonyldiazomethane, N-sulfonyloxydicarboxyimide, O-arylsulfonyloxime and O-alkylsulfonyloxime photoacid generators. Exemplary auxiliary photoacid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations include diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Iodonium salts based on combination of the foregoing examples are included.

N-sulfonyloxydicarboximide photoacid generators include combinations of imide skeletons with sulfonates. Exemplary imide skeletons are succinimide, naphthalenedicarboximide, phthalimide, cyclohexyldicarboximide, 5-norbornene-2,3-dicarboximide, and 7-oxabicyclo[2.2.1]-5-heptene-2,3-dicarboximide. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Photoacid generators in the form of O-arylsulfonyloxime compounds and O-alkylsulfonyloxime compounds (oxime sulfonates) include oxime sulfonates having an electron withdrawing group such as trifluoromethyl incorporated for increased stability, having the formula (OX-1).

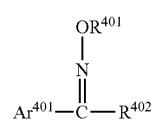

(Ox-1)

Herein $R^{401}$ is a substituted or unsubstituted $C_1$-$C_{10}$ haloalkylsulfonyl or halobenzenesulfonyl group, $R^{402}$ is a $C_1$-$C_{11}$ haloalkyl group, and $Ar^{401}$ is substituted or unsubstituted aromatic or hetero-aromatic group.

Examples include 2-[2,2,3,3,4,4,5,5-octafluoro-1-(nonafluorobutylsulfonyloxyimino)pentyl]fluorene, 2-[2,2,3,3,4,4-pentafluoro-1-(nonafluorobutylsulfonyloxyimino)butyl]fluorene, 2-[2,2,3,3,4,4,5,5,6,6-decafluoro-1-(nonafluorobutylsulfonyloxyimino)hexyl]fluorene, 2-[2,2,3,3,4,4,5,5-octafluoro-1-(nonafluorobutylsulfonyloxyimino)

pentyl]-4-biphenyl, 2-[2,2,3,3,4,4-pentafluoro-1-(nonafluorobutylsulfonyloxyimino)butyl]-4-biphenyl, and 2-[2,2,3,3,4,4,5,5,6,6-decafluoro-1-(nonafluorobutylsulfonyloxyimino)hexyl]-4-biphenyl. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl) difluoromethanesulfonate, and 4-oxo-1-adamantyloxycarbonyldifluoromethanesulfonate.

Among others, acid generators having the general formula (E-1) are preferred.

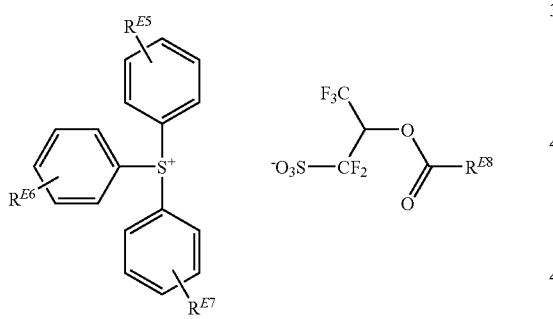

(E-1)

Herein $R^{E5}$, $R^{E6}$, and $R^{E7}$ are each independently hydrogen or a straight, branched or cyclic, monovalent $C_1$-$C_{20}$ hydrocarbon group which may contain a heteroatom. Examples of hydrocarbon groups optionally containing a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. $R^{E8}$ is a straight, branched or cyclic, monovalent $C_7$-$C_{30}$ hydrocarbon group which may contain a heteroatom, examples of which are exemplified below, but are not limited thereto.

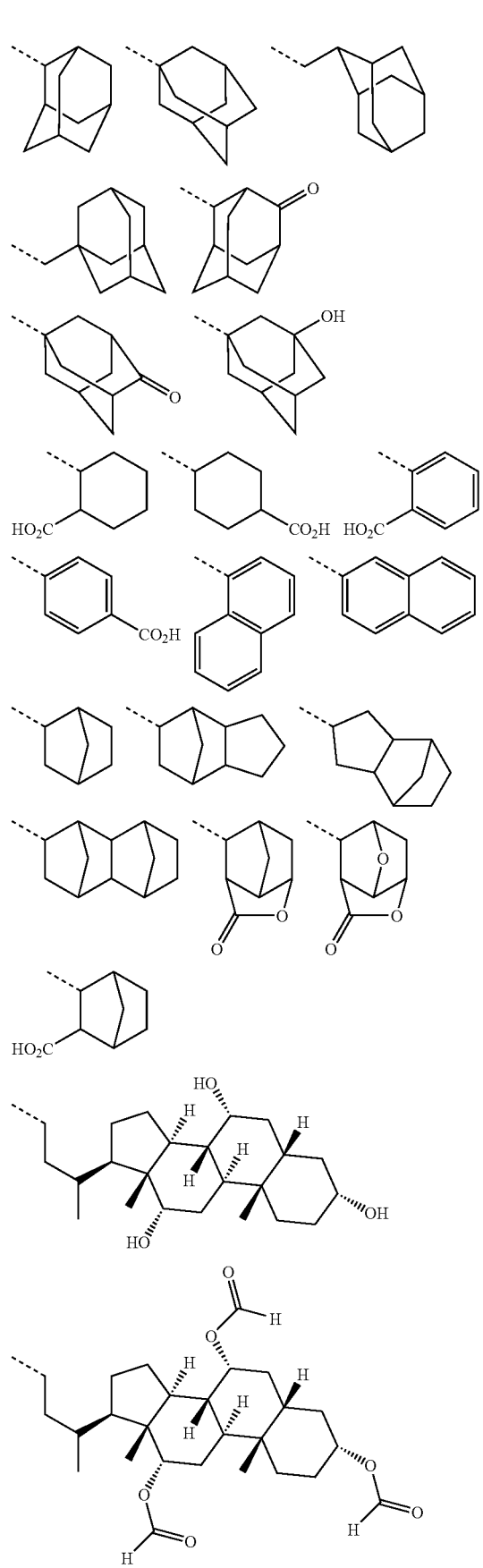

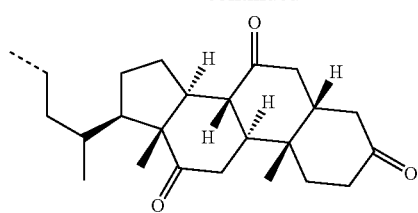
Illustrative examples of acid generators (E-1) are shown below.
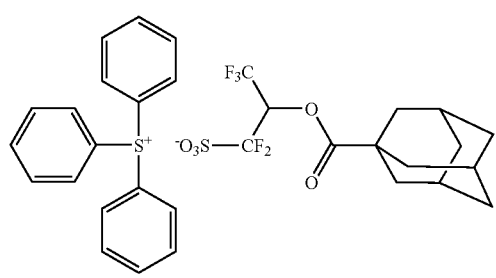
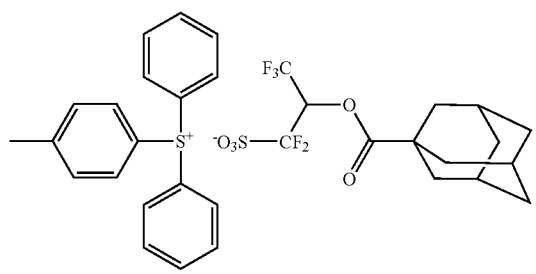
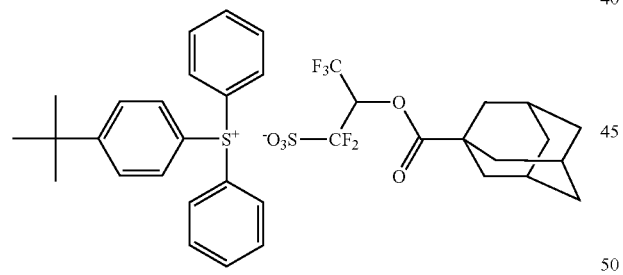
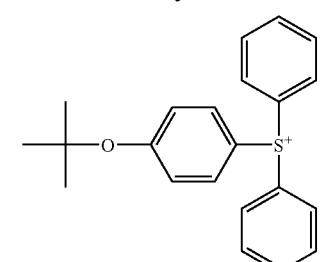
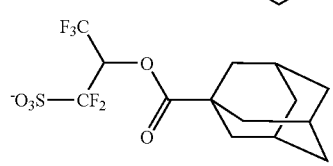
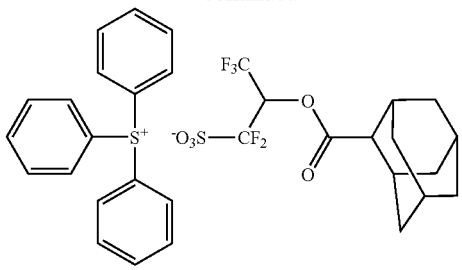
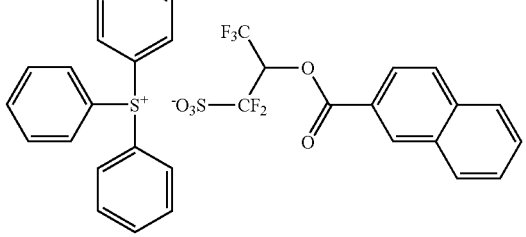
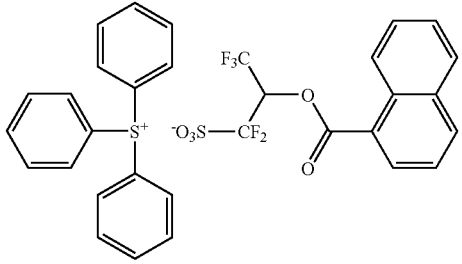
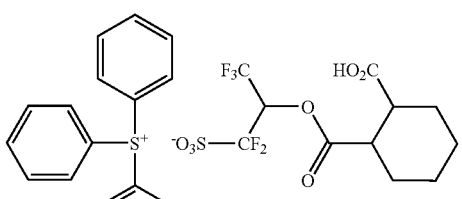
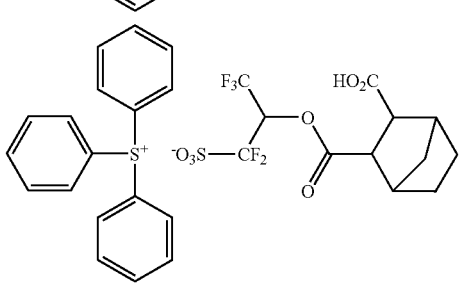

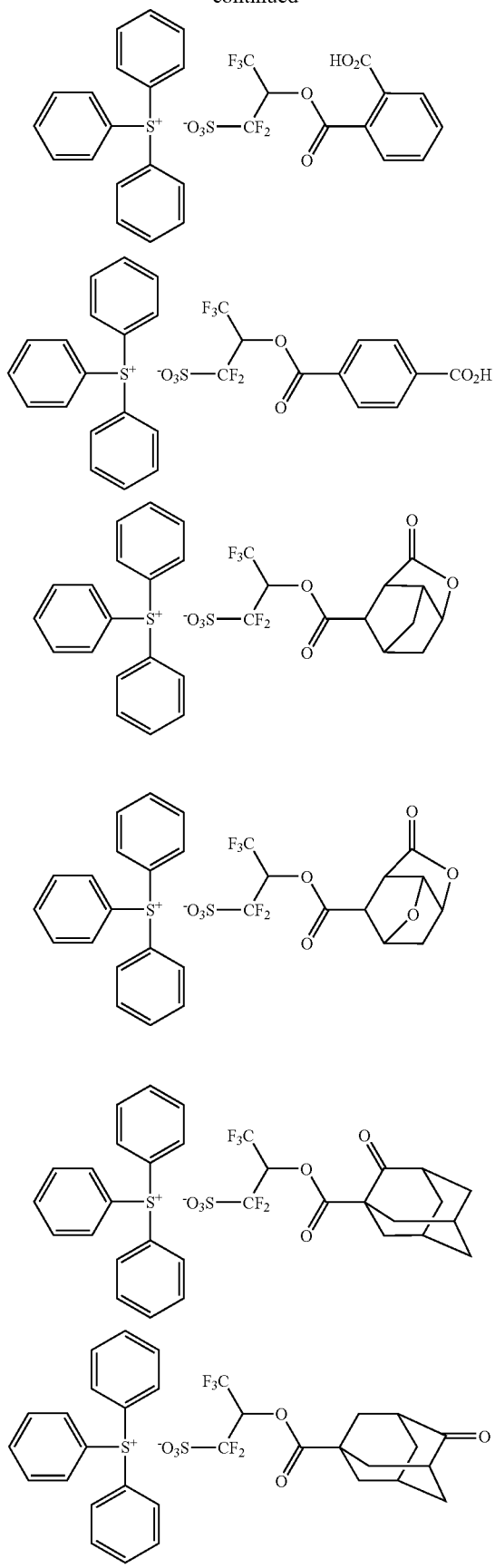
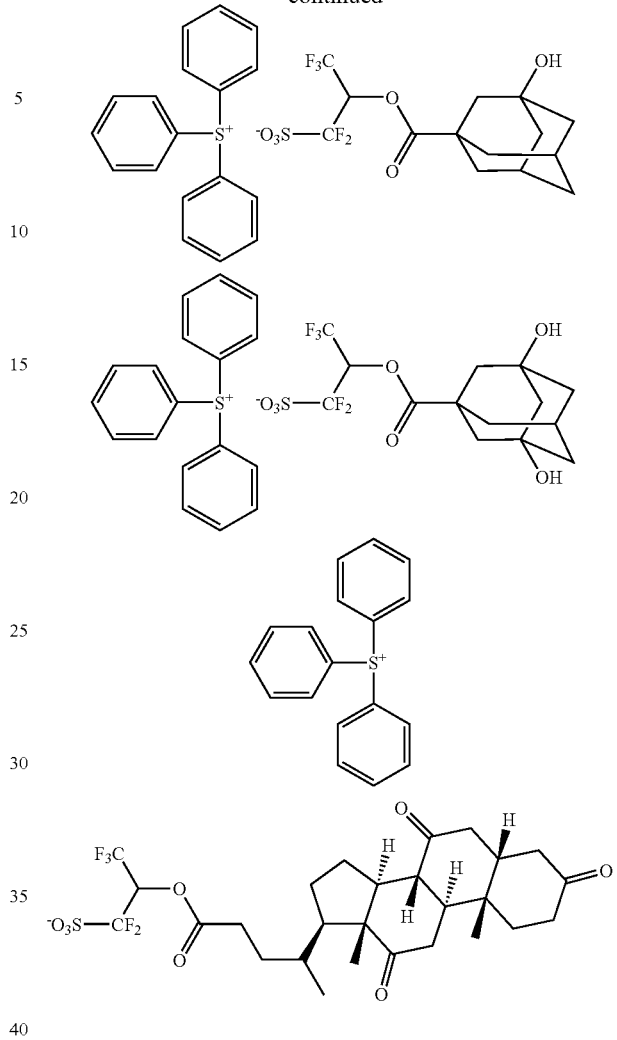

In the chemically amplified resist composition, the auxiliary photoacid generator (E) may be added in any desired amount as long as the objects of the invention are not compromised. An appropriate amount of the photoacid generator (E), when added, is 0.1 to 10 parts, and more preferably 0.1 to 5 parts by weight per 100 parts by weight of the base resin in the composition. Too high a proportion of the photoacid generator (E) may give rise to problems of degraded resolution and foreign matter upon development and resist film peeling. The photoacid generators (E) may be used alone or in admixture of two or more. The transmittance of the resist film can be controlled by using a photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the photoacid generator capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolan, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Component F

Component (F) is an organic acid derivative and/or a fluorinated alcohol. Illustrative, non-limiting, examples of the organic acid derivatives include phenol, cresol, catechol, resorcinol, pyrogallol, phloroglucin, bis(4-hydroxyphenyl) methane, 2,2-bis(4'-hydroxyphenyl)propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropionic acid, benzoic acid, salicylic acid, 4,4-bis(4'-hydroxyphenyl)valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

The fluorinated alcohol is an alcohol which is substituted with fluorine atoms except α-position. Those compounds terminated with 1,1,1,3,3,3-hexafluoro-2-propanol are desirable although the fluorinated alcohols are not limited thereto. Illustrative examples of the desirable fluorinated alcohols are given below.

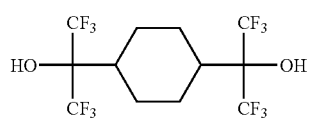

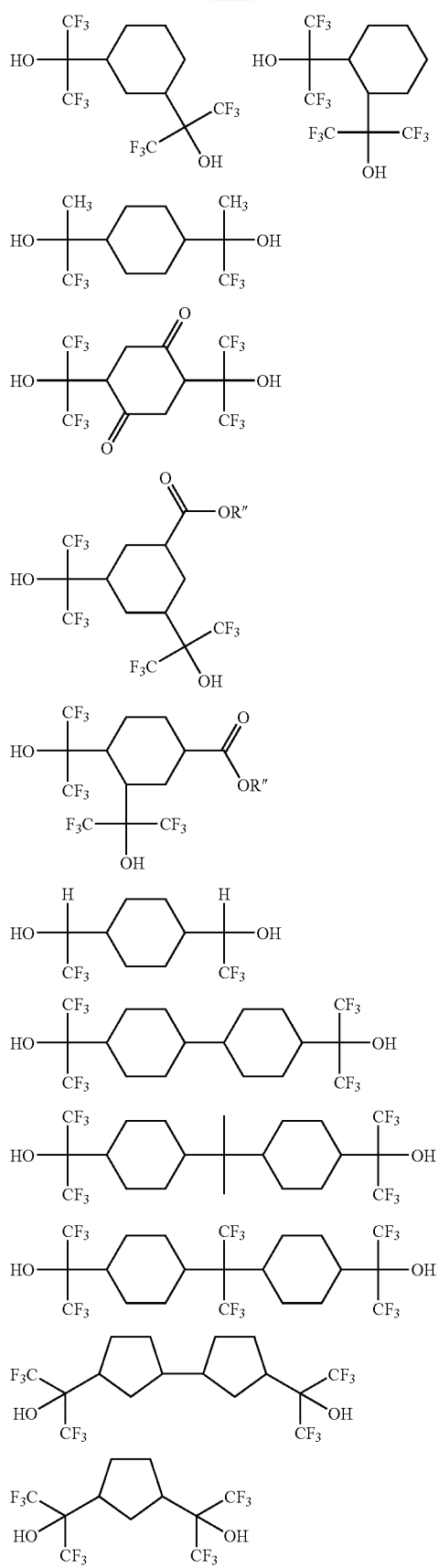

77
-continued
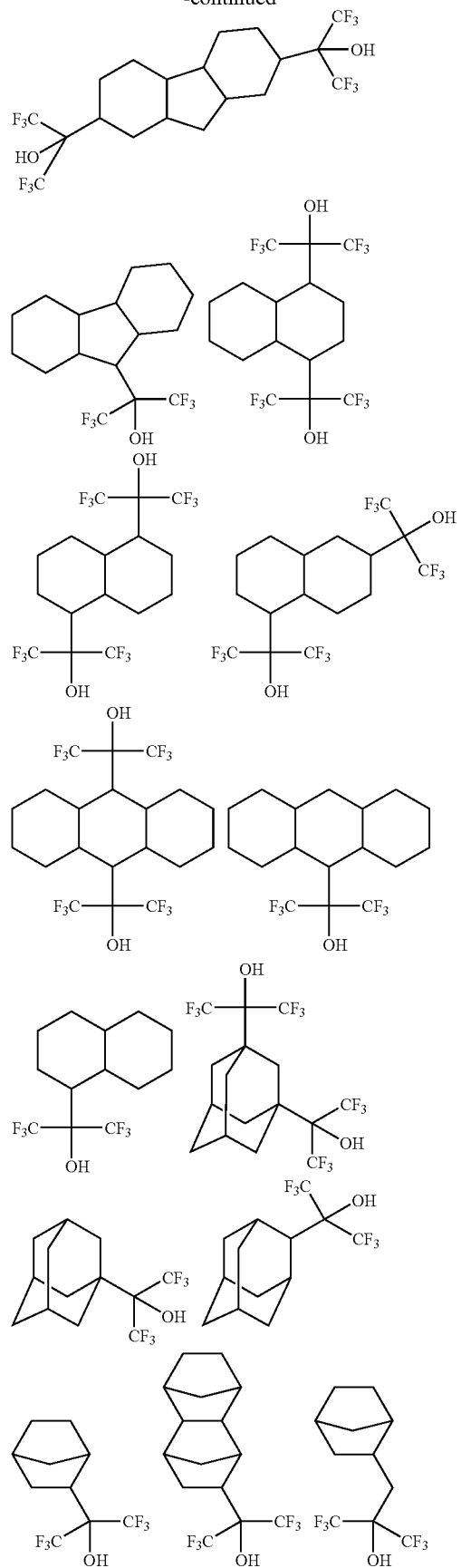
78
-continued
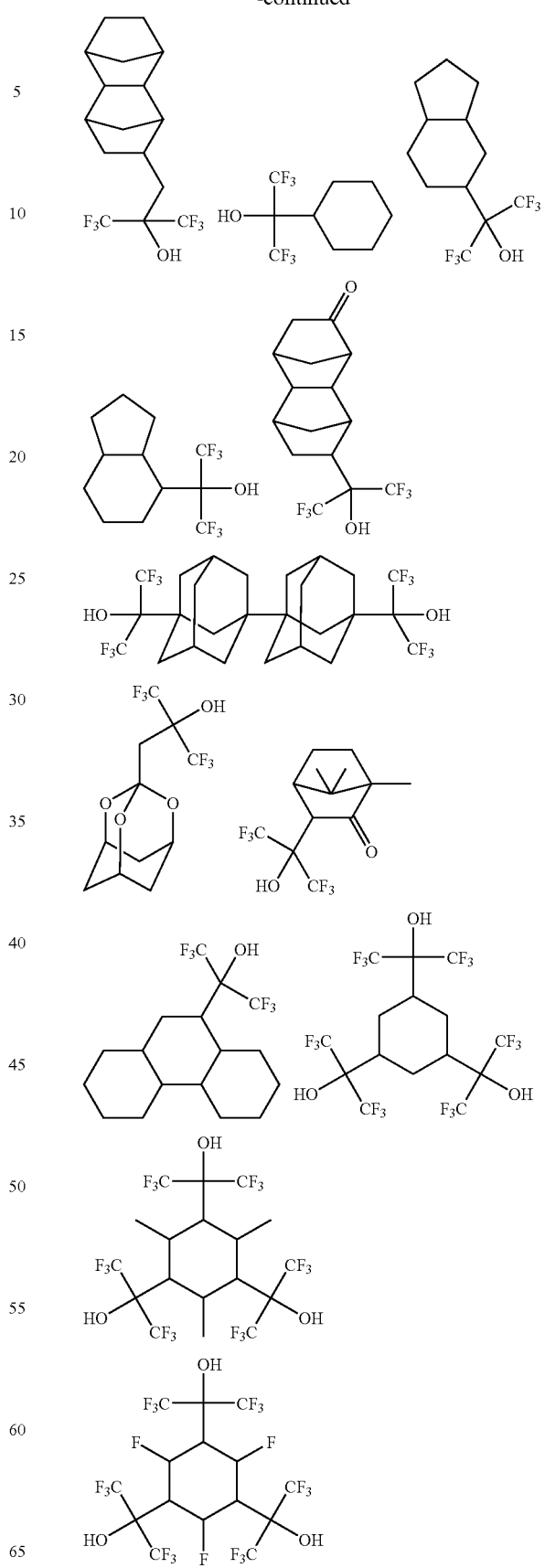

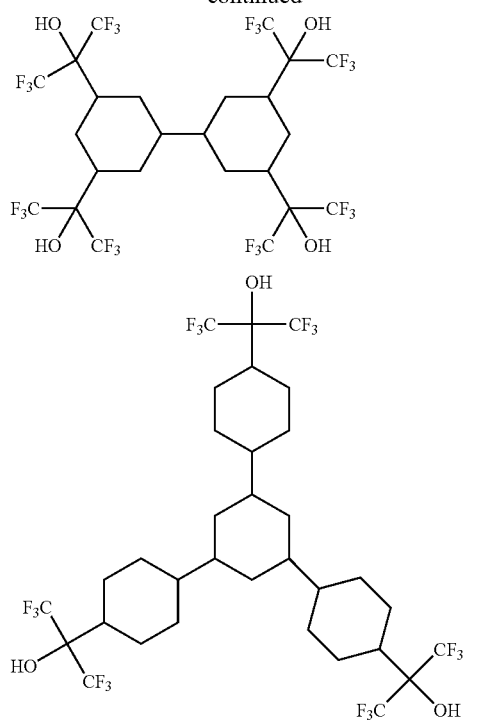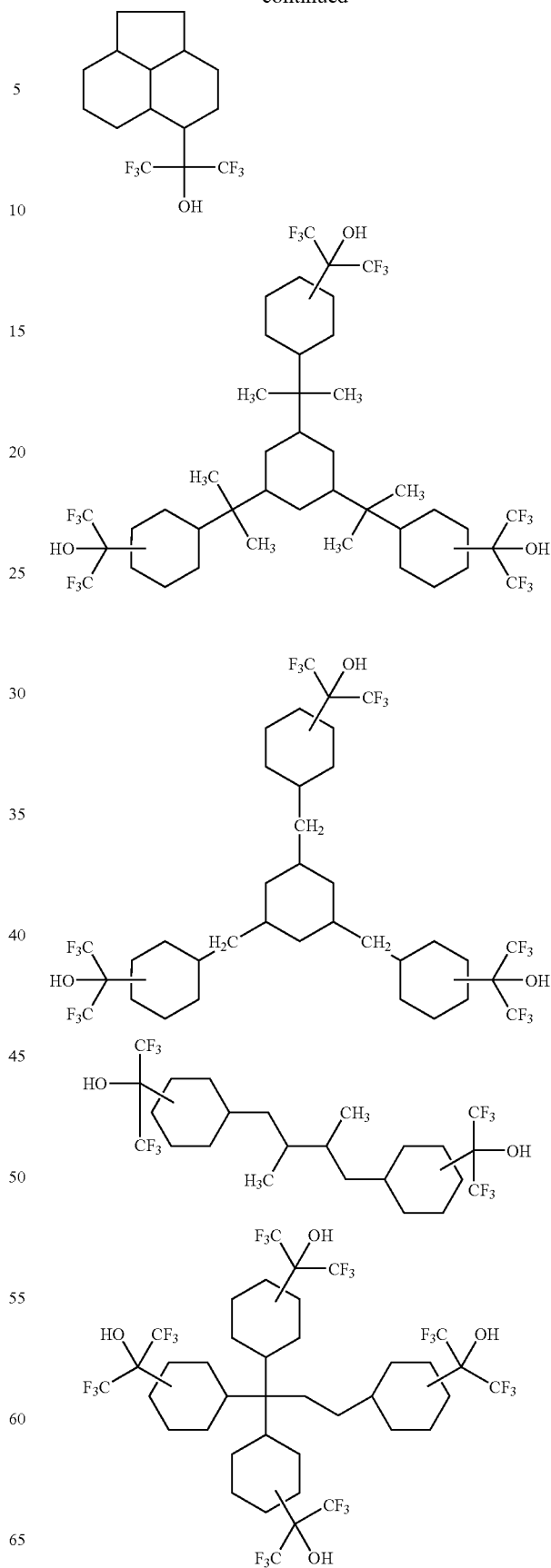

-continued

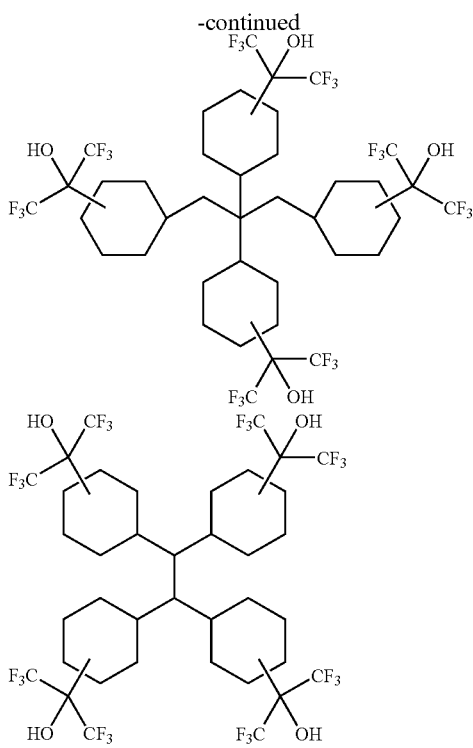

Note that R″ denotes a $C_2$-$C_{30}$ acetal or $C_4$-$C_{30}$ tertiary alkyl group as represented by formulae (L1) to (L4) illustrated for the base resin.

In the chemically amplified resist composition of the invention, the organic acid derivative or fluorinated alcohol is preferably formulated in an amount of up to 5 parts, and especially up to 1 part by weight, per 100 parts by weight of the base resin. More than 5 phr may result in too low a resolution. Depending on the combination of the other components in the resist composition, the organic acid derivative and fluorinated alcohol may be omitted.

Component G

In one preferred embodiment, the resist composition further contains (G) a compound with a weight average molecular weight of up to 3,000 which changes its solubility in an alkaline developer under the action of an acid, that is, a dissolution inhibitor. Typically, a compound obtained by substituting acid labile substituents for some or all hydrogen atoms of hydroxyl groups on a phenol or carboxylic acid derivative having a low molecular weight of up to 2,500 or fluorinated alcohol is added as the dissolution inhibitor.

Examples of the phenol or carboxylic acid derivative having a weight average molecular weight of up to 2,500 include bisphenol A, bisphenol H, bisphenol S, 4,4-bis(4'-hydroxyphenyl)valeric acid, tris(4-hydroxyphenyl)methane, 1,1,1-tris(4'-hydroxyphenyl)ethane, 1,1,2-tris(4'-hydroxyphenyl)ethane, phenolphthalein, thymolphthalein, cholic acid, deoxycholic acid, and lithocholic acid. Examples of the fluorinated alcohol include compounds terminated with 1,1,1,3,3,3-hexafluoro-2-propanol as described above. The acid labile substituents are the same as those exemplified as the acid labile groups in the polymer.

Illustrative, non-limiting, examples of the dissolution inhibitors which are useful herein include bis(4-(2'-tetrahydropyranyloxy)phenyl)methane, bis(4-(2'-tetrahydrofuranyloxy)phenyl)methane, bis(4-tert-butoxyphenyl)methane, bis(4-tert-butoxycarbonyloxyphenyl)methane, bis(4-tert-butoxycarbonylmethyloxyphenyl)methane, bis(4-(1'-ethoxyethoxy)phenyl)methane, bis(4-(1'-ethoxypropyloxy)phenyl)methane, 2,2-bis(4'-(2"-tetrahydropyranyloxy))propane, 2,2-bis(4'-(2"-tetrahydrofuranyloxy)phenyl)propane, 2,2-bis(4'-tert-butoxyphenyl)propane, 2,2-bis(4'-tert-butoxycarbonyloxyphenyl)propane, 2,2-bis(4-tert-butoxycarbonylmethyloxyphenyl)propane, 2,2-bis(4'-(1"-ethoxyethoxy)phenyl)propane, 2,2-bis(4'-(1"-ethoxypropyloxy)phenyl)propane, tert-butyl 4,4-bis(4'-(2"-tetrahydropyranyloxy)phenyl)valerate, tert-butyl 4,4-bis(4'-(2"-tetrahydrofuranyloxy)phenyl)valerate, tert-butyl 4,4-bis(4'-tert-butoxyphenyl)valerate, tert-butyl 4,4-bis(4-tert-butoxycarbonyloxyphenyl)valerate, tert-butyl 4,4-bis(4'-tert-butoxycarbonylmethyloxyphenyl)-valerate, tert-butyl 4,4-bis(4'-(1"-ethoxyethoxy)phenyl)valerate, tert-butyl 4,4-bis(4'-(1"-ethoxypropyloxy)phenyl)valerate, tris(4-(2'-tetrahydropyranyloxy)phenyl)methane, tris(4-(2'-tetrahydrofuranyloxy)phenyl)methane, tris(4-tert-butoxyphenyl)methane, tris(4-tert-butoxycarbonyloxyphenyl)methane, tris(4-tert-butoxycarbonyloxymethylphenyl)methane, tris(4-(1'-ethoxyethoxy)phenyl)methane, tris(4-(1'-ethoxypropyloxy)phenyl)methane, 1,1,2-tris(4'-(2"-tetrahydropyranyloxy)phenyl)ethane, 1,1,2-tris(4'-(2"-tetrahydrofuranyloxy)phenyl)ethane, 1,1,2-tris(4'-tert-butoxyphenyl)ethane, 1,1,2-tris(4'-tert-butoxycarbonyloxyphenyl)ethane, 1,1,2-tris(4'-tert-butoxycarbonylmethyloxyphenyl)ethane, 1,1,2-tris(4'-(1'-ethoxyethoxy)phenyl)ethane, 1,1,2-tris(4'-(1'-ethoxypropyloxy)phenyl)ethane, tert-butyl cholate, tert-butyl deoxycholate, and tert-butyl lithocholate. The compounds described in JP-A 2003-107706 are also useful.

In the resist composition of the invention, an appropriate amount of the dissolution inhibitor (G) is up to 20 parts, and especially up to 15 parts by weight per 100 parts by weight of the base resin. With more than 20 phr of the dissolution inhibitor, the resist composition becomes less heat resistant because of an increased content of monomer components.

Component C'

The base resin used in the negative working resist composition is (C') a base resin which is normally alkali soluble, but becomes substantially alkali insoluble under the action of a crosslinker. It is preferably a precursor resin which will be substituted with acid labile groups to form the base resin (C).

Examples of the alkali-soluble resin include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, but are not limited to these combinations.

To impart a certain function, suitable substituent groups may be introduced into some of the phenolic hydroxyl and carboxyl groups on the foregoing polymer (to be protected with acid labile groups). Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isobornyl, and cyclohexyl. It is also possible to introduce acid-decomposable substituent groups such as tert-butoxycarbonyl and relatively acid-undecomposable substituent groups such as tert-butyl and tert-butoxycarbonylmethyl.

In the resist composition, the resin (C') is blended in any desired amount, preferably of 65 to 99 parts by weight, especially 65 to 98 parts by weight per 100 parts by weight of the solids (inclusive of that resin).

Component H

Formulated in the negative resist composition is an acid crosslinker (H) which forms a crosslinked structure under the action of acid. Typical crosslinkers are compounds having at least two hydroxymethyl, alkoxymethyl, epoxy or vinyl ether groups within a molecule. Substituted glycoluril derivatives, urea derivatives, and hexa(methoxymethyl)melamine compounds are suitable as the acid crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslinkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine.

In the chemically amplified resist composition, an appropriate amount of the acid crosslinker (H) is, though not limited thereto, 1 to 20 parts, and especially 5 to 15 parts by weight per 100 parts by weight of the base resin. The crosslinkers may be used alone or in admixture of two or more.

Component S

In the chemically amplified resist composition of the invention, (S) a surfactant for improving coating characteristics may be added as an optional component. Illustrative, non-limiting, examples of the surfactant (S) include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, R08, R30, R90 and R94 (Dai-Nippon Ink & Chemicals, Inc.), Fluorad FC-430, FC-431, FC-4430 and FC-4432 (Sumitomo 3M Co., Ltd.), Asahiguard AG710, Surflon S-381, S-382, S-386, SC101, SC102, SC103, SC104, SC105, SC106, Surfynol E1004, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Additional useful surfactants include partially fluorinated oxetane ring-opened polymers having the structural formula (surf-1).

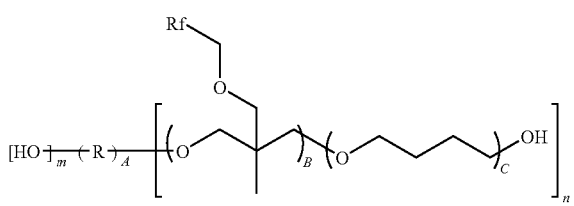

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

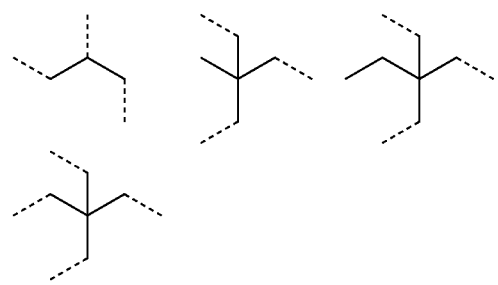

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430, Surflon S-381, Surfynol E1004, KH-20 and KH-30, and oxetane ring-opened polymers of formula (surf-1) are preferred. These surfactants may be used alone or in admixture.

In the chemically amplified resist composition of the invention, the surfactant is preferably formulated in an amount of up to 2 parts, and especially up to 1 part by weight, per 100 parts by weight of the base resin.

In one embodiment wherein the immersion lithography using water is applied to the resist composition of the invention, particularly in the absence of a resist protective film, the resist composition may have added thereto another surfactant having a propensity to segregate at the resist surface after spin coating for achieving a function of minimizing water penetration or leaching. The preferred other surfactant is a polymeric surfactant which is insoluble in water, but soluble in alkaline developer, and especially which is water repellent and enhances water slippage. Suitable polymeric surfactants are shown below.

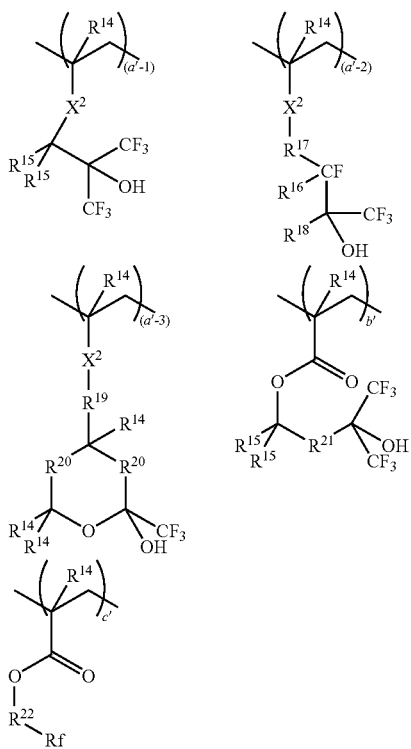

Herein $R^{14}$ is each independently hydrogen, fluorine, methyl or trifluoromethyl. $R^{15}$ is each independently hydrogen or a straight, branched or cyclic $C_1$-$C_{20}$ alkyl or fluoroalkyl group, or two $R^{15}$ in a common monomer may bond together to form a ring with the carbon atom to which they are attached, and in this event, they together represent a straight, branched or cyclic $C_2$-$C_{20}$ alkylene or fluoroalkylene group. $R^{16}$ is fluorine or hydrogen, or $R^{16}$ may bond with $R^{17}$ to form a non-aromatic ring of 3 to 10 carbon atoms in total with the carbon atom to which they are attached. $R^{17}$ is a straight, branched or cyclic $C_1$-$C_6$ alkylene group in which at least one hydrogen atom may be substituted by a fluorine atom. $R^{18}$ is a straight or branched $C_1$-$C_{10}$ alkyl group in which at least one hydrogen atom is substituted by a fluorine atom. Alternatively, $R^{17}$ and $R^{18}$ may bond together to form a ring with the carbon atoms to which they are attached. In this event, $R^{17}$, $R^{18}$ and the carbon atoms to which they are attached together represent a trivalent organic group of 2 to 12 carbon atoms in total. $R^{19}$ is a single bond or a $C_1$-$C_4$ alkylene. $R^{20}$ is each independently a single bond, —O—, or —$CR^{14}R^{14}$—. $R^{21}$ is a straight or branched $C_1$-$C_4$ alkylene group, or may bond with $R^{15}$ within a common monomer to form a ring with the carbon atom to which they are attached. $R^{22}$ is 1,2-ethylene, 1,3-propylene, or 1,4-butylene. Rf is a linear perfluoroalkyl group of 3 to 6 carbon atoms, typically 3H-perfluoropropyl, 4H-perfluorobutyl, 5H-perfluoropentyl, or 6H-perfluorohexyl. $X^2$ is each independently —C(=O)—O—, —O—, or —C(=O)—$R^{23}$—C(=O)—O—. $R^{23}$ is a straight, branched or cyclic $C_1$-$C_{10}$ alkylene group. The subscripts are in the range: $0 \leq (a'-1) < 1$, $0 \leq (a'-2) < 1$, $0 \leq (a'-3) < 1$, $0 \leq (a'-1)+(a'-2)+(a'-3) < 1$, $0 \leq b' < 1$, $0 \leq c' < 1$, and $0 < (a'-1)+(a'-2)+(a'-3)+b'+c' \leq 1$.

In the chemically amplified resist composition of the invention, the polymeric surfactant is preferably formulated in an amount of 0.001 to 20 parts, and more preferably 0.01 to 10 parts by weight, per 100 parts by weight of the base resin. Reference should also be made to JP-A 2007-297590.

In the chemically amplified resist composition of the invention, a UV absorber may be added. Those UV absorbers described in JP-A 11-190904 are useful, but the UV absorber is not limited thereto. Exemplary UV absorbers are diaryl sulfoxide derivatives such as bis(4-hydroxyphenyl)sulfoxide, bis(4-tert-butoxyphenyl)sulfoxide, bis(4-tert-butoxycarbonyloxyphenyl)sulfoxide, and bis[4-(1-ethoxyethoxy)phenyl]sulfoxide; diarylsulfone derivatives such as bis(4-hydroxyphenyl)sulfone, bis(4-tert-butoxyphenyl)sulfone, bis(4-tert-butoxycarbonyloxyphenyl)sulfone, bis[4-(1-ethoxyethoxy)phenyl]sulfone, and bis[4-(1-ethoxypropoxy)phenyl]sulfone; diazo compounds such as benzoquinonediazide, naphthoquinonediazide, anthraquinonediazide, diazofluorene, diazotetralone, and diazophenanthrone; quinonediazido group-containing compounds such as complete or partial ester compounds between naphthoquinone-1,2-diazido-5-sulfonic acid chloride and 2,3,4-trihydroxybenzophenone and complete or partial ester compounds between naphthoquinone-1,2-diazido-4-sulfonic acid chloride and 2,4,4'-trihydroxybenzophenone; tert-butyl 9-anthracenecarboxylate, tert-amyl 9-anthracenecarboxylate, tert-methoxymethyl 9-anthracenecarboxylate, tert-ethoxyethyl 9-anthracenecarboxylate, 2-tert-tetrahydropyranyl 9-anthracenecarboxylate, and 2-tert-tetrahydrofuranyl 9-anthracenecarboxylate.

The UV absorber may or may not be added to the resist composition depending on the type of resist composition. An appropriate amount of UV absorber, if added, is 0 to 10 parts, more preferably 0.5 to 10 parts, most preferably 1 to 5 parts by weight per 100 parts by weight of the base resin.

It is noted that optional components may be added in ordinary amounts as long as the objects of the invention are not compromised.

Any well-known lithography may be used to form a resist pattern from the chemically amplified resist composition of the invention. The composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, MoSi, etc.) by a suitable coating technique such as spin coating, roll coating, flow coating, dip coating, spray coating or doctor coating. The coating is prebaked on a hot plate at a temperature of 60 to 150° C. for 1 to 10 minutes, preferably 80 to 140° C. for 1 to 5 minutes. The resulting resist film is generally 0.1 to 2.0 µm thick. Through a photomask having a desired pattern, the resist film is then exposed to radiation, preferably having an exposure wavelength of up to 300 nm, such as UV, deep-UV, electron beam, EUV, x-ray, excimer laser light, γ-ray and synchrotron radiation. The preferred light source is a beam from an excimer laser, especially KrF excimer laser, deep UV of 245-255 nm wavelength and ArF excimer laser. The exposure dose is preferably in the range of about 1 to 200 mJ/cm$^2$, more preferably about 10 to 100 mJ/cm$^2$. The film is further baked on a hot plate at 60 to 150° C. for 1 to 5 minutes, preferably at 80 to 140° C. for 1 to 3 minutes (post-exposure baking=PEB).

Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray technique. In this way, a desired resist pattern is formed on the substrate. It is appreciated that the resist composition of the invention is best suited for micro-patterning using such high-energy radiation as deep UV with a wavelength of 254 to 193 nm, vacuum UV with a wavelength of 157 nm, electron beam, x-ray, excimer laser light, γ-ray and synchrotron radiation. With any of the above-described parameters outside the above-described range, the process may sometimes fail to produce the desired pattern.

In the practice of the invention, the immersion lithography process involving using ArF excimer laser of 193 nm wavelength and feeding a liquid such as water, glycerin or ethylene glycol between the substrate and the projection lens is advantageously applicable.

EXAMPLE

Synthesis Examples, Examples and Comparative Examples are given below for further illustrating the invention, but they are not to be construed as limiting the invention.

Synthesis Example 1

Synthesis of triphenylsulfonium chloride

Diphenyl sulfoxide, 40 g (0.2 mole), was dissolved in 400 g of dichloromethane, which was stirred under ice cooling. At a temperature below 20° C., 65 g (0.6 mole) of trimethylsilyl chloride was added dropwise to the solution, which was aged for 30 minutes at the temperature. Then, a Grignard reagent which had been prepared from 14.6 g (0.6 mole) of metallic magnesium, 67.5 g (0.6 mole) of chlorobenzene and 168 g of tetrahydrofuran (THF) was added dropwise at a temperature below 20° C. The reaction solution was aged for one hour, after which 50 g of water at a temperature below 20° C. was added to quench the reaction. To this solution, 150 g of water, 10 g of 12N hydrochloric acid, and 200 g of diethyl ether were further added. The water layer was separated and washed with 100 g of diethyl ether, yielding an aqueous solution of triphenylsulfonium chloride. The compound in aqueous solution form was used in the subsequent reaction without further isolation.

Synthesis Example 2

Synthesis of 4-tert-butylphenyldiphenylsulfonium bromide

The target compound was obtained by following the procedure of Synthesis Example 1 aside from using 4-tert-butylbromobenzene instead of the chlorobenzene in Synthesis Example 1 and increasing the amount of water for extraction.

Synthesis Example 3

Synthesis of 4-tert-butoxyphenyldiphenylsulfonium chloride

The target compound was obtained by following the procedure of Synthesis Example 1 aside from using 4-tert-butoxychlorobenzene instead of the chlorobenzene in Synthesis Example 1, using dichloromethane containing 5 wt % of triethylamine as the solvent, and increasing the amount of water for extraction.

Synthesis Example 4

Synthesis of tris(4-methylphenyl)sulfonium chloride

The target compound was obtained by following the procedure of Synthesis Example 1 aside from using bis(4-methylphenyl)sulfoxide instead of the diphenyl sulfoxide and 4-chlorotoluene instead of the chlorobenzene in Synthesis Example 1, and increasing the amount of water for extraction.

Synthesis Example 5

Synthesis of tris(4-tert-butylphenyl)sulfonium bromide

The target compound was obtained by following the procedure of Synthesis Example 1 aside from using bis(4-tert-butylphenyl)sulfoxide instead of the diphenyl sulfoxide and 4-tert-butylbromobenzene instead of the chlorobenzene in Synthesis Example 1, and increasing the amount of water for extraction.

Synthesis Example 6

Synthesis of bis(4-tert-butylphenyl)iodonium hydrogen sulfate

A mixture of 84 g (0.5 mole) of tert-butylbenzene, 53 g (0.25 mole) of potassium iodate and 50 g of acetic anhydride was stirred under ice cooling, and a mixture of 35 g of acetic anhydride and 95 g of conc. sulfuric acid was added dropwise at a temperature below 30° C. The resulting solution was aged for 3 hours at room temperature and ice cooled again, after which 250 g of water was added dropwise to quench the reaction. The reaction solution was extracted with 400 g of dichloromethane. The organic layer was discolored by adding 6 g of sodium hydrogen sulfite. The organic layer was washed with 250 g of water three times. The washed organic layer was concentrated in vacuum, obtaining a crude target product. The product was used in the subsequent reaction without further purification.

Synthesis Example 7

Synthesis of phenacyltetrahydrothiophenium bromide 88.2 g (0.44 mole) of phenacyl bromide and 39.1 g (0.44 mole) of tetrahydrothiophene were dissolved in 220 g of nitromethane, which was stirred for 4 hours at room temperature. 800 g of water and 400 g of diethyl ether were added to the reaction solution. The aqueous layer was taken out, which was an aqueous solution of the target compound, phenacyltetrahydrothiophenium bromide.

Synthesis Example 8

Synthesis of dimethylphenylsulfonium hydrogen sulfate

At room temperature, 6.2 g (0.05 mole) of thioanisol and 6.9 g (0.055 mole) of dimethyl sulfate were stirred for 12 hours. 100 g of water and 50 ml of diethyl ether were added to the reaction solution. The aqueous layer was taken out, which was an aqueous solution of the target compound, dimethylphenylsulfonium hydrogen sulfate.

Synthesis Example 9

Synthesis of sodium 2-pivaloyloxy-1,1-difluoroethanesulfonate [Anion-1]

Pivalic chloride and 2-bromo-2,2-difluoroethanol were mixed in tetrahydrofuran and ice cooled. Triethylamine was added to the mixture, from which 2-bromo-2,2-difluoroethyl pivalate was obtained by standard separatory operation and solvent distillation. The compound was reacted with sodium dithionite to form sodium sulfinate and oxidized with hydrogen peroxide, obtaining the target compound, sodium 2-pivaloyloxy-1,1-difluoroethanesulfonate.

The synthesis of carboxylate is well known, and the synthesis of sulfinic acid and sulfonic acid from alkyl halides is well known. The latter is described, for example, in JP-A 2004-2252.

Synthesis Example 10

Synthesis of triphenylsulfonium 2-pivaloyloxy-1,1-difluoroethanesulfonate [PAG Intermediate 1]

In 700 g of dichloromethane and 400 g of water were dissolved 159 g (0.37 mole) of sodium 2-pivaloyloxy-1,1-difluoroethanesulfonate (purity 63%) and 132 g (0.34 mole) of triphenylsulfonium iodide. The organic layer was separated and washed with 200 g of water three times. The organic layer was concentrated and diethyl ether was added to the residue for recrystallization. The target compound was obtained as white crystals. 164 g (yield 95%).

Synthesis Example 11

Synthesis of 4-tert-butylphenyldiphenylsulfonium 2-pivaloyloxy-1,1-difluoroethanesulfonate [PAG Intermediate 2]

In 150 g of dichloromethane were dissolved 20 g (0.052 mole) of sodium 2-pivaloyloxy-1,1-difluoroethanesulfonate (purity 70%) and 217 g (0.052 mole) of an aqueous solution of 4-tert-butylphenyldiphenylsulfonium bromide. The organic layer was separated and washed with 50 g of water three times. The organic layer was concentrated and diethyl ether was added to the residue for recrystallization. The target compound was obtained as white crystals. 26 g (yield 79%).

Synthesis Example 12

Synthesis of triphenylsulfonium 1,1-difluoro-2-hydroxyethanesulfonate [PAG Intermediate 3]

In 760 g of methanol was dissolved 243.5 g (0.48 mole) of triphenylsulfonium 2-pivaloyloxy-1,1-difluoroethanesulfonate. To this solution under ice cooling, an aqueous solution of sodium hydroxide (40 g sodium hydroxide in 120 g water) was added dropwise at a temperature below 5° C. The reaction solution was aged at room temperature for 8 hours, and dilute hydrochloric acid (99.8 g 12N hydrochloric acid in 200 g water) was added thereto at a temperature below 10° C. to quench the reaction. The methanol was distilled off in vacuum. To the residue was added 1,000 g of dichloromethane. The organic layer was washed with 30 g of saturated saline three times and concentrated. Diisopropyl ether, 1 L, was added to the concentrate for crystallization. The crystals were filtered and dried, obtaining the target compound. 187 g (purity 78%, net yield 78%).

Synthesis Example 13

Synthesis of triphenylsulfonium 1,1-difluoro-2-hydroxyethanesulfonate [PAG Intermediate 3]

In 200 g of methanol was dissolved 50.9 g (0.1 mole) of triphenylsulfonium 2-pivaloyloxy-1,1-difluoroethanesulfonate. To this solution under ice cooling, 2.0 g of a 28 wt % methanol solution of sodium methoxide was added. The reaction solution was aged at room temperature for 24 hours, and 1.0 g of 12N hydrochloric acid was added thereto at a temperature below 10° C. to quench the reaction. The methanol was distilled off in vacuum. To the residue was added 250 g of dichloromethane. The inorganic salt was filtered off, the filtrate was concentrated, and 150 g of diisopropyl ether was added to the concentrate for crystallization. The crystals were filtered and dried, obtaining the target compound. 42 g (purity 99%, net yield 99%).

Synthesis Example 14

Synthesis of triphenylsulfonium 1-difluorosulfomethyl-2,2,2-trifluoroethyl 4-oxo-5-oxatricyclo[4.2.1.0$^{3,7}$]nonane-2-carboxylate (PAG-A)

In 20 g of acetonitrile and 20 g of dichloromethane were dissolved 5.7 g (0.01 mole) of triphenylsulfonium 1,1-difluoro-2-hydroxyethanesulfonate (purity 74.4%), 1.2 g (0.012 mole) of triethylamine, and 0.12 g (0.001 mole) of N,N-dimethylaminopyridine. To this solution under ice cooling, 2.2 g (0.012 mole) of 4-oxo-5-oxatricyclo-[4.2.1.0$^{3,7}$]nonane-2-carboxylic acid chloride was added at a temperature below 5° C. The mixture was stirred at room temperature for one hour. Dilute hydrochloric acid (2 g 12N hydrochloric acid in 10 g water) was added thereto, and the solvent was distilled off in vacuum. To the residue were added 50 g of dichloromethane, 25 g of methyl isobutyl ketone and 20 g of water. The organic layer was separated and washed with 20 g of water, and the solvent was distilled off in vacuum. Ether was added to the residue for crystallization. The crystals were filtered and dried, obtaining 4.6 g (yield 78%) of the target compound.

Figure 2:
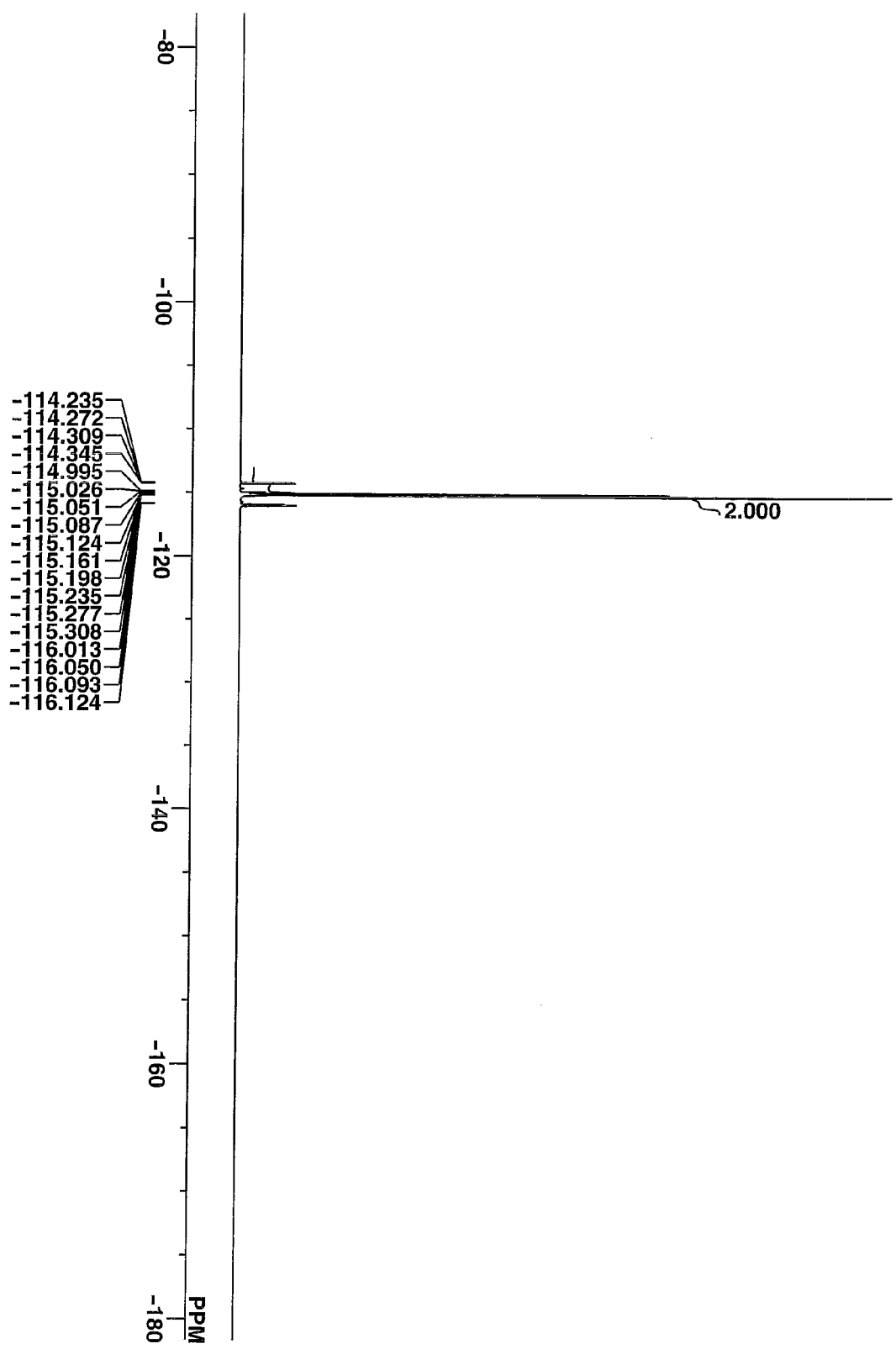
FIG. 2 is a diagram showing the $^{19}$F-NMR/DMSO-$d_6$ spectrum of PAG-A in Synthesis Example 14.

The target compound was analyzed by spectroscopy. The data of infrared (IR) absorption spectroscopy and time-of-flight mass spectrometry (TOFMS) are shown below. The nuclear magnetic resonance spectra, $^1$H-NMR and $^{19}$F-NMR in DMSO-d$_6$ are shown in FIGS. 1 and 2.

IR spectra (KBr, cm$^{-1}$):
1768, 1749, 1477, 1446, 1390, 1353, 1324, 1309, 1292, 1255, 1240, 1214, 1180, 1151, 1133, 1101, 1083, 1066, 1051, 1029, 997, 956, 759, 750, 682, 642

TOFMS (MALDI):
Positive M$^+$263 (corresponding to $(C_6H_5)_3S^+$)
Negative M$^-$325 (corresponding to $C_9H_9O_4$—$CH_2CF_2SO_3^-$)

Synthesis Example 15

Synthesis of triphenylsulfonium 1,1-difluoro-1-sulfoethyl hydrogen cyclohexane-1,2-dicarboxylate (PAG-B)

In 108 g of dichloromethane were dissolved 8.48 g (0.02 mole) of triphenylsulfonium 1,1-difluoro-2-hydroxyethanesulfonate (purity 99%) and 6.16 g (0.04 mole) of trans-cyclohexane-1,2-dicarboxylic anhydride. While the solution was stirred under ice cooling, 1.46 g (0.012 mole) of N,N-dimethylaminopyridine in 28 g of dichloromethane was added dropwise at a temperature below 10° C. Stirring continued for 5 hours under ice cooling, after which dilute hydrochloric acid (2.1 g 12N hydrochloric acid in 20 g water) was added. The organic layer was separated and washed with 40 g of water, and the dichloromethane was distilled off in vacuum. Methyl isobutyl ketone was added to the residue for crystallization. The crystals were filtered and dried, obtaining the target compound as white crystals. 10.1 g (yield 87%).

The trans/cis ratio was 97.5/2.5.

Figure 3:
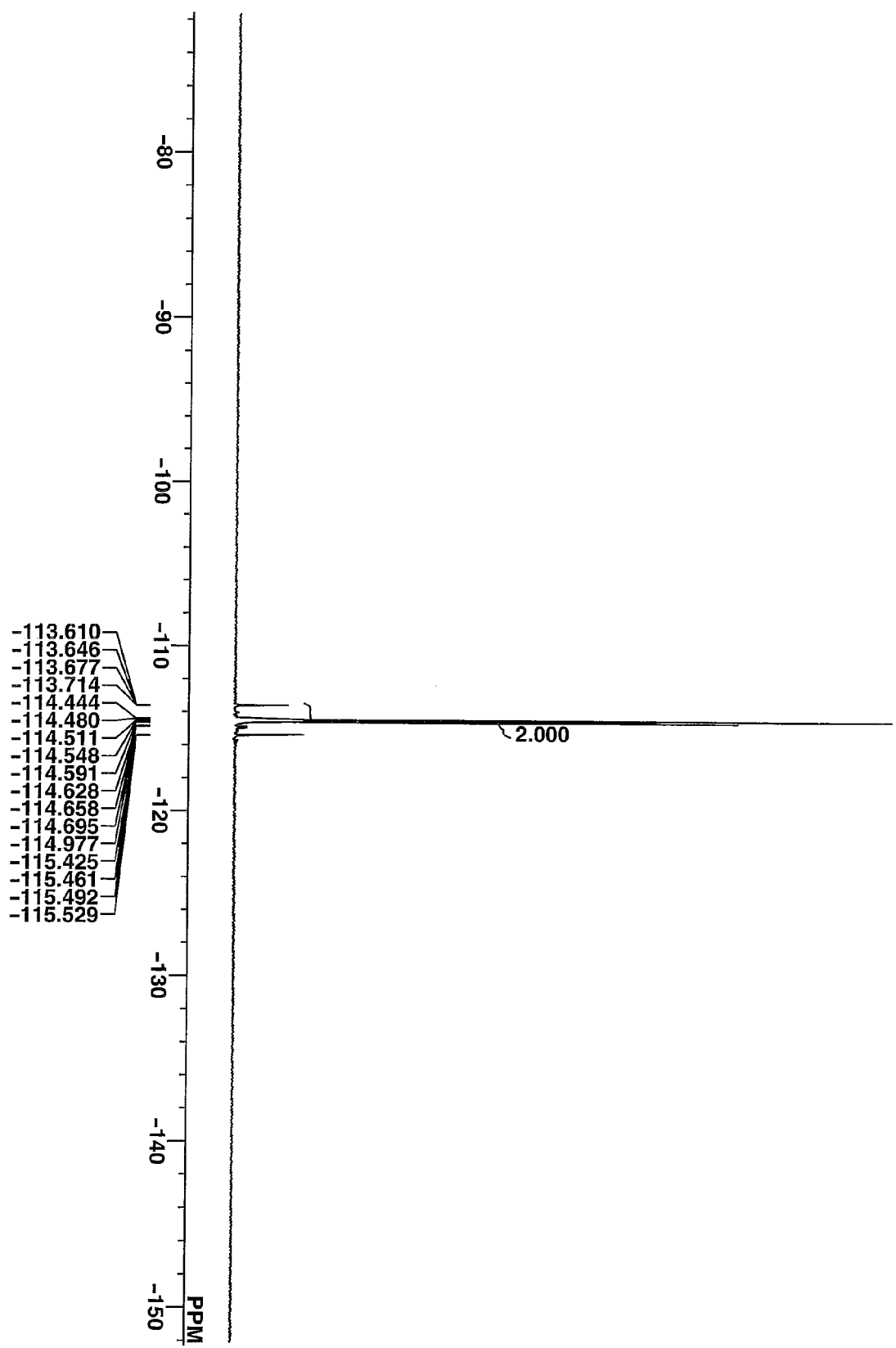
FIG. 3 is a diagram showing the $^{19}$F-NMR/CDCl$_3$ spectrum of PAG-B in Synthesis Example 15.
Figure 4:
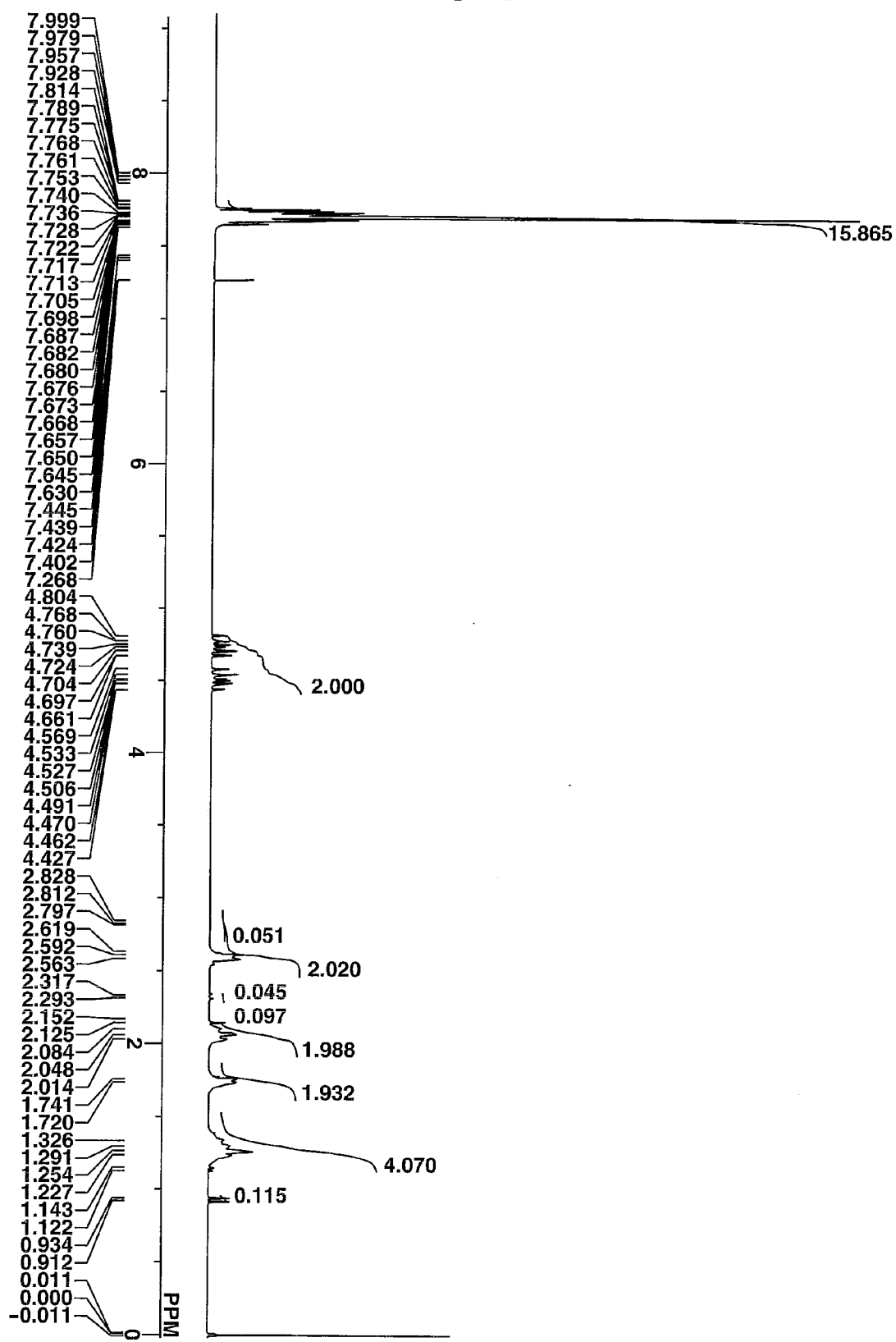
FIG. 4 is a diagram showing the $^1$H-NMR/CDCl$_3$ spectrum of PAG-B in Synthesis Example 15.

The target compound was analyzed by spectroscopy. The data of IR spectroscopy and time-of-flight mass spectrometry (TOFMS) are shown below. The nuclear magnetic resonance spectra, $^{19}$F-NMR and $^1$H-NMR in CDCl$_3$ are shown in FIGS. 3 and 4.

IR spectra (KBr, cm$^{-1}$):
3087, 2942, 2859, 1745, 1725, 1477, 1446, 1315, 1274, 1216, 1160, 1132, 1112, 1016, 997, 985, 757, 746, 682, 636, 522, 505, 491

TOFMS (MALDI):
Positive M$^+$263 (corresponding to $(C_6H_5)_3S^+$)
Negative M$^-$315 (corresponding to $C_9H_9O_4$—$CH_2CF_2SO_3^-$)

Synthesis Example 16

Synthesis of triphenylsulfonium 1-difluorosulfomethyl-2,2,2-trifluoroethyl cyclohexyl bicyclo[2.2.1]heptane-2,3-dicarboxylate (PAG-C)

The target compound was synthesized as in Synthesis Example 14 except that 3-cyclohexyloxycarbonylbicycle[2.2.1]-heptane-2-carboxylic acid chloride was used instead of 4-oxo-5-oxatricyclo[4.2.1.0$^{3,7}$]nonane-2-carboxylic acid chloride in Synthesis Example 14.

The resulting salts PAG-A, PAG-B and PAG-C have the structural formulae shown below.

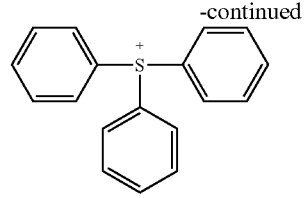

[PAG-A]

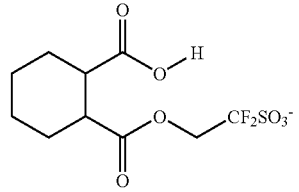

[PAG-B]

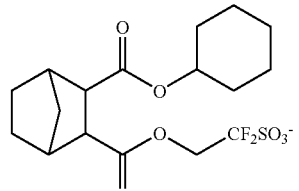

[PAG-C]

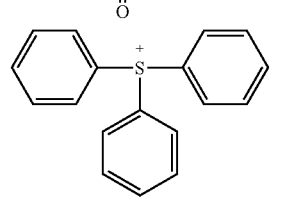

It is noted that the anion moiety of PAG-A, 4-oxo-5-oxatricyclo[4.2.1.0$^{3,7}$]nonane-2-carbonyloxy group has endo- and exo-forms at one site; the anion moiety of PAG-B, cyclohexane-1,2-dicarboxylic acid derivative has cis/trans forms; and the anion moiety of PAG-C, bicyclo[2.2.1]heptane-2,3-dicarboxylic acid derivative has endo- and exo-forms at two sites.

The photoacid generator used herein may consist of a single compound or of isomers.

PAG-A, PAG-B and PAG-C are illustrated only as typical examples, and photoacid generators PAG-D to PAG-X having different cations, shown below, may be synthesized by the same procedure.

[PAG D]

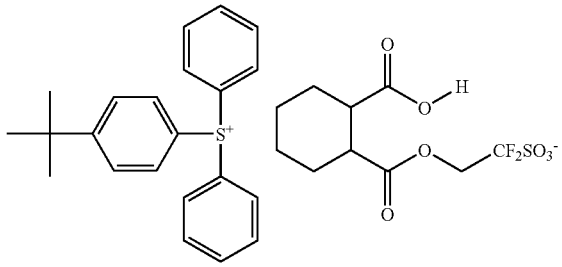

[PAG E]
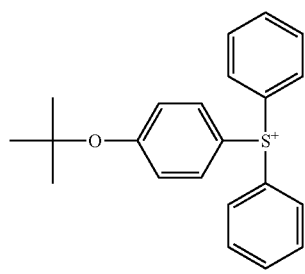
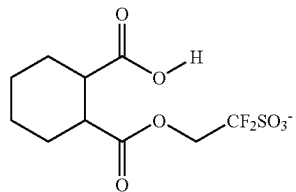
[PAG F]
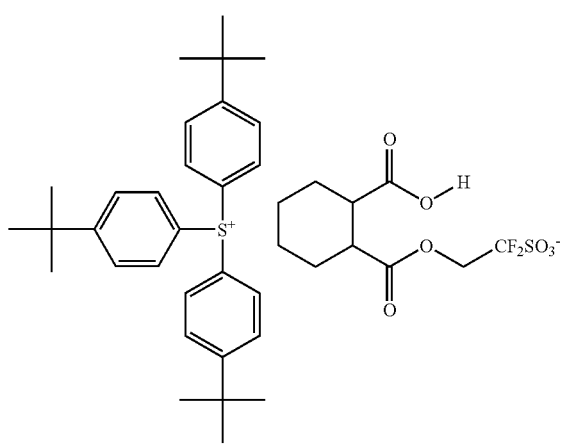
[PAG G]
[PAG H]
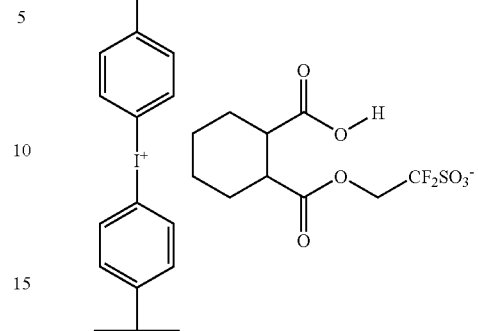
[PAG I]
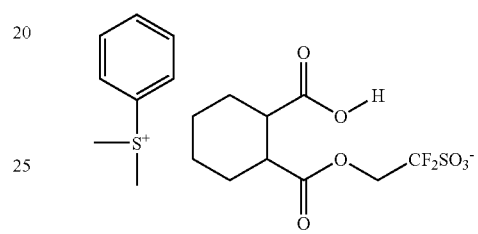
[PAG J]
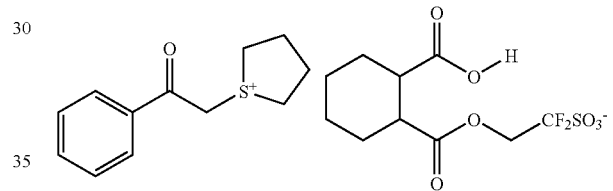
[PAG K]
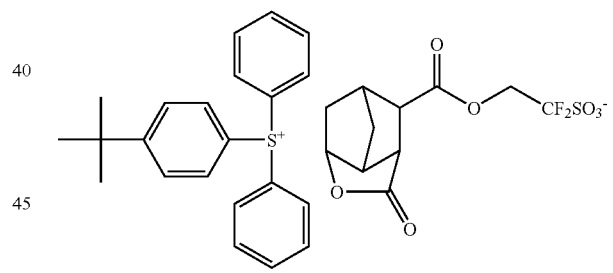
[PAG L]
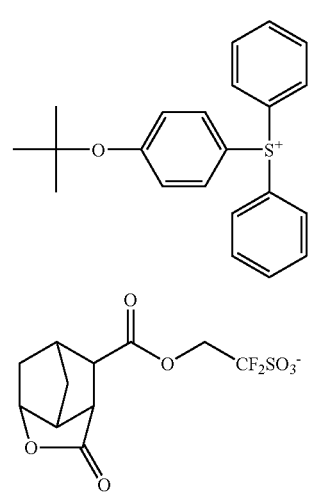

[PAG M]
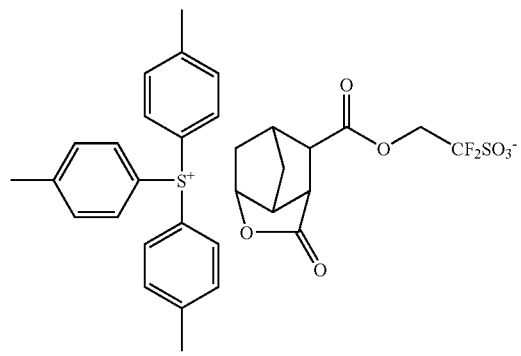
[PAG N]
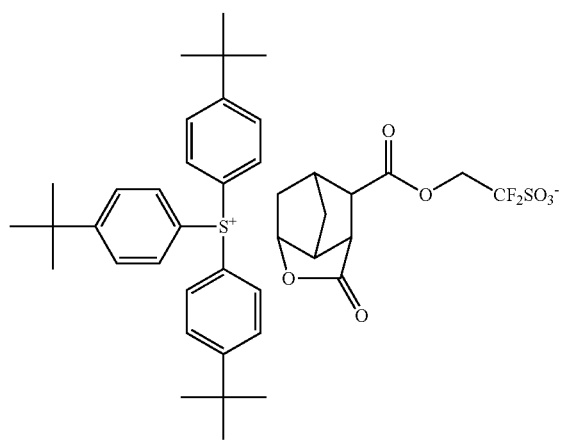
[PAG O]
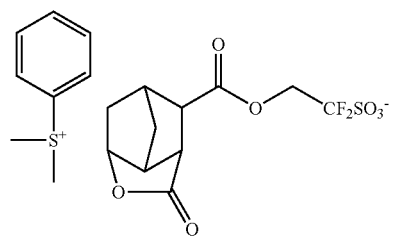
[PAG P]
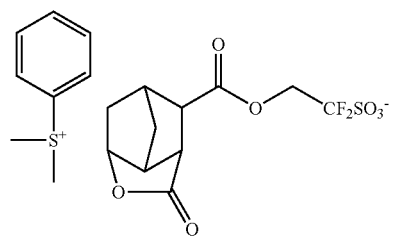
[PAG Q]
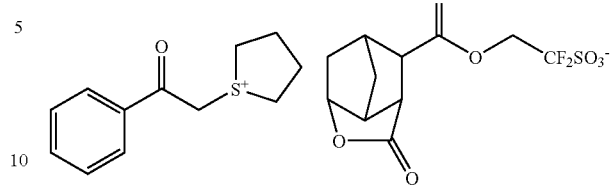
[PAG R]
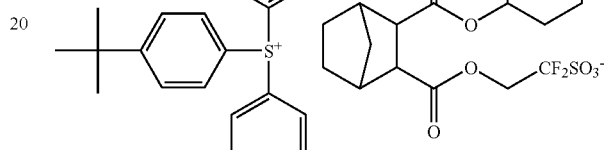
[PAG S]
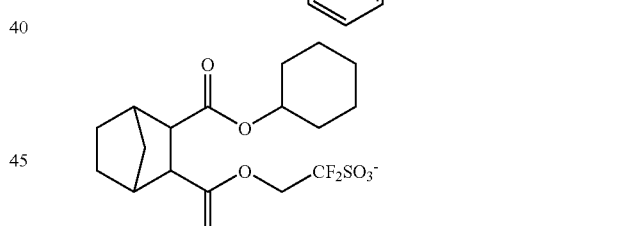
[PAG T]
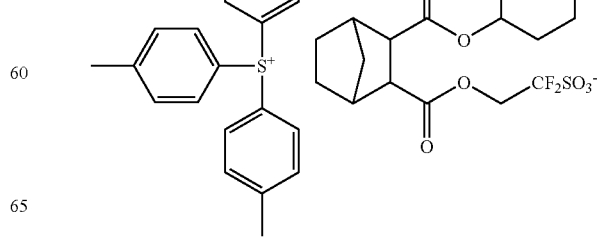

-continued

[PAG U]

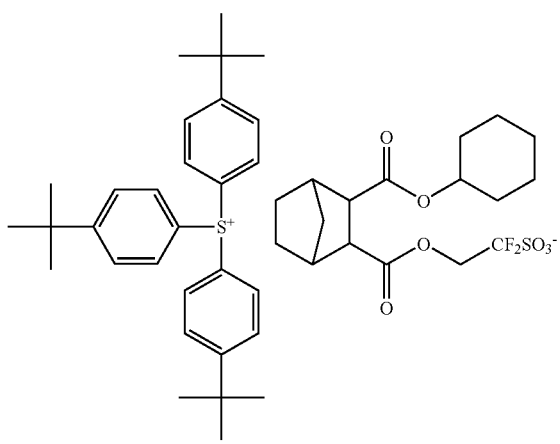

[PAG V]

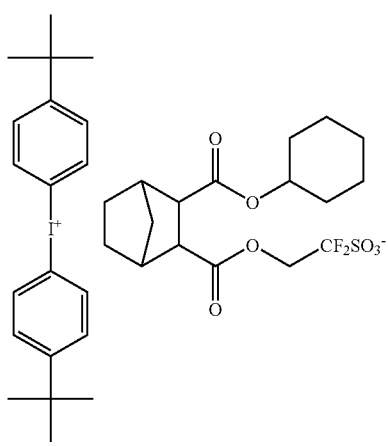

[PAG W]

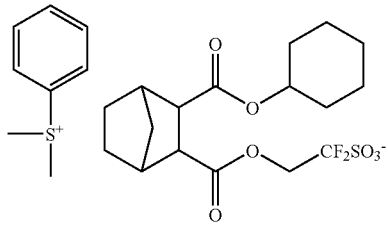

[PAG X]

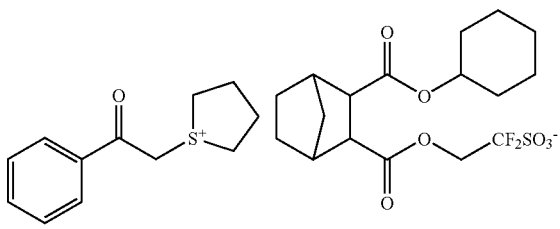

Polymers for use in the resist compositions of the invention were synthesized in accordance with the following formulation.

Synthesis Example 2-1

Synthesis of Polymer 1

A flask purged with nitrogen was charged with 168.6 g of 2-ethyladamantan-2-yl methacrylate, 85.5 g of 3-hydroxy-1-adamantyl methacrylate, 172.1 g of 2-oxotetrahydrofuran-3-yl methacrylate, and 510 g of propylene glycol methyl ether acetate (PMA) to form a monomer solution. An initiator solution was prepared by adding 14.86 g of 2,2'-azobisisobutyronitrile and 2.6 g of 2-mercaptoethanol to 127 g of PMA. Another flask purged with nitrogen was charged with 292 g of PMA, which was heated at 80° C. while stirring. Thereafter, the monomer solution and the initiator solution were simultaneously added dropwise over 4 hours. After the completion of dropwise addition, the polymerization solution was stirred for a further 2 hours while maintaining the temperature of 80° C., and thereafter, cooled down to room temperature. With vigorous stirring, the polymerization solution was added dropwise to 12 kg of methanol, whereupon a copolymer precipitated. The copolymer was collected by filtration, washed twice with 3 kg of methanol, and vacuum dried at 50° C. for 20 hours, obtaining 384 g of the copolymer in white powder form. The copolymer was analyzed by $^{13}$C-NMR, finding a copolymerization compositional ratio of 33/18/49 mol % in the described order of monomers. It was also analyzed by GPC, finding a weight average molecular weight (Mw) of 6,000 versus polystyrene standards.

Polymer 1

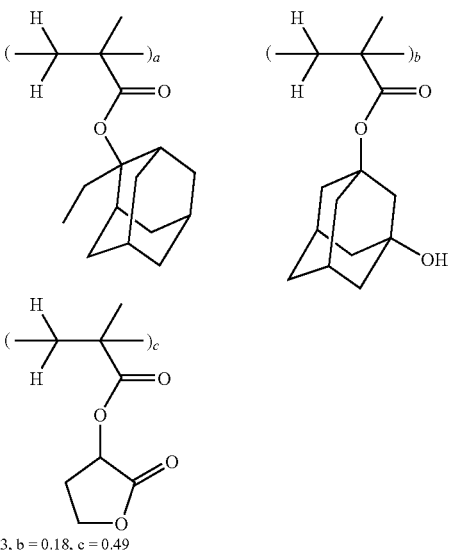

a = 0.33, b = 0.18, c = 0.49

Synthesis Examples 2-2 to 2-25

Synthesis of Polymers 2 to 25

A series of resins as shown in Table 1 were prepared by the same procedure as in Synthesis Example 2-1 except that the type and ratio of monomers were changed. The units in Table 1 have the structure shown in Tables 2 to 6. In Table 1, the ratio of units is a molar ratio.

Synthesis Examples 2-26 to 2-32

Synthesis of Polymers 26 to 32

Each of Polymers 19 to 25 obtained by the above formulation was dissolved in a solvent mixture of methanol and tetrahydrofuran, to which oxalic acid was added. Deprotection reaction took place at 40° C. The solution was neutralized with pyridine and purified by a standard reprecipitation technique, obtaining a polymer comprising hydroxystyrene units.

Synthesis Examples 2-33 to 2-35

Synthesis of Polymers 33 to 35

Polymers 26 to 28 were reacted with ethyl vinyl ether under acidic conditions or with 1-chloro-1-methoxy-2-methylpropane under basic conditions, obtaining Polymers 33 to 35.

With respect to the deprotection and protection of polyhydroxystyrene derivatives in Synthesis Examples 2-26 to 2-35, reference should be made to JP-A 2004-115630 and JP-A 2005-8766.

TABLE 1

|  |  | Resin | Unit 1 (ratio) | Unit 2 (ratio) | Unit 3 (ratio) | Unit 4 (ratio) |
|---|---|---|---|---|---|---|
| Synthesis Example | 2-1 | Polymer 1 | A-3M (0.33) | B-1M (0.18) | B-6M (0.49) |  |
|  | 2-2 | Polymer 2 | A-6M (0.25) | B-1M (0.25) | B-3M (0.40) | C-3M (0.10) |
|  | 2-3 | Polymer 3 | A-1M (0.25) | B-1M (0.25) | B-3M (0.40) | C-3M (0.10) |
|  | 2-4 | Polymer 4 | A-5M (0.30) | B-1M (0.25) | B-3M (0.35) | C-2M (0.10) |
|  | 2-5 | Polymer 5 | A-2M (0.40) | B-1M (0.25) | B-3M (0.35) |  |
|  | 2-6 | Polymer 6 | A-1M (0.25) | B-1M (0.25) | B-3M (0.40) | A-2M (0.10) |
|  | 2-7 | Polymer 7 | A-1M (0.30) | B-1M (0.15) | B-3M (0.45) | C-4M (0.10) |
|  | 2-8 | Polymer 8 | A-5M (0.25) | B-1M (0.25) | B-3M (0.40) | C-1M (0.10) |
|  | 2-9 | Polymer 9 | A-3M (0.35) | B-1M (0.35) | B-4M (0.30) |  |
|  | 2-10 | Polymer 10 | A-3M (0.35) | B-1M (0.35) | B-7M (0.30) |  |
|  | 2-11 | Polymer 11 | A-3M (0.30) | B-1M (0.26) | B-6M (0.34) | B-8M (0.10) |
|  | 2-12 | Polymer 12 | A-1M (0.25) | B-1M (0.25) | B-9M (0.40) | B-8M (0.10) |
|  | 2-13 | Polymer 13 | A-1M (0.25) | B-1M (0.25) | B-3M (0.40) | C-1M (0.10) |
|  | 2-14 | Polymer 14 | A-4M (0.30) | B-1M (0.25) | B-3M (0.45) |  |
|  | 2-15 | Polymer 15 | A-1M (0.30) | B-2M (0.35) | B-6M (0.35) |  |
|  | 2-16 | Polymer 16 | A-1M (0.30) | B-1M (0.35) | B-3M (0.35) |  |
|  | 2-17 | Polymer 17 | A-1M (0.35) | B-1M (0.25) | B-5M (0.40) |  |
|  | 2-18 | Polymer 18 | A-1M (0.20) | B-1M (0.25) | B-3M (0.35) | A-5M (0.20) |
|  | 2-19 | Polymer 19 | D-2 (1.0) |  |  |  |
|  | 2-20 | Polymer 20 | D-2 (0.80) | D-4 (0.20) |  |  |
|  | 2-21 | Polymer 21 | D-2 (0.70) | D-5 (0.30) |  |  |
|  | 2-22 | Polymer 22 | D-2 (0.70) | D-4 (0.15) | D-7 (0.15) |  |
|  | 2-23 | Polymer 23 | D-2 (0.80) | A-1M (0.15) | D-7 (0.05) |  |
|  | 2-24 | Polymer 24 | D-2 (0.75) | A-3M (0.15) | D-7 (0.10) |  |
|  | 2-25 | Polymer 25 | D-2 (0.80) | D-6 (0.20) |  |  |
|  | 2-26 | Polymer 26 | D-1 (1.0) |  |  |  |
|  | 2-27 | Polymer 27 | D-1 (0.80) | D-4 (0.20) |  |  |
|  | 2-28 | Polymer 28 | D-1 (0.70) | D-5 (0.30) |  |  |
|  | 2-29 | Polymer 29 | D-1 (0.70) | D-4 (0.15) | D-7 (0.15) |  |
|  | 2-30 | Polymer 30 | D-1 (0.80) | A-1M (0.15) | D-7 (0.05) |  |
|  | 2-31 | Polymer 31 | D-1 (0.75) | A-3M (0.15) | D-7 (0.10) |  |
|  | 2-32 | Polymer 32 | D-1 (0.80) | D-6 (0.20) |  |  |
|  | 2-33 | Polymer 33 | D-1 (0.80) | D-2 (0.20) |  |  |
|  | 2-34 | Polymer 34 | D-1 (0.80) | D-3 (0.20) |  |  |
|  | 2-35 | Polymer 35 | D-1 (0.70) | D-4 (0.20) | D-3 (0.10) |  |

TABLE 2

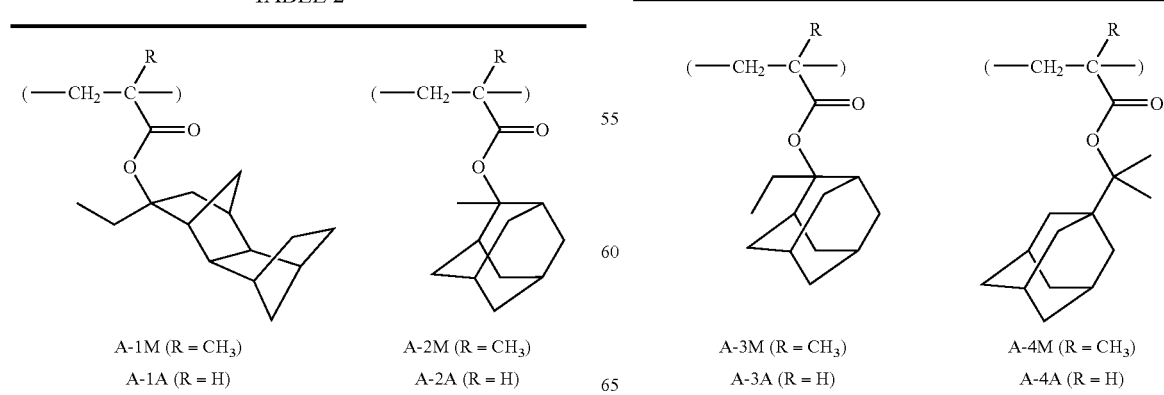

A-1M (R = CH$_3$)
A-1A (R = H)

A-2M (R = CH$_3$)
A-2A (R = H)

A-3M (R = CH$_3$)
A-3A (R = H)

A-4M (R = CH$_3$)
A-4A (R = H)

TABLE 2-continued
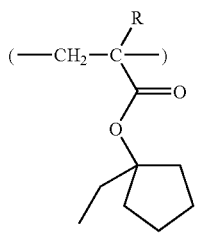
A-5M (R = CH₃)
A-5A (R = H)
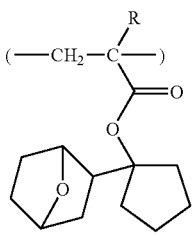
A-6M (R = CH₃)
A-6A (R = H)
TABLE 3
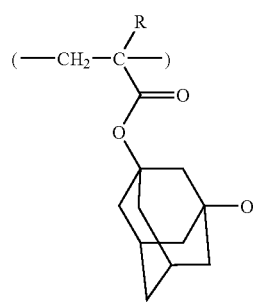
B-1M (R = CH₃)
B-1A (R = H)
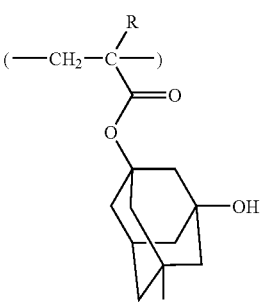
B-2M (R = CH₃)
B-2A (R = H)
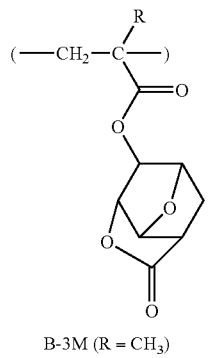
B-3M (R = CH₃)
B-3A (R = H)
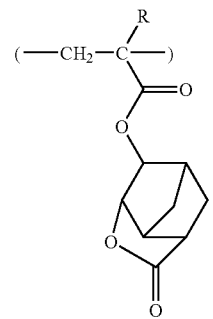
B-4M (R = CH₃)
B-4A (R = H)
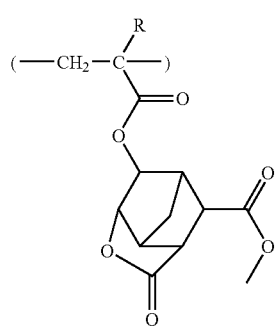
B-5M (R = CH₃)
B-5A (R = H)
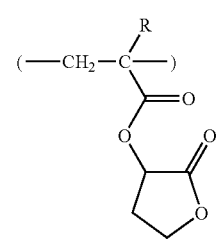
B-6M (R = CH₃)
B-6A (R = H)
TABLE 3-continued
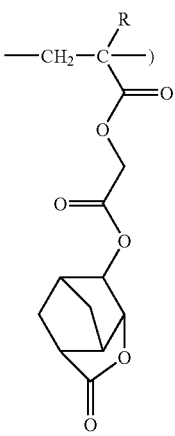
B-7M (R = CH₃)
B-7A (R = H)
TABLE 4
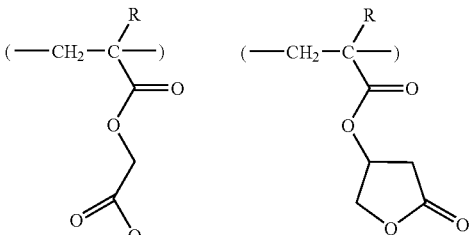
B-8M (R = CH₃)
B-8A (R = H)
B-9M (R = CH₃)
B-9A (R = H)
TABLE 5
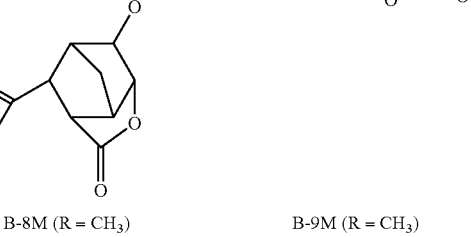
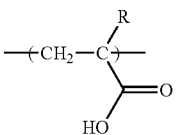
C-1M (R = CH₃)
C-1A (R = H)
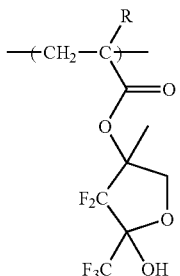
C-2M (R = CH₃)
C-2A (R = H)

TABLE 5-continued
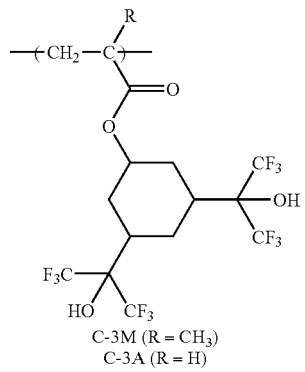
C-3M (R = CH₃)
C-3A (R = H)
C-4M (R = CH₃)
C-4A (R = H)
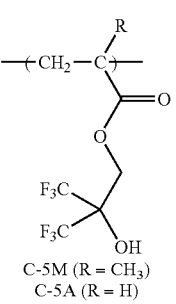
C-5M (R = CH₃)
C-5A (R = H)
TABLE 6
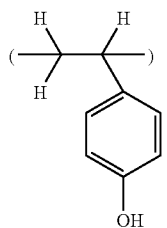
D-1
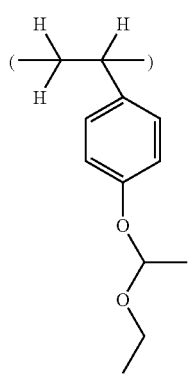
D-2
TABLE 6-continued
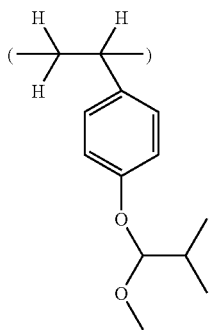
D-3
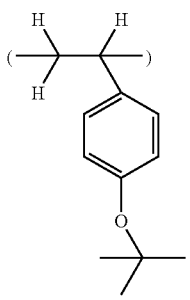
D-4
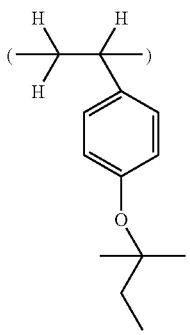
D-5
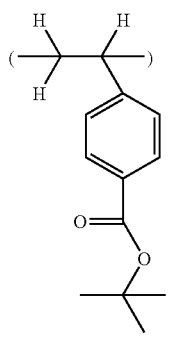
D-6
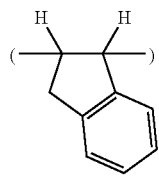
D-7

Additionally, the following polymers (Polymers 36 to 40) were prepared by well-known techniques.

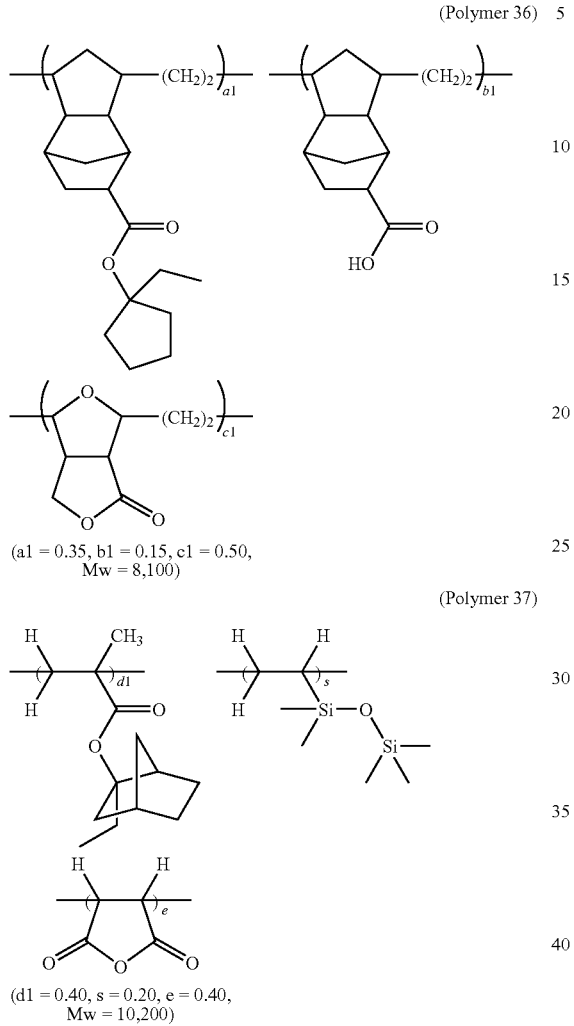

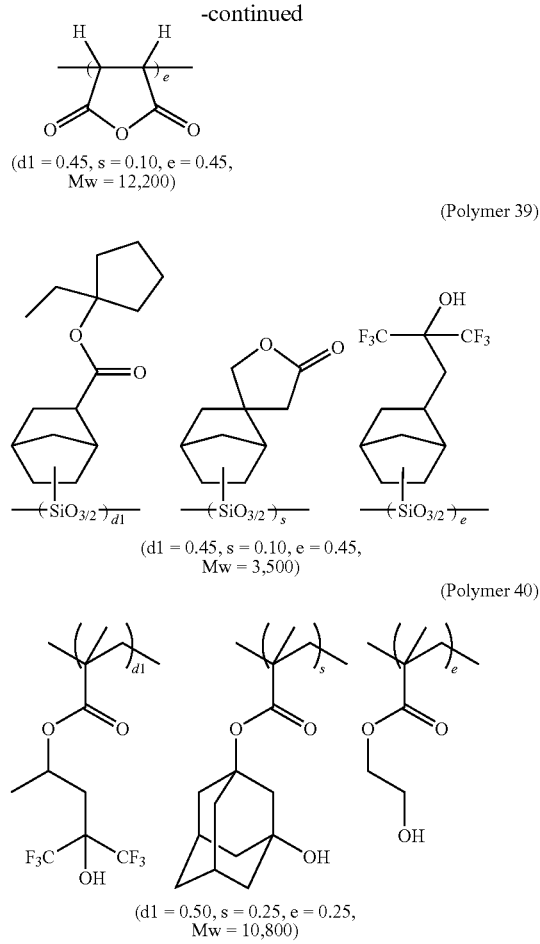

Examples 1 to 32 & Comparative Examples 1 to 4

Preparation of Resist Composition

Resist compositions were prepared by dissolving the photoacid generators of Synthesis Example 1, Polymers P-01 to P-40 of Synthesis Example 2 as the base resin, and a quencher in a solvent containing 0.01 wt % of surfactant KH-20 (Seimi Chemical Co., Ltd.) according to the formulation shown in Table 7. They were filtered through a Teflon® filter having a pore size of 0.2 μm, giving resist solutions.

In Table 7, the solvents, quenchers, photoacid generators in Comparative Examples, and acid crosslinker are shown below. PAG-A, B and C are designated PAG-1, 2 and 3, respectively. Polymers 1 to 40 are designated P-01 to P-40, respectively.

TABLE 7

|  |  | Resist composition | Resin (pbw) | PAG (pbw) | Additive (pbw) | Solvent 1 (pbw) | Solvent 2 (pbw) |
|---|---|---|---|---|---|---|---|
| Example | 1 | R-01 | P-01 (80) | PAG-1 (7.4) | Base-2 (1.10) | PGMEA (896) | CyHO (364) |
|  | 2 | R-02 | P-01 (80) | PAG-2 (8.1) | Base-2 (1.10) | PGMEA (896) | CyHO (364) |
|  | 3 | R-03 | P-01 (80) | PAG-3 (8.2) | Base-2 (1.10) | PGMEA (896) | CyHO (364) |
|  | 4 | R-04 | P-02 (80) | PAG-1 (7.4) | Base-2 (1.10) | PGMEA (896) | CyHO (364) |
|  | 5 | R-05 | P-03 (80) | PAG-1 (7.4) | Base-2 (1.10) | PGMEA (896) | CyHO (364) |
|  | 6 | R-06 | P-04 (80) | PAG-1 (7.9) | Base-2 (1.10) | PGMEA (896) | CyHO (364) |
|  | 7 | R-07 | P-05 (80) | PAG-1 (7.4) | Base-2 (1.10) | PGMEA (896) | CyHO (364) |
|  | 8 | R-08 | P-06 (80) | PAG-1 (5.0) PAG-3 (2.0) | Base-2 (1.10) | PGMEA (896) | CyHO (364) |

TABLE 7-continued

|  | Resist composition | Resin (pbw) | PAG (pbw) | Additive (pbw) | Solvent 1 (pbw) | Solvent 2 (pbw) |
|---|---|---|---|---|---|---|
|  | 9 R-09 | P-07 (80) | PAG-1 (7.4) | Base-2 (1.10) | PGMEA (896) | CyHO (364) |
|  | 10 R-10 | P-08 (80) | PAG-1 (7.4) | Base-2 (1.10) | PGMEA (896) | CyHO (364) |
|  | 11 R-11 | P-09 (80) | PAG-1 (7.4) | Base-2 (1.10) | PGMEA (896) | CyHO (364) |
|  | 12 R-12 | P-10 (80) | PAG-1 (7.4) | Base-2 (1.10) | PGMEA (896) | CyHO (364) |
|  | 13 R-13 | P-11 (80) | PAG-1 (7.4) | Base-2 (1.10) | PGMEA (896) | CyHO (364) |
|  | 14 R-14 | P-12 (80) | PAG-1 (7.4) | Base-2 (1.10) | PGMEA (896) | CyHO (364) |
|  | 15 R-15 | P-13 (80) | PAG-1 (5.0) PAG-2 (2.0) | Base-2 (1.10) | PGMEA (896) | CyHO (364) |
|  | 16 R-16 | P-14 (80) | PAG-1 (7.4) | Base-2 (1.10) | PGMEA (896) | CyHO (364) |
|  | 17 R-17 | P-15 (80) | PAG-1 (7.4) | Base-2 (1.10) | PGMEA (896) | CyHO (364) |
|  | 18 R-18 | P-16 (80) | PAG-1 (7.4) | Base-2 (1.10) | PGMEA (896) | CyHO (364) |
|  | 19 R-19 | P-17 (80) | PAG-1 (7.4) | Base-2 (1.10) | PGMEA (896) | CyHO (364) |
|  | 20 R-20 | P-18 (80) | PAG-1 (7.4) | Base-1 (1.10) | PGMEA (896) | CyHO (364) |
|  | 21 R-21 | P-03 (40) P-36 (40) | PAG-1 (7.4) | Base-1 (1.10) | PGMEA (896) | CyHO (364) |
|  | 22 R-22 | P-05 (40) P-36 (40) | PAG-1 (7.4) | Base-1 (1.10) | PGMEA (896) | CyHO (364) |
|  | 23 R-23 | P-37 (80) | PAG-1 (7.4) | Base-1 (1.10) | PGMEA (896) | CyHO (364) |
|  | 24 R-24 | P-38 (80) | PAG-1 (7.4) | Base-1 (1.10) | PGMEA (896) | CyHO (364) |
|  | 25 R-25 | P-27 (80) | PAG-1 (7.4) | Base-1 (0.94) | PGMEA (896) | EL (364) |
|  | 26 R-26 | P-28 (80) | PAG-1 (7.4) | Base-1 (0.94) | PGMEA (896) | EL (364) |
|  | 27 R-27 | P-29 (80) | PAG-1 (7.4) | Base-1 (0.94) | PGMEA (896) | EL (364) |
|  | 28 R-28 | P-30 (80) | PAG-1 (7.4) | Base-1 (0.94) | PGMEA (896) | EL (364) |
|  | 29 R-29 | P-31 (80) | PAG-1 (7.4) | Base-1 (0.94) | PGMEA (896) | EL (364) |
|  | 30 R-30 | P-32 (80) | PAG-1 (7.4) | Base-1 (0.94) | PGMEA (896) | EL (364) |
|  | 31 R-31 | P-35 (80) | PAG-1 (7.4) | Base-1 (0.94) | PGMEA (896) | EL (364) |
|  | 32 R-32 | P-26 (80) | PAG-1 (7.4) | Base-1 (0.3) TMGU (10) | PGMEA (896) | EL (364) |
| Comparative Example | 1 R-101 | P-01 (80) | PAG-Y (6.5) | Base-2 (1.10) | PGMEA (896) | CyHO (364) |
|  | 2 R-102 | P-01 (80) | PAG-Z (7.6) | Base-2 (1.10) | PGMEA (896) | CyHO (364) |
|  | 3 R-103 | P-01 (80) | PAG-Y (5.0) PAG-Z (2.0) | Base-2 (1.10) | PGMEA (896) | CyHO (364) |
|  | 4 R-104 | P-27 (80) | PAG-Z (7.4) | Base-1 (0.94) | PGMEA (896) | EL (364) |

PGMEA: propylene glycol monomethyl ether acetate
CyHO: cyclohexanone
EL: ethyl lactate
Base-1: triethanolamine
Base-2: tris[2-(methoxymethoxy)ethyl]amine
PAG-Y: triphenylsulfonium perfluoro-1-butanesulfonate
PAG-Z: triphenylsulfonium 2-(adamantane-1-carbonyloxy)-1,1,3,3,3-pentafluoropropane-1-sulfonate (described in JP-A 2007-145797)
TMGU: 1,3,4,6-tetramethoxymethylglycoluril Examples 33 to 56 & Comparative Examples 5 to 7

Evaluation of Resist Resolution and Mask Fidelity on ArF Lithography

An antireflective coating liquid ARC-29A (Nissan Chemical Co., Ltd.) was coated onto a silicon substrate and baked at 200° C. for 60 seconds to form an antireflective coating of 78 nm thick. The resist solution, prepared above, was spin coated onto the ARC and baked on a hot plate at 120° C. for 60 seconds, forming a resist film of 160 nm thick. The resist film was exposed by means of an ArF excimer laser microstepper model NSR-S307E (Nikon Corp., NA 0.85, dipole illumination, Cr mask), post-exposure baked (PEB) at the temperature shown in Table 8 for 60 seconds, and developed with a 2.38 wt % aqueous solution of tetramethylammonium hydroxide (TMAH) for 60 seconds.

An optimum exposure dose (sensitivity Eop, mJ/cm$^2$) was the exposure which provided a 1:1 resolution at the top and bottom of a 80-nm grouped line-and-space pattern. The minimum line width (nm) of a line-and-space pattern which was ascertained separate at this dose was the resolution of a test resist. For the evaluation of pattern density dependency, a 1:10 isolated line pattern with an on-mask size of 130 nm was formed at the optimum exposure and determined for an actual on-wafer size, which was reported as mask fidelity (a larger value of on-wafer size is better). For the evaluation of exposure latitude, an exposure dose tolerance which provided a pattern size of 80 nm±10% when the exposure dose was changed from the optimum was determined, and the tolerance value was divided by the optimum dose and expressed in percent. A greater value indicates a smaller performance change with a change of exposure dose, that is, better exposure latitude.

The test results of resist compositions are shown in Table 8.

TABLE 8

|  | Resist composition | PEB temp. (° C.) | Eop (mJ/cm$^2$) | Maximum resolution (nm) | Mask fidelity (nm) | Exposure latitude (%) |
|---|---|---|---|---|---|---|
| Example | 33 R-01 | 100 | 32 | 65 | 75 | 13 |
|  | 34 R-02 | 100 | 40 | 70 | 75 | 14 |
|  | 35 R-03 | 100 | 42 | 70 | 80 | 14 |
|  | 36 R-04 | 100 | 32 | 65 | 80 | 14 |
|  | 37 R-05 | 100 | 30 | 65 | 78 | 13 |
|  | 38 R-06 | 100 | 32 | 65 | 75 | 13 |
|  | 39 R-07 | 110 | 40 | 70 | 75 | 14 |
|  | 40 R-08 | 100 | 31 | 70 | 80 | 13 |
|  | 41 R-09 | 100 | 30 | 70 | 75 | 13 |
|  | 42 R-10 | 100 | 33 | 70 | 75 | 13 |
|  | 43 R-11 | 105 | 30 | 70 | 78 | 12 |
|  | 44 R-12 | 100 | 30 | 70 | 80 | 12 |
|  | 45 R-13 | 100 | 28 | 75 | 60 | 10 |
|  | 46 R-14 | 100 | 32 | 70 | 78 | 13 |
|  | 47 R-15 | 100 | 30 | 65 | 70 | 13 |

TABLE 8-continued

|  |  | Resist com-position | PEB temp. (° C.) | Eop (mJ/cm$^2$) | Maximum resolution (nm) | Mask fidelity (nm) | Exposure latitude (%) |
|---|---|---|---|---|---|---|---|
|  | 48 | R-16 | 100 | 29 | 70 | 80 | 13 |
|  | 49 | R-17 | 100 | 30 | 70 | 80 | 13 |
|  | 50 | R-18 | 100 | 40 | 70 | 75 | 14 |
|  | 51 | R-19 | 100 | 31 | 70 | 80 | 13 |
|  | 52 | R-20 | 100 | 30 | 70 | 75 | 13 |
|  | 53 | R-21 | 100 | 33 | 70 | 75 | 13 |
|  | 54 | R-22 | 100 | 30 | 70 | 78 | 12 |
|  | 55 | R-23 | 100 | 30 | 70 | 80 | 12 |
|  | 56 | R-24 | 100 | 28 | 75 | 60 | 10 |
| Com- | 5 | R-101 | 100 | 32 | 70 | 78 | 13 |
| parative | 6 | R-102 | 100 | 30 | 65 | 70 | 13 |
| Example | 7 | R-103 | 100 | 29 | 70 | 80 | 13 |

Examples 57 to 59 & Comparative Example 8

Simulative immersion photolithography was carried out using the resist compositions (R-01, R-04, R-05) of the invention and the resist composition (R-101) for comparison. Specifically, a resist film of 125 nm thick was formed on a wafer by a procedure as described above and exposed by means of an ArF excimer laser microstepper model S307E (Nikon Corp., dipole). Immediately after the exposure, deionized water was fed over the entire surface of the wafer, whereby the exposed surface of resist was immersed in deionized water for 60 seconds (puddle). The wafer was rotated to spin off the water, followed by ordinary PEB and development. The number of defects in the pattern formed after development was counted by a wafer inspection system WINWIN 50-1200L (Tokyo Seimitsu Co., Ltd.). A defect density was computed therefrom.

Defect density (/cm$^2$)=(total number of detected defects)/(test area).

Pattern formed: repetitive pattern of 80 nm (pitch 160 nm) line-and-space

Defect detection: light source UV, detection pixel size 0.125 μm, cell-to-cell mode Additionally, the pattern profile in resist cross-section was observed under a scanning electron microscope (SEM). The results are shown in Table 9.

TABLE 9

|  | Resist composition | Pattern profile | Defect density (/cm$^2$) |
|---|---|---|---|
| Example 57 | R-01 | Rectangular | ≦0.05 |
| Example 58 | R-04 | Rectangular | ≦0.05 |
| Example 59 | R-05 | Rectangular | ≦0.05 |
| Comparative Example 8 | R-101 | Extremely Bulged Top | 10 |

As is evident from Tables 8 and 9, the resist compositions of the invention have a high sensitivity, high resolution and minimized pattern density dependency, and invite neither profile changes nor defects during a long term of water rinsing as compared with the prior art composition, suggesting an ability to comply with the immersion photolithography.

Examples 60, 61 & Comparative Example 9

Evaluation of Resolution on EB Exposure

On a 8-inch silicon wafer having an organic antireflective coating (DUV-44 by Brewer Science) of 610 Å thick coated thereon, each of the resist compositions (R-25, R-32) of the invention or a comparative resist composition (R-104) was spin coated and heat treated at 100° C. for 60 seconds to form a resist film of 2000 Å thick. Using an EB lithography system HL-800D (Hitachi Hitechnologies, Ltd.) at an accelerating voltage of 50 keV, exposure was performed on the resist film. The resist film was post-exposure baked (PEB) at 120° C. for 60 seconds and developed with a 2.38 wt % TMAH aqueous solution, obtaining a positive pattern (Example 60, Comparative Example 9) or a negative pattern (Example 61).

The resist pattern was evaluated as follows. The optimum exposure (sensitivity, Eop) was defined as the exposure dose (μC/cm$^2$) which provided a 1:1 resolution at the top and bottom of a 0.12-μm line-and-space pattern. The resolution of the resist was defined as the minimum line width of a line-and-space pattern that was ascertained separate at the optimum exposure. The profile of the resolved resist pattern was evaluated by observing a cross section of the resist under a SEM.

The post-exposure delay (PED) in vacuum was evaluated by exposing the coated wafer on an EB lithography system, holding it in the vacuum system for 24 hours, thereafter effecting PEB and development. The size of lines of a 0.12-μm line-and-space pattern was measured and a percent change thereof was calculated. If the line size increased by 0.012 μm, the change is reported as +10%. A smaller change indicates better stability. The test results are shown in Table 10.

TABLE 10

|  | Resist composition | Eop (μC/cm$^2$) | Resolution (μm) | Pattern profile | Line size change by PED |
|---|---|---|---|---|---|
| Example 60 | R-25 | 20 | 0.08 | Rectangular | 0 |
| Example 61 | R-32 | 27 | 0.08 | Rectangular | 0 |
| Comparative Example 9 | R-104 | 28 | 0.10 | Somewhat rounded top | +10% |

It is evident from Table 10 that the resist composition of the invention is also improved in resolution and vacuum PED when processed by EB lithography. The resist composition is expected to perform equally when processed by the EUV or KrF lithography using polyhydroxystyrene derivatives.

Japanese Patent Application No. 2008-078049 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A photoacid generator for chemically amplified resist compositions which generates a sulfonic acid in response to high-energy radiation selected from UV, deep-UV, EUV, electron beam, x-ray, excimer laser, gamma-ray and synchrotron radiation, said sulfonic acid having the general formula (1a):

$$ROC(=O)R^1-COOCH_2CF_2SO_3^-H^+ \quad (1a)$$

wherein RO is hydroxyl or a substituted or unsubstituted, straight, branched or cyclic $C_1$-$C_{20}$ organoxy group, $R^1$ is a divalent $C_1$-$C_{20}$ aliphatic group which may contain a substituent group having a heteroatom such as oxygen, nitrogen or sulfur, or may form a mono- or polycyclic structure with RO.

2. A sulfonium salt having the general formula (2):

$$ROC(=O)R^1-COOCH_2CF_2SO_3^-R^2R^3R^4S^+ \quad (2)$$

wherein RO is hydroxyl or a substituted or unsubstituted, straight, branched or cyclic $C_1$-$C_{20}$ organoxy group, $R^1$ is a divalent $C_1$-$C_{20}$ aliphatic group which may contain a substituent group having a heteroatom such as oxygen, nitrogen or sulfur, or may form a mono- or polycyclic structure with RO, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom.

3. A sulfonium salt having the general formula (2a):

$$ROC(=O)R^1-COOCH_2CF_2SO_3^-(R^5(O)_n)_mPh'S^+Ph_2 \quad (2a)$$

wherein RO is hydroxyl or a substituted or unsubstituted, straight, branched or cyclic $C_1$-$C_{20}$ organoxy group, $R^1$ is a divalent $C_1$-$C_{20}$ aliphatic group which may contain a substituent group having a heteroatom such as oxygen, nitrogen or sulfur, or may form a mono- or polycyclic structure with RO, $R^5$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 or 1, Ph denotes phenyl, and Ph' denotes a phenyl group in which a number "m" of hydrogen atoms are substituted by $R^5(O)_n$— groups.

4. An iodonium salt having the general formula (2b):

$$ROC(=O)R^1-COOCH_2CF_2SO_3^-((R^5(O)_n)_mPh')_2I^+ \quad (2b)$$

wherein RO is hydroxyl or a substituted or unsubstituted, straight, branched or cyclic $C_1$-$C_{20}$ organoxy group, $R^1$ is a divalent $C_1$-$C_{20}$ aliphatic group which may contain a substituent group having a heteroatom such as oxygen, nitrogen or sulfur, or may form a mono- or polycyclic structure with RO, $R^5$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 or 1, and Ph' denotes a phenyl group in which a number "m" of hydrogen atoms are substituted by $R^5(O)_n$— groups.

5. A resist composition comprising
a base resin,
an acid generator, and
an organic solvent,
said acid generator comprising
(a) a photoacid generator for chemically amplified resist compositions which generates a sulfonic acid in response to high-energy radiation selected from UV, deep-UV, EUV, electron beam, x-ray, excimer laser, gamma-ray and synchrotron radiation, said sulfonic acid having the general formula (1a):

$$ROC(=O)R^1-COOCH_2CF_2SO_3^-H^+ \quad (1a)$$

wherein RO is hydroxyl or a substituted or unsubstituted, straight, branched or cyclic $C_1$-$C_{20}$ organoxy group, $R^1$ is a divalent $C_1$-$C_{20}$ aliphatic group which may contain a substituent group having a heteroatom such as oxygen, nitrogen or sulfur, or may form a mono- or polycyclic structure with RO,
(b) a sulfonium salt having the general formula (2):

$$ROC(=O)R^1-COOCH_2CF_2SO_3^-R_2R^3R^4S^+ \quad (2)$$

wherein RO is hydroxyl or a substituted or unsubstituted, straight, branched or cyclic $C_1$-$C_{20}$ organoxy group, $R^1$ is a divalent $C_1$-$C_{20}$ aliphatic group which may contain a substituent group having a heteroatom such as oxygen, nitrogen or sulfur, or may form a mono- or polycyclic structure with RO, $R^2$, $R^3$ and $R^4$ are each independently a substituted or unsubstituted, straight or branched $C_1$-$C_{10}$ alkyl, alkenyl or oxoalkyl group or a substituted or unsubstituted $C_6$-$C_{18}$ aryl, aralkyl or aryloxoalkyl group, or at least two of $R^2$, $R^3$ and $R^4$ may bond together to form a ring with the sulfur atom, or
(c) an iodonium salt having the general formula (2b):

$$ROC(=O)R^1-COOCH_2CF_2SO_3^-((R^5(O)_n)_mPh')_2I^+ \quad (2b)$$

wherein RO is hydroxyl or a substituted or unsubstituted, straight, branched or cyclic $C_1$-$C_{20}$ organoxy group, $R^1$ is a divalent $C_1$-$C_{20}$ aliphatic group which may contain a substituent group having a heteroatom such as oxygen, nitrogen or sulfur, or may form a mono- or polycyclic structure with RO, $R^5$ is a substituted or unsubstituted, straight, branched or cyclic $C_1$-$C_{20}$ alkyl or alkenyl group or a substituted or unsubstituted $C_6$-$C_{14}$ aryl group, m is an integer of 1 to 5, n is 0 or 1, and Ph' denotes a phenyl group in which a number "m" of hydrogen atoms are substituted by $R^5(O)_n$— groups.

6. The resist composition of claim 5, wherein said base resin is one or more polymers selected from the group consisting of poly(meth)acrylic acid and derivatives thereof, cycloolefin derivative/maleic anhydride alternating copolymers, copolymers of ternary or more components comprising a cycloolefin derivative, maleic anhydride, and polyacrylic acid or derivatives thereof, cycloolefin derivative/α-trifluoromethyl acrylate derivative copolymers, polynorbornene, ring-opening metathesis polymers, and hydrogenated ring-opening metathesis polymers.

7. The resist composition of claim 5, wherein said base resin is a polymeric structure containing silicon atoms.

8. The resist composition of claim 5, wherein said base resin is a polymeric structure containing fluorine atoms.

9. A chemically amplified positive resist composition comprising
a base resin, wherein said base resin is one or more polymers selected from the group consisting of poly(meth) acrylic acid and derivatives thereof, cycloolefin derivative/maleic anhydride alternating copolymers, copolymers of ternary or more components comprising a cycloolefin derivative, maleic anhydride, and polyacrylic acid or derivatives thereof, cycloolefin derivative/α-trifluoromethyl acrylate derivative copolymers, polynorbornene, ring-opening metathesis polymers, and hydrogenated ring-opening metathesis polymers,
a photoacid generator capable of generating a sulfonic acid having formula (1a) as set forth in claim 1, and
a solvent,
wherein said base resin is insoluble or substantially insoluble in a developer, and becomes soluble under the action of the acid.

10. The resist composition of claim 9, further comprising a quencher.

11. The resist composition of claim 9, further comprising a dissolution inhibitor.

12. The resist composition of claim 9, further comprising a surfactant which is insoluble in water and soluble in an alkaline developer.

13. A pattern forming process comprising the steps of:
applying the resist composition of claim 9 onto a substrate to form a coating,
heat treating the coating and exposing it to high-energy radiation through a photomask, and
optionally heat treating and developing the exposed coating with a developer.

14. A pattern forming process comprising the steps of:
applying the resist composition of claim 9 onto a substrate to form a resist coating,
heat treating the resist coating, applying on the resist coating a protective coating which is insoluble in water and soluble in an alkaline developer, exposing the coated substrate to high-energy radiation through a photomask and a projection lens, while holding water between the coated substrate and the projection lens, and optionally heat treating, and developing the exposed coating with a developer.

15. A pattern forming process comprising the steps of applying the resist composition of claim 9 onto a substrate to form a coating, heat treating the coating, imagewise writing with an electron beam, optionally heat treating the coating, and developing it with a developer.

16. A pattern forming process comprising the steps of applying the resist composition of claim 9 onto a substrate to form a coating, heat treating the coating and exposing it to high-energy radiation through a photomask, and heat treating and developing the exposed coating with a developer, wherein the process further comprises the step of applying a protective coating on the resist coating, and the exposure step is performed by immersion lithography with a liquid having a refractive index of at least 1.0 held between the protective coating and a projection lens.

* * * * *